US009718858B2

(12) United States Patent
Cameron et al.

(10) Patent No.: US 9,718,858 B2
(45) Date of Patent: Aug. 1, 2017

(54) TUNABLE CONTROL OF PROTEIN DEGRADATION IN SYNTHETIC AND ENDOGENOUS BACTERIAL SYSTEMS

(71) Applicant: Trustees of Boston University, Boston, MA (US)

(72) Inventors: Douglas Ewen Cameron, Boston, MA (US); James J. Collins, Newton Centre, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 14/773,937

(22) PCT Filed: Mar. 13, 2014

(86) PCT No.: PCT/US2014/025654
§ 371 (c)(1),
(2) Date: Sep. 9, 2015

(87) PCT Pub. No.: WO2014/160025
PCT Pub. Date: Oct. 2, 2014

(65) Prior Publication Data
US 2016/0016995 A1   Jan. 21, 2016

Related U.S. Application Data

(60) Provisional application No. 61/779,547, filed on Mar. 13, 2013.

(51) Int. Cl.
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/06 | (2006.01) |
| C07K 5/097 | (2006.01) |
| C07K 14/30 | (2006.01) |
| G01N 33/50 | (2006.01) |
| C07K 5/083 | (2006.01) |
| C07K 5/087 | (2006.01) |
| C07K 5/09 | (2006.01) |
| C07K 5/093 | (2006.01) |
| C07K 5/103 | (2006.01) |
| C07K 5/107 | (2006.01) |
| C07K 5/11 | (2006.01) |
| C07K 5/117 | (2006.01) |
| C07K 7/06 | (2006.01) |

(52) U.S. Cl.
CPC ......... *C07K 5/0823* (2013.01); *C07K 5/0806* (2013.01); *C07K 5/0812* (2013.01); *C07K 5/0817* (2013.01); *C07K 5/0819* (2013.01); *C07K 5/101* (2013.01); *C07K 5/1016* (2013.01); *C07K 5/1019* (2013.01); *C07K 5/1024* (2013.01); *C07K 7/06* (2013.01); *C07K 14/30* (2013.01); *G01N 33/502* (2013.01); *C07K 2319/95* (2013.01); *G01N 2333/30* (2013.01); *G01N 2500/10* (2013.01)

(58) Field of Classification Search
None
See application file for complete search history.

(56) References Cited

U.S. PATENT DOCUMENTS

2012/0214170 A1   8/2012   Moore

FOREIGN PATENT DOCUMENTS

| WO | 2010075441 A1 | 7/2010 |
| WO | 2011066539 A2 | 6/2011 |
| WO | 2011066541 A2 | 6/2011 |

OTHER PUBLICATIONS

Gur E and Sauer R "Evolution of the ssrA degradation tag in Mycoplasma: Specificity switch to a different protease" Proc. Natl. Acad. Sci. 105:16113-16118. Published Oct. 21, 2008.*
Huang et al. "A genetic bistable switch utilizing nonlinear protein degradation" J. Biol. Eng. 6:9. Published Jul. 9, 2012.*
Andersen et al., "New Unstable Variants of Green Fluorescent Protein for Studies of Transient Gene Expression in Bacteria", Appl. Environ. Microbiol. 64(6):2240-2246 (1998).
Botos et al., "The Catalytic Domain of *Escherichia coli* Lon Protease Has a Unique Fold and a Ser-Lys Dyad in the Active Site", J. Biol. Chem. 279(9):8140-8148 (2004).
Davis et al., "Small-molecule control of protein degradation using split adaptors", ACS Chem. Biol. 6:1205-1213 (2011).
Flynn et al., "Overlapping recognition determinants within the ssrA degradation tag allow modulation of proteolysis", Proc. Natl. Acad. Sci. U.S.A. 98:10584-10589 (2001).
Flynn et al., "Proteomic Discovery of Cellular Substrates of the ClpXP Protease Reveals Five Classes of ClpX Recognition Signals", Mol. Cell 11(3):671-683 (2003).
Gardner et al., "Construction of a genetic toggle switch in *Escherichia coli*", Nature 403(6767):339-342 (2000).
Ge et al., "Co-Evolution of Multipartite Interactions Between an Extended tmRNA Tag and a Robust Lon Protease in Mycoplasma", Mol. Microbiol. 74(5)1083-1099 (2009).
Griffith et al., "Inducible protein degradation in Bacillus subtilis using heterologous peptide tags and adaptor proteins to target substrates to the protease ClpXP", Mol. Microbiol. 70(4):1012-1025 (2008).
Grilly et al., "A synthetic gene network for tuning protein degradation in *Saccharomyces cerevisiae*", Mol. Syst. Biol. 3(127):1-5 (2007).
Gur et al., "Evolution of the ssrA degradation tag in Mycoplasma: Specificity switch to a different protease", Proc.Natl. Acad. Sci., 105(42):16113-16118 (2008).

(Continued)

Primary Examiner — Christina Bradley
Assistant Examiner — Zachary J Miknis
(74) Attorney, Agent, or Firm — Nixon Peabody LLP; Ronald I. Eisenstein; Teresa A. Ptashka

(57) ABSTRACT

The methods and compositions described herein relate, in part, to the generation of a synthetic degradation system in *E. coli* that provides tunable control of the protein level of targeted genes by using components of the *Mesoplasma florum* tmRNA system. Provided herein are degradation tag variants that permit independent control of both the initial level and inducible degradation rate of attached proteins.

9 Claims, 25 Drawing Sheets

(56) References Cited

OTHER PUBLICATIONS

Huang et al., "A genetic bistable switch utilizing nonlinear protein degradation", J. Biol. Eng. 6(1):9 (2012).
Igem Ehime-Japan Team Poster (http://2012.igem.org/files/poster/Ehime-Japan.pdf).
Landry et al., "Use of Degradation Tags to Control Protein Levels in the *Cyanobacterium Synechocystis* sp. Strain PCC 6803", Applied and Environmental Microbiology 79(8):2833-2835 (2013).
McGinness et al., "Engineering Controllable Protein Degradation", Molecular Cell 22(5):701-707 (2006).
Moore et al., "The tmRNA System for Translational Surveillance and Ribosome Rescue", Annu. Rev. Biochem. 76:101-124 (2007).
Neklesa et al., "Small-Molecule Hydrophobic Tagging-Induced Degradation of HaloTag Fusion Proteins", Nat. Chem. Biol. 7(8):538-543 (2011).

\* cited by examiner

SEQUENCE LISTING

<160> NUMBER OF SEQ ID NOS: 125

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Asn Lys Asn Glu Glu Asn Thr Asn Glu Val Pro Thr Phe Met
1               5                   10                  15

Leu Asn Ala Gly Gln Ala Asn Tyr Ala Phe Ala
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Asn Lys Asn Glu Glu Asn Thr Asn Glu Val Pro Thr Phe Met
1               5                   10                  15

Leu Asn Ala Gly Gln Ala Asn Arg Leu Gln Leu
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Asn Lys Asn Glu Glu Asn Thr Asn Glu Val Pro Thr Phe Met
1               5                   10                  15

Leu Asn Ala Gly Gln Ala Asn Ile Cys Arg Leu
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Asn Lys Asn Glu Glu Asn Thr Asn Glu Val Pro Thr Phe Met
1               5                   10                  15

Leu Asn Ala Gly Gln Ala Asn Arg Leu Ser Gln
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 5

Ala Ala Asn Lys Asn Glu Glu Asn Thr Asn Glu Val Pro Thr Phe Met
1               5                   10                  15

Leu Asn Ala Gly Gln Ala Asn Tyr Gln Tyr Arg
            20                  25

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Asn Lys Asn Glu Glu Asn Thr Asn Glu Val Pro Thr Phe Met
1               5                   10                  15

Leu Asn Ala Gly Gln Ala Asn Arg Arg Arg Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Asn Lys Asn Glu Glu Asn Thr Asn Glu Val Pro Thr Phe Met
1               5                   10                  15

Leu Asn Ala Gly Gln Ala Asn His Ile Ser Pro
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Asn Lys Asn Glu Glu Asn Thr Asn Glu Val Pro Thr Phe Met
1               5                   10                  15

Leu Asn Ala Gly Gln Ala Asn Arg Ile Cys Arg
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Asn Lys Asn Glu Glu Asn Thr Asn Glu Val Pro Thr Phe Met
1               5                   10                  15

Leu Asn Ala Gly Gln Ala Asn His Ala Gln Pro
            20                  25

<210> SEQ ID NO 10
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Asn Lys Asn Glu Glu Asn Thr Asn Glu Val Pro Thr Phe Met
1               5                   10                  15

Leu Asn Ala Gly Gln Ala Asn Arg Gln Arg His
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Asn Lys Asn Glu Glu Asn Thr Asn Glu Val Pro Thr Phe Met
1               5                   10                  15

Leu Asn Ala Gly Gln Ala Asn Arg Ala Arg Gln
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Asn Lys Asn Glu Glu Asn Thr Asn Glu Val Pro Thr Phe Met
1               5                   10                  15

Leu Asn Ala Gly Gln Ala Asn Phe Thr Gln Gln
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Asn Lys Asn Glu Glu Asn Thr Asn Glu Val Pro Thr Phe Met
1               5                   10                  15

Leu Asn Ala Gly Gln Ala Asn Val Val Arg Arg
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Asn Lys Asn Glu Glu Asn Thr Asn Glu Val Pro Thr Phe Met
1               5                   10                  15
```

Leu Asn Ala Gly Gln Ala Asn Tyr Arg Thr Pro
            20                  25

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Asn Lys Asn Glu Glu Asn Thr Asn Glu Val Pro Thr Phe Met
1               5                   10                  15

Leu Asn Ala Gly Gln Ala Asn Arg Ala Gln Gln
            20                  25

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ala Asn Lys Asn Glu Glu Asn Thr Asn Glu Val Pro Thr Phe Met
1               5                   10                  15

Leu Asn Ala Gly Gln Ala Asn Arg Arg Gln Leu
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Asn Lys Asn Glu Glu Asn Thr Asn Glu Val Pro Thr Phe Met
1               5                   10                  15

Leu Asn Ala Gly Gln Ala Asn Gln Arg Gln Arg Gln
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Asn Lys Asn Glu Glu Asn Thr Asn Glu Val Arg Ala Ile Met
1               5                   10                  15

Leu Asn Ala Gly Gln Ala Asn Arg Arg Arg Val
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Asn Lys Asn Glu Glu Asn Thr Asn Glu Val Ala Pro Asn Met
1               5                   10                  15

Leu Asn Ala Gly Gln Ala Asn Arg Arg Arg Val
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Asn Lys Asn Glu Glu Asn Thr Asn Glu Val Pro Asp Ser Met
1               5                   10                  15

Leu Asn Ala Gly Gln Ala Asn Arg Arg Arg Val
            20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Asn Lys Asn Glu Glu Asn Thr Asn Glu Val Gln Pro Thr Met
1               5                   10                  15

Leu Asn Ala Gly Gln Ala Asn Arg Arg Arg Val
            20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Asn Lys Asn Glu Glu Asn Thr Asn Glu Val Ala Gln Pro Met
1               5                   10                  15

Leu Asn Ala Gly Gln Ala Asn Arg Arg Arg Val
            20                  25

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Asn Lys Asn Glu Glu Asn Thr Asn Glu Val Pro Ser Pro Met
1               5                   10                  15

Leu Asn Ala Gly Gln Ala Asn Arg Arg Arg Val
            20                  25

<210> SEQ ID NO 24

<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Ala Ala Asn Lys Asn Glu Glu Asn Thr Asn Glu Val Glu Arg Ala Met
1               5                   10                  15

Leu Asn Ala Gly Gln Ala Asn Arg Arg Arg Val
            20                  25
```

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Ala Ala Asn Lys Asn Glu Glu Asn Thr Asn Glu Val Trp Leu Gly Met
1               5                   10                  15

Leu Asn Ala Gly Gln Ala Asn Arg Arg Arg Val
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

```
Ala Ala Asn Lys Asn Glu Glu Asn Thr Asn Glu Val Pro Thr Phe Met
1               5                   10                  15

Leu Asn Ala Gly Gln Ala Asn Tyr Ala Phe Ala
            20                  25
```

<210> SEQ ID NO 27
<211> LENGTH: 149
<212> TYPE: PRT
<213> ORGANISM: Mesoplasma florum

<400> SEQUENCE: 27

```
Met Gly Glu His Val Ile Ala Leu Asn Lys Lys Ala Lys Phe Asn Tyr
1               5                   10                  15

Glu Ile Leu Glu Thr Trp Glu Ala Gly Ile Glu Leu Tyr Gly Pro Glu
            20                  25                  30

Ile Lys Ser Ile Arg Asn His Glu Ala Asn Ile Ala Glu Ala Phe Ile
        35                  40                  45

Leu Ile Arg Lys Lys Glu Ala Phe Leu Ile Asn Ala Asn Ile Lys Lys
    50                  55                  60

Tyr Asp Tyr Ala Asn Phe Val Lys Gly Ile Asp Pro Leu Arg Thr Arg
65                  70                  75                  80

Lys Leu Leu Leu His Lys Lys Glu Ile Asn Lys Ile Leu Lys Arg Val
                85                  90                  95

Met Leu Glu Lys Leu Thr Ile Val Pro Leu Arg Leu Tyr Leu Lys Gly
            100                 105                 110

Asn Tyr Ala Lys Leu Glu Ile Gly Leu Gly Arg Gly Lys Lys Ile His
```

```
            115                 120                 125
Asp Lys Arg Glu Thr Ile Lys Lys Arg Asp Ile Glu Arg Lys Glu Met
130                 135                 140

Arg Lys Tyr Lys Tyr
145

<210> SEQ ID NO 28
<211> LENGTH: 787
<212> TYPE: PRT
<213> ORGANISM: Mesoplasma florum

<400> SEQUENCE: 28

Met Ser Lys Lys Ile Lys Leu Pro Ile Phe Gln Ile Arg Gly Ser Phe
1               5                   10                  15

Ile Val Pro Gly Ile Lys Glu Asn Leu Glu Val Gly Arg Lys Asn Thr
            20                  25                  30

Leu Ala Ser Val Asn Tyr Ala Ile Lys Asn Ser Asn Asn Gln Met Ile
        35                  40                  45

Ala Ile Pro Gln Ile Asp Ala Ser Val Glu Lys Pro Glu Phe Ser Asp
    50                  55                  60

Leu His Glu Phe Gly Ile Leu Ile Asp Phe Glu Val Ile Lys Glu Trp
65                  70                  75                  80

Lys Asp Asn Ser Leu Thr Ile Ser Thr Asn Pro Ile Gln Arg Cys Lys
                85                  90                  95

Val Ile Ser Phe Phe Glu Asn Glu Asp Gln Val Pro Tyr Ala Glu Val
            100                 105                 110

Glu Leu Ile Glu Ser Ile Asn Asp Phe Ser Asp Glu Leu Lys Glu
        115                 120                 125

Leu Ile Glu Lys Ile Ser Asp Ala Ile Lys Thr Lys Ala Ser Leu Val
    130                 135                 140

Thr Lys Gln Ile Lys Gln Leu Ile Ser Gly Glu Ser Asp Asp Leu Ser
145                 150                 155                 160

Leu Ala Phe Asp Ser Ile Met Phe Lys Leu Ala Pro Ser Lys Ile Leu
                165                 170                 175

Thr Asn Pro Glu Tyr Ile Thr Ser Pro Ser Leu Lys Thr Arg Trp Ser
            180                 185                 190

Ile Ile Glu Lys Ile Ile Phe Ala Glu Asp Gly Ile Ile Thr Arg Asn
        195                 200                 205

Ala Glu Ser Ile Asp Ala Ala Arg Gln Lys Asn Glu Ile Glu Gln Glu
    210                 215                 220

Leu Asn His Lys Leu Lys Glu Lys Met Asp Lys Gln Gln Lys Glu Tyr
225                 230                 235                 240

Tyr Leu Arg Glu Lys Met Arg Ile Ile Lys Asp Glu Leu Glu Asp Glu
                245                 250                 255

Asp Asp Ser Asp Asp Ser Ser Leu Glu Lys Tyr Lys Glu Arg Leu Ala
            260                 265                 270

Lys Glu Pro Phe Pro Glu Glu Val Lys Arg Lys Ile Met Ala Ser Ile
        275                 280                 285

Lys Arg Val Glu Ala Leu Gln Ser Gly Thr Pro Glu Trp Asn Thr Glu
    290                 295                 300

Lys Asn Tyr Ile Asp Trp Met Met Ser Ile Pro Trp Trp Glu Glu Thr
305                 310                 315                 320

Glu Asp Leu Thr Asp Leu Lys Tyr Ala Lys Lys Ile Leu Asp Lys His
                325                 330                 335
```

```
His Tyr Gly Met Lys Lys Val Lys Glu Arg Ile Ile Glu Tyr Leu Ala
                340                 345                 350

Val Lys Thr Lys Thr Lys Ser Leu Lys Ala Pro Ile Ile Thr Leu Val
            355                 360                 365

Gly Pro Pro Gly Val Gly Lys Thr Ser Leu Ala Lys Ser Ile Ala Glu
        370                 375                 380

Ala Val Gly Lys Asn Phe Val Lys Val Ser Leu Gly Gly Val Lys Asp
385                 390                 395                 400

Glu Ser Glu Ile Arg Gly His Arg Lys Thr Tyr Val Gly Ser Met Pro
                405                 410                 415

Gly Arg Ile Ile Gln Thr Met Lys Arg Ala Lys Val Lys Asn Pro Leu
            420                 425                 430

Phe Leu Leu Asp Glu Ile Asp Lys Met Ala Ser Asp His Arg Gly Asp
        435                 440                 445

Pro Ala Ser Ala Met Leu Glu Val Leu Asp Pro Glu Gln Asn Lys Glu
    450                 455                 460

Phe Ser Asp His Tyr Ile Glu Glu Pro Tyr Asp Leu Ser Gln Val Met
465                 470                 475                 480

Phe Ile Ala Thr Ala Asn Tyr Pro Glu Asp Ile Pro Glu Ala Leu Tyr
                485                 490                 495

Asp Arg Met Glu Ile Ile Asn Leu Ser Ser Tyr Thr Glu Ile Glu Lys
            500                 505                 510

Val Lys Ile Ala Gln Asp Tyr Leu Val Pro Lys Ala Ile Glu Gln His
        515                 520                 525

Glu Leu Thr Ser Glu Gly Ile Ser Phe Thr Gly Ala Ile Asn Glu
    530                 535                 540

Ile Ile Lys Tyr Tyr Thr Arg Glu Ala Gly Val Arg Gln Leu Glu Arg
545                 550                 555                 560

His Ile Asn Ser Ile Ile Arg Lys Tyr Ile Val Lys Asn Leu Asn Gly
                565                 570                 575

Glu Met Asp Lys Ile Val Ile Asp Glu Lys Gln Val Asn Asp Leu Leu
            580                 585                 590

Gly Lys Arg Ile Phe Asp His Thr Glu Lys Gln Glu Glu Ser Gln Ile
        595                 600                 605

Gly Val Val Thr Gly Leu Ala Tyr Thr Gln Phe Gly Gly Asp Ile Leu
    610                 615                 620

Pro Ile Glu Val Ser Leu Tyr Pro Gly Lys Gly Asn Leu Ile Leu Thr
625                 630                 635                 640

Gly Lys Leu Gly Glu Val Met Lys Glu Ser Ala Thr Ile Ala Leu Thr
                645                 650                 655

Tyr Val Lys Ser Asn Phe Glu Lys Phe Gly Val Asp Lys Lys Val Phe
            660                 665                 670

Glu Glu Asn Asp Ile His Val His Val Pro Glu Gly Ala Val Pro Lys
        675                 680                 685

Asp Gly Pro Ser Ala Gly Ile Thr Ile Thr Ala Leu Ile Ser Ala
    690                 695                 700

Leu Ser Asp Lys Pro Val Ser Lys Glu Ile Gly Met Thr Gly Glu Ile
705                 710                 715                 720

Thr Leu Arg Gly Asn Val Leu Pro Ile Gly Gly Leu Arg Glu Lys Ser
                725                 730                 735

Ile Ser Ala Ser Arg Ser Gly Leu Lys Thr Ile Ile Pro Lys Lys
            740                 745                 750

Asn Glu Arg Asp Leu Asp Glu Ile Pro Asp Glu Val Lys Ala Lys Leu
```

```
                755                 760                 765
Lys Ile Ile Pro Ala Glu Lys Tyr Glu Glu Val Phe Ala Ile Val Phe
        770                 775                 780

Lys Thr Lys
785

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ala Phe Ala
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Gln Leu
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Leu Ser Gln
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Arg Val
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Ala Gln Pro
1
```

```
<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Arg Gln
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Cys Arg Leu
1

<210> SEQ ID NO 36
<211> LENGTH: 10
<212> TYPE: PRT
<213> ORGANISM: Escherichia coli

<400> SEQUENCE: 36

Ala Asn Asp Glu Asn Tyr Ala Leu Ala Ala
1               5                   10

<210> SEQ ID NO 37
<211> LENGTH: 27
<212> TYPE: PRT
<213> ORGANISM: Acinetobacter sp.

<400> SEQUENCE: 37

Gly Tyr Lys Leu His Ser Asn Phe Ser Gly Leu Cys Tyr Ser Val Ile
1               5                   10                  15

Leu Ile Trp Gly Cys Tyr Trp Leu Arg Arg Trp
            20                  25

<210> SEQ ID NO 38
<211> LENGTH: 28
<212> TYPE: PRT
<213> ORGANISM: Acinetobacter sp.

<400> SEQUENCE: 38

Met His Ala Glu Ser Ala Phe Ser Leu Val Asn Lys Ile Cys Ile Leu
1               5                   10                  15

Ile Val Ala Asn Asp Glu Thr Tyr Ala Leu Ala Ala
            20                  25

<210> SEQ ID NO 39
<211> LENGTH: 24
<212> TYPE: PRT
<213> ORGANISM: Acinetobacter sp.

<400> SEQUENCE: 39

Gly Gln Phe Val Arg Phe Leu Glu Tyr Leu Trp Phe Arg Asn Pro Thr
1               5                   10                  15

Val Ala His Ala His Lys Ser Val
            20
```

<210> SEQ ID NO 40
<211> LENGTH: 27
<212> TYPE: PRT
<213> ORGANISM: Acinetobacter sp.

<400> SEQUENCE: 40

Ser Gln Ala Ser Gly Leu Tyr Thr Lys Leu Arg Gly Ser His Leu Val
1               5                   10                  15
Pro Cys Ser Ser Gly His Trp Val Leu Lys Gln
            20                  25

<210> SEQ ID NO 41
<211> LENGTH: 27
<212> TYPE: PRT
<213> ORGANISM: Acinetobacter sp.

<400> SEQUENCE: 41

Thr Ile Ser Lys His Val Val Phe Ser Val Val Leu Ala Asp Ala
1               5                   10                  15
Gly Ser Thr Pro Ala Ile Ser Thr Lys Ile Thr
            20                  25

<210> SEQ ID NO 42
<211> LENGTH: 14
<212> TYPE: PRT
<213> ORGANISM: Acinetobacter sp.

<400> SEQUENCE: 42

Ile Asn Gln Pro Leu Thr Lys Val Ala Phe Leu Leu Ser Phe
1               5                   10

<210> SEQ ID NO 43
<211> LENGTH: 14
<212> TYPE: PRT
<213> ORGANISM: Acinetobacter sp.

<400> SEQUENCE: 43

Val Ile Asn Cys Ile Ala Ile Phe Gln Gly Cys Ala Ile Val
1               5                   10

<210> SEQ ID NO 44
<211> LENGTH: 26
<212> TYPE: PRT
<213> ORGANISM: Acinetobacter sp.

<400> SEQUENCE: 44

Tyr Ser Ser Gly Asp Val Ile Gly Phe Asp Ala Gly Asp Glu Ala His
1               5                   10                  15
Arg Cys Met Pro Arg Ala His Phe Leu Ser
            20                  25

<210> SEQ ID NO 45
<211> LENGTH: 5
<212> TYPE: PRT
<213> ORGANISM: Acinetobacter sp.

<400> SEQUENCE: 45

Ile Lys Phe Ala Phe
1               5

<210> SEQ ID NO 46
<211> LENGTH: 8

```
<212> TYPE: PRT
<213> ORGANISM: Acinetobacter sp.

<400> SEQUENCE: 46

Ser Gln Thr Thr Lys Leu Thr Leu
1               5

<210> SEQ ID NO 47
<211> LENGTH: 9
<212> TYPE: PRT
<213> ORGANISM: Acinetobacter sp.

<400> SEQUENCE: 47

Leu Pro Lys Gly Ser Leu Ser Ala Ser
1               5

<210> SEQ ID NO 48
<211> LENGTH: 9
<212> TYPE: PRT
<213> ORGANISM: Acinetobacter sp.

<400> SEQUENCE: 48

Asn Thr Cys Gly Leu Gly Thr Arg Pro
1               5

<210> SEQ ID NO 49
<211> LENGTH: 32
<212> TYPE: PRT
<213> ORGANISM: Acinetobacter sp.

<400> SEQUENCE: 49

Arg Thr His Thr Ser Pro Tyr Arg Val Lys Pro Arg Gly Phe Ile Pro
1               5                   10                  15

Asn Leu Glu Asp Arg Ile Leu Tyr Pro Val Arg Val Thr Gly Cys
            20                  25                  30

<210> SEQ ID NO 50
<211> LENGTH: 8
<212> TYPE: PRT
<213> ORGANISM: Acinetobacter sp.

<400> SEQUENCE: 50

Asn Asn Arg Arg Tyr Leu Ser Met
1               5

<210> SEQ ID NO 51
<211> LENGTH: 4
<212> TYPE: PRT
<213> ORGANISM: Acinetobacter sp.

<400> SEQUENCE: 51

Tyr Ser Arg Val
1

<210> SEQ ID NO 52
<211> LENGTH: 17
<212> TYPE: PRT
<213> ORGANISM: Acinetobacter sp.

<400> SEQUENCE: 52

Cys Trp Arg Thr Arg Val Gln Leu Pro Pro Ser Pro Pro Lys Leu Leu
1               5                   10                  15

Lys
```

```
<210> SEQ ID NO 53
<211> LENGTH: 13
<212> TYPE: PRT
<213> ORGANISM: Acinetobacter sp.
<220> FEATURE:
<221> NAME/KEY: MOD_RES
<222> LOCATION: (13)..(13)
<223> OTHER INFORMATION: Any amino acid

<400> SEQUENCE: 53

Ile Ser Arg Leu Leu Lys Trp Leu Phe Tyr Cys His Xaa
1               5                   10

<210> SEQ ID NO 54
<211> LENGTH: 7
<212> TYPE: PRT
<213> ORGANISM: Acinetobacter sp.

<400> SEQUENCE: 54

Gln Phe Phe Arg Val Val Leu
1               5

<210> SEQ ID NO 55
<211> LENGTH: 29
<212> TYPE: PRT
<213> ORGANISM: Acinetobacter sp.

<400> SEQUENCE: 55

Cys Asn Thr His Leu Gly Met Leu Leu Ala Ser Thr Leu Val Met Lys
1               5                   10                  15

Leu Ile Asp Ala Cys Arg Glu Arg Ile Phe Ser Arg Lys
            20                  25

<210> SEQ ID NO 56
<211> LENGTH: 29
<212> TYPE: PRT
<213> ORGANISM: Acinetobacter sp.

<400> SEQUENCE: 56

Asn Leu His Phe Asn Ser Arg Lys Arg Arg Asn Leu Arg Ser Ser Cys
1               5                   10                  15

Leu Arg Ala Val Cys Pro Leu Pro Arg Ile Leu Val Val
            20                  25

<210> SEQ ID NO 57
<211> LENGTH: 22
<212> TYPE: PRT
<213> ORGANISM: Acinetobacter sp.

<400> SEQUENCE: 57

Glu Pro Asp Arg Ser Ala Arg Thr Gln Val Arg Ile Glu Ser Ser Leu
1               5                   10                  15

Gly Ala Leu Tyr Gln Thr
            20

<210> SEQ ID NO 58
<211> LENGTH: 20
<212> TYPE: PRT
<213> ORGANISM: Acinetobacter sp.

<400> SEQUENCE: 58

Arg Ile Ala Ser Cys Thr Leu Phe Val Gly Ser Leu Gly Val Lys Thr
1               5                   10                  15
```

```
Ile Asp Asp Ile
            20

<210> SEQ ID NO 59
<211> LENGTH: 30
<212> TYPE: PRT
<213> ORGANISM: Acinetobacter sp.

<400> SEQUENCE: 59

Ala Cys Ser Ile Leu Glu Cys Ser Ala Gly Gly Arg Gly Phe Asn Ser
1               5                   10                  15

Arg His Leu His Gln Asn Tyr Leu Asn Lys Ser Ala Ala Tyr
            20                  25                  30

<210> SEQ ID NO 60
<211> LENGTH: 8
<212> TYPE: PRT
<213> ORGANISM: Acinetobacter sp.
<220> FEATURE:
<221> NAME/KEY: MOD_RES
<222> LOCATION: (8)..(8)
<223> OTHER INFORMATION: Any amino acid

<400> SEQUENCE: 60

Ser Gly Phe Phe Ile Val Ile Xaa
1               5

<210> SEQ ID NO 61
<211> LENGTH: 54
<212> TYPE: PRT
<213> ORGANISM: Staphylococcus aureus

<400> SEQUENCE: 61

Ser Tyr Met Cys Phe Cys Lys Leu Gln Lys Tyr Asp Leu Phe Asp Leu
1               5                   10                  15

Leu Phe Arg Gly Arg Ser Trp Ile Arg Gln Gly Ser Pro Glu Leu Ile
            20                  25                  30

Lys Arg Val Gly Gly Leu Ser Ser Ser Ser Thr His Thr Val Tyr Asn
        35                  40                  45

Asn Trp Gln Ile Lys Gln
    50

<210> SEQ ID NO 62
<211> LENGTH: 12
<212> TYPE: PRT
<213> ORGANISM: Staphylococcus aureus

<400> SEQUENCE: 62

Phe Arg Ser Ser Cys Leu Ile Ala Leu Cys Ile Ala
1               5                   10

<210> SEQ ID NO 63
<211> LENGTH: 12
<212> TYPE: PRT
<213> ORGANISM: Staphylococcus aureus

<400> SEQUENCE: 63

Gln His Phe Leu Tyr Ala Val Asn Ala Ile Gln Pro
1               5                   10

<210> SEQ ID NO 64
<211> LENGTH: 7
<212> TYPE: PRT
<213> ORGANISM: Staphylococcus aureus
```

```
<400> SEQUENCE: 64

Asp Met Leu Asn Thr Ala Val
1               5

<210> SEQ ID NO 65
<211> LENGTH: 30
<212> TYPE: PRT
<213> ORGANISM: Staphylococcus aureus

<400> SEQUENCE: 65

Ser Leu Phe Arg Arg Asn Leu Ile Lys Leu Ala Ser Cys Trp Leu Phe
1               5                   10                  15

Ile Thr Phe His Asp Ala Lys Pro Phe Asp Lys Leu His Thr
            20                  25                  30

<210> SEQ ID NO 66
<211> LENGTH: 19
<212> TYPE: PRT
<213> ORGANISM: Staphylococcus aureus

<400> SEQUENCE: 66

Lys Asp Val Tyr Gln Asp Leu Trp Thr Arg Val Gln Ile Pro Pro Ser
1               5                   10                  15

Pro Tyr Leu

<210> SEQ ID NO 67
<211> LENGTH: 15
<212> TYPE: PRT
<213> ORGANISM: Staphylococcus aureus

<400> SEQUENCE: 67

Pro Thr Thr Phe Val Asp Val Gly Phe Phe Ile Cys Phe Leu Ser
1               5                   10                  15

<210> SEQ ID NO 68
<211> LENGTH: 60
<212> TYPE: PRT
<213> ORGANISM: Staphylococcus aureus

<400> SEQUENCE: 68

Val Ile Cys Ala Phe Val Asn Tyr Lys Ser Met Ile Cys Leu Ile Tyr
1               5                   10                  15

Tyr Phe Gly Asp Val His Gly Phe Asp Arg Gly Pro Pro Ser Ser Leu
            20                  25                  30

Ser Val Ser Glu Gly Cys Leu Arg His Gln His Thr Gln Phe Ile Ile
        35                  40                  45

Thr Gly Lys Ser Asn Asn Asn Phe Ala Val Ala Ala
    50                  55                  60

<210> SEQ ID NO 69
<211> LENGTH: 23
<212> TYPE: PRT
<213> ORGANISM: Staphylococcus aureus

<400> SEQUENCE: 69

Ser His Ser Ala Ser Pro Asn Ser Ile Ser Tyr Met Leu Leu Thr Arg
1               5                   10                  15

Phe Asn Leu Asn Arg Ile Cys
            20
```

```
<210> SEQ ID NO 70
<211> LENGTH: 11
<212> TYPE: PRT
<213> ORGANISM: Staphylococcus aureus

<400> SEQUENCE: 70

Thr Leu Pro Phe Glu Val Cys Leu Glu Glu Thr
1               5                   10

<210> SEQ ID NO 71
<211> LENGTH: 56
<212> TYPE: PRT
<213> ORGANISM: Staphylococcus aureus
<220> FEATURE:
<221> NAME/KEY: MOD_RES
<222> LOCATION: (56)..(56)
<223> OTHER INFORMATION: Any amino acid

<400> SEQUENCE: 71

His His Val Gly Cys Leu Ser Leu Phe Met Met Arg Asn Leu Ser Ile
1               5                   10                  15

Asn Tyr Thr Arg Arg Lys Met Cys Ile Arg Thr Ser Gly Arg Gly Phe
            20                  25                  30

Lys Ser Arg Arg Leu His Ile Cys Ser Leu Gln Pro Leu Trp Met Trp
        35                  40                  45

Ala Phe Leu Tyr Val Phe Tyr Xaa
    50                  55

<210> SEQ ID NO 72
<211> LENGTH: 5
<212> TYPE: PRT
<213> ORGANISM: Staphylococcus aureus

<400> SEQUENCE: 72

Leu Tyr Val Leu Leu
1               5

<210> SEQ ID NO 73
<211> LENGTH: 4
<212> TYPE: PRT
<213> ORGANISM: Staphylococcus aureus

<400> SEQUENCE: 73

Ile Thr Lys Val
1

<210> SEQ ID NO 74
<211> LENGTH: 17
<212> TYPE: PRT
<213> ORGANISM: Staphylococcus aureus

<400> SEQUENCE: 74

Phe Ile Ile Ser Gly Thr Phe Met Asp Ser Thr Gly Val Pro Arg Ala
1               5                   10                  15

His

<210> SEQ ID NO 75
<211> LENGTH: 14
<212> TYPE: PRT
<213> ORGANISM: Staphylococcus aureus

<400> SEQUENCE: 75

Ala Cys Arg Arg Val Val Phe Val Ile Asn Thr His Ser Leu
1               5                   10
```

<210> SEQ ID NO 76
<211> LENGTH: 9
<212> TYPE: PRT
<213> ORGANISM: Staphylococcus aureus

<400> SEQUENCE: 76

Leu Ala Asn Gln Thr Ile Ile Ser Gln
1               5

<210> SEQ ID NO 77
<211> LENGTH: 16
<212> TYPE: PRT
<213> ORGANISM: Staphylococcus aureus

<400> SEQUENCE: 77

Leu Pro Asn Arg Thr Leu His Arg Leu Thr Ala Phe Pro Ile Cys Cys
1               5                   10                  15

<210> SEQ ID NO 78
<211> LENGTH: 17
<212> TYPE: PRT
<213> ORGANISM: Staphylococcus aureus

<400> SEQUENCE: 78

Arg Asp Ser Thr Leu Ile Gly Tyr Ala Lys His Cys Arg Leu Lys Ser
1               5                   10                  15

Val

<210> SEQ ID NO 79
<211> LENGTH: 16
<212> TYPE: PRT
<213> ORGANISM: Staphylococcus aureus

<400> SEQUENCE: 79

Lys Lys Leu Asn Gln Ala Ser Ile Met Leu Val Val Tyr His Phe Ser
1               5                   10                  15

<210> SEQ ID NO 80
<211> LENGTH: 5
<212> TYPE: PRT
<213> ORGANISM: Staphylococcus aureus

<400> SEQUENCE: 80

Cys Glu Thr Phe Arg
1               5

<210> SEQ ID NO 81
<211> LENGTH: 39
<212> TYPE: PRT
<213> ORGANISM: Staphylococcus aureus

<400> SEQUENCE: 81

Thr Thr His Val Glu Arg Cys Val Ser Gly Pro Leu Asp Ala Gly Ser
1               5                   10                  15

Asn Pro Ala Val Ser Ile Phe Val Ala Tyr Asn Leu Cys Gly Cys Gly
            20                  25                  30

Leu Phe Tyr Met Phe Phe Ile
            35

<210> SEQ ID NO 82
<211> LENGTH: 29
<212> TYPE: PRT

```
<213> ORGANISM: Pseudomonas aeruginosa

<400> SEQUENCE: 82

Trp Thr Leu Ala Ala Leu Cys Arg Arg Leu Val Val Asp Leu Ser Arg
1               5                   10                  15

Phe Trp Gly Arg Leu Gly Phe Asp Ala Gly Asn Lys Thr
            20                  25

<210> SEQ ID NO 83
<211> LENGTH: 17
<212> TYPE: PRT
<213> ORGANISM: Pseudomonas aeruginosa

<400> SEQUENCE: 83

Gly Ala Cys Arg Ala Gly Ser Arg Thr Arg Lys Phe Ala Ala Ala Asn
1               5                   10                  15

Leu

<210> SEQ ID NO 84
<211> LENGTH: 8
<212> TYPE: PRT
<213> ORGANISM: Pseudomonas aeruginosa

<400> SEQUENCE: 84

Leu Pro Thr Thr Thr Thr Thr Leu
1               5

<210> SEQ ID NO 85
<211> LENGTH: 8
<212> TYPE: PRT
<213> ORGANISM: Pseudomonas aeruginosa

<400> SEQUENCE: 85

Leu Leu Asn Ala Ala Ser Ser Arg
1               5

<210> SEQ ID NO 86
<211> LENGTH: 20
<212> TYPE: PRT
<213> ORGANISM: Pseudomonas aeruginosa

<400> SEQUENCE: 86

Gly Met Pro Val Asn Pro Lys Arg Leu Ser Asp Arg Thr Gly Ser Pro
1               5                   10                  15

Pro Ser Ser Leu
            20

<210> SEQ ID NO 87
<211> LENGTH: 50
<212> TYPE: PRT
<213> ORGANISM: Pseudomonas aeruginosa

<400> SEQUENCE: 87

Arg Leu Lys Leu Ile Gln Leu Ala Pro Ser Thr Leu Pro Leu Gly Arg
1               5                   10                  15

Arg Gly Val Asn Ser Val Glu Leu Ala Lys His Val Glu Pro Ile Ala
            20                  25                  30

Glu Ser Trp Arg Thr Gly Val Gln Ile Pro Ala Pro Asn Ala
        35                  40                  45

Lys Arg
    50
```

<210> SEQ ID NO 88
<211> LENGTH: 13
<212> TYPE: PRT
<213> ORGANISM: Pseudomonas aeruginosa

<400> SEQUENCE: 88

Ala Pro Asp Phe Pro Ser Glu Phe Gln Gly Leu Phe Leu
1               5                   10

<210> SEQ ID NO 89
<211> LENGTH: 20
<212> TYPE: PRT
<213> ORGANISM: Pseudomonas aeruginosa

<400> SEQUENCE: 89

Gly Leu Ser Gln Pro Phe Ala Val Asp Trp Ser Ser Thr Cys Gln Gly
1               5                   10                  15

Phe Gly Ala Asp
            20

<210> SEQ ID NO 90
<211> LENGTH: 48
<212> TYPE: PRT
<213> ORGANISM: Pseudomonas aeruginosa

<400> SEQUENCE: 90

Asp Ser Thr Pro Val Thr Lys Leu Glu Gly His Ala Glu Leu Val Ala
1               5                   10                  15

Glu Leu Val Asn Ser Leu Leu Gln Thr Tyr Ser Cys Gln Arg Arg Gln
            20                  25                  30

Leu Arg Ser Ser Cys Leu Met Arg Leu Ala Val Ala Arg Gly Cys Leu
        35                  40                  45

<210> SEQ ID NO 91
<211> LENGTH: 20
<212> TYPE: PRT
<213> ORGANISM: Pseudomonas aeruginosa

<400> SEQUENCE: 91

Thr Arg Asn Asp Cys Gln Ile Glu Gln Asp Arg Arg Gln Val Arg Cys
1               5                   10                  15

Arg Arg Asn Gly
            20

<210> SEQ ID NO 92
<211> LENGTH: 19
<212> TYPE: PRT
<213> ORGANISM: Pseudomonas aeruginosa

<400> SEQUENCE: 92

Asn Ser Tyr Ser Ser Leu Gln Ala Pro Cys His Ser Gly Gly Ala Glu
1               5                   10                  15

Leu Thr Gln

<210> SEQ ID NO 93
<211> LENGTH: 5
<212> TYPE: PRT
<213> ORGANISM: Pseudomonas aeruginosa

<400> SEQUENCE: 93

Ser Trp Leu Ser Met
1               5

```
<210> SEQ ID NO 94
<211> LENGTH: 33
<212> TYPE: PRT
<213> ORGANISM: Pseudomonas aeruginosa
<220> FEATURE:
<221> NAME/KEY: MOD_RES
<222> LOCATION: (33)..(33)
<223> OTHER INFORMATION: Any amino acid

<400> SEQUENCE: 94

Arg Arg Ala Gly Gly Arg Gly Phe Lys Ser Pro Arg Leu His Gln Met
1               5                   10                  15

Gln Arg Asp Lys Pro Leu Ile Phe Leu Val Asn Phe Arg Gly Phe Phe
            20                  25                  30

Xaa

<210> SEQ ID NO 95
<211> LENGTH: 7
<212> TYPE: PRT
<213> ORGANISM: Pseudomonas aeruginosa

<400> SEQUENCE: 95

Asp Ser Arg Ser Pro Leu Pro
1               5

<210> SEQ ID NO 96
<211> LENGTH: 17
<212> TYPE: PRT
<213> ORGANISM: Pseudomonas aeruginosa

<400> SEQUENCE: 96

Thr Gly Arg Arg Pro Val Lys Val Leu Gly Pro Ile Arg Ile Arg Arg
1               5                   10                  15

Arg

<210> SEQ ID NO 97
<211> LENGTH: 9
<212> TYPE: PRT
<213> ORGANISM: Pseudomonas aeruginosa

<400> SEQUENCE: 97

Gln Asn Leu Arg Gly Met Pro Ser Trp
1               5

<210> SEQ ID NO 98
<211> LENGTH: 18
<212> TYPE: PRT
<213> ORGANISM: Pseudomonas aeruginosa

<400> SEQUENCE: 98

Ile Arg Cys Cys Lys Leu Ile Val Ala Asn Asp Asp Asn Tyr Ala Leu
1               5                   10                  15

Ala Ala

<210> SEQ ID NO 99
<211> LENGTH: 14
<212> TYPE: PRT
<213> ORGANISM: Pseudomonas aeruginosa

<400> SEQUENCE: 99

Gln Ser Leu Gly Asp Ala Cys Lys Pro Glu Thr Thr Val Arg
1               5                   10
```

<210> SEQ ID NO 100
<211> LENGTH: 30
<212> TYPE: PRT
<213> ORGANISM: Pseudomonas aeruginosa

<400> SEQUENCE: 100

Asn Arg Ile Ala Ala Lys Phe Ala Val Asp Val Thr Ala Lys Thr His
1               5                   10                  15

Thr Ala Arg Ser Lys His Pro Ala Thr Arg Ala Ala Arg Ser
            20                  25                  30

<210> SEQ ID NO 101
<211> LENGTH: 5
<212> TYPE: PRT
<213> ORGANISM: Pseudomonas aeruginosa

<400> SEQUENCE: 101

Leu Ser Arg Ala Gly
1               5

<210> SEQ ID NO 102
<211> LENGTH: 27
<212> TYPE: PRT
<213> ORGANISM: Pseudomonas aeruginosa

<400> SEQUENCE: 102

Ala Cys Arg Thr Asp Ser Gly Glu Leu Ala Asp Gly Gly Ser Asn Pro
1               5                   10                  15

Pro Gly Ser Thr Lys Cys Lys Glu Ile Ser Pro
            20                  25

<210> SEQ ID NO 103
<211> LENGTH: 7
<212> TYPE: PRT
<213> ORGANISM: Pseudomonas aeruginosa
<220> FEATURE:
<221> NAME/KEY: MOD_RES
<222> LOCATION: (7)..(7)
<223> OTHER INFORMATION: Any amino acid

<400> SEQUENCE: 103

Ile Ser Gly Ala Phe Ser Xaa
1               5

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcggcgaaca aaaacgaa                                                 18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105

```
ggggatccgt cgacctgc                                                    18

<210> SEQ ID NO 106
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ctgcgcgctt taggtgcaaa tattgagcgt gtgaaaggcg aagcggcgaa caaaaacgaa       60

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ctggcggtag ccccgcgaac ggggctgcca gctctcagac gagggatcc gtcgacctgc        60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gattatctgg atatcccagc attcctgcgt aagcaagctg atgcggcgaa caaaaacgaa       60

<210> SEQ ID NO 109
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtttagcaca aagagcctcg aaacccaaat tccagtcaat tcggggatcc gtcgacctgc      60

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agtcaggatc aggtggacga tttgttggat agtcttggat ttgcggcgaa caaaaacgaa       60

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ccgcctgata tgacgtggtc acgccacatc aggcaataca aaggggatcc gtcgacctgc      60
```

<210> SEQ ID NO 112
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gtagatgata gcgaaggcgt agcagaaact aacgaagatt ttgcggcgaa caaaaacgaa        60

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aaaagggccg cagatgcgac ccttgtgtat caaacaagac gaggggatcc gtcgacctgc        60

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Ala Asn Lys Asn Glu Glu Asn Thr Asn Glu Val Phe Lys Leu Met
1               5                   10                  15

Leu Asn Ala Gly Gln Ala Asn Arg Arg Arg Val
            20                  25

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Asn Lys Asn Glu Glu Asn Thr Asn Glu Val Pro Asp Gly Met
1               5                   10                  15

Leu Asn Ala Gly Gln Ala Asn Arg Arg Arg Val
            20                  25

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Gln Tyr Arg
1

<210> SEQ ID NO 117
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 117

Arg Arg Arg Val
1

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

His Ile Ser Pro
1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Ile Cys Arg
1

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His Ala Gln Pro
1

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Ala Arg Gln
1

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Val Arg Arg
1
```

-continued

```
<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ala Gln Gln
1

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Arg Gln Leu
1

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Arg Gln Arg Gln
1               5
```

TUNABLE CONTROL OF PROTEIN DEGRADATION IN SYNTHETIC AND ENDOGENOUS BACTERIAL SYSTEMS

CROSS-REFERENCE TO RELATED APPLICATIONS

This application is a 35 U.S.C. §371 National Phase Entry Application of International Application No. PCT/US2014/025654 filed Mar. 13, 2014, which designates the U.S., and which claims benefit under 35 U.S.C. §119(e) of U.S. Provisional Application No. 61/779,547 filed Mar. 13, 2013, the contents of which are incorporated herein by reference in their entireties.

GOVERNMENT SUPPORT

This invention was made with Government Support under Contract No. OD003644 awarded by the National Institutes of Health, and Contract No. N00014-11-1-0725 awarded by the Office of Naval Research. The Government has certain rights in the invention

SEQUENCE LISTING

The instant application contains a Sequence Listing which has been submitted electronically in ASCII format and is hereby incorporated by reference in its entirety. Said ASCII copy, created on Feb. 28, 2017, is named 701586-075802_US_UPDATED_SL.txt and is 41,110 bytes in size.

BACKGROUND

Endogenous targeted protein degradation in bacteria occurs in part through the tmRNA system which uses the small peptide ssrA to direct proteins to the endogenous ClpXP and ClpAP proteases for rapid degradation[6,7]. Biologists use variants of the *E. coli* ssrA tag (ec-ssrA) to modify the degradation rate of attached proteins in bacteria[8] and recently in eukaryotes[9], but these tags do not provide adjustable control of degradation in bacteria because the dominant ClpXP protease is constitutively expressed and cannot be easily regulated due to its integral role in many cellular processes[10]. Davis et al.[11] used modified ec-ssrA tags and a split SspB adaptor to enable inducible degradation in this system, but the technique requires genomic disruption of the tmRNA system and is incompatible with existing genetic constructs that use ec-ssrA-mediated degradation. Recent eukaryotic degradation systems that enable small-molecule induced degradation rely on endogenous degradation machinery not present in bacteria[12-14].

SUMMARY

Tunable control of protein degradation in bacteria is one means of expanding the genetic tool set available to develop synthetic gene circuits and probe natural cellular systems. The methods and compositions described herein relate, in part, to the generation of a synthetic degradation system in *E. coli* and *Lactococcus lactis* that provides tunable control of the protein level of targeted genes by using components of the *Mesoplasma florum* tmRNA system. Provided herein are degradation tag variants that permit independent control of both the initial level and inducible degradation rate of attached proteins. Such degradation tag variants can be used in synthetic circuit development and exogenous control of core bacterial processes, including, for example, peptidoglycan biosynthesis, cell division and chemotactic motility. In addition, the synthetic degradation systems described herein are facile and modular, requiring only a small peptide tag and a single protease gene, do not require disruption of host systems to function, and can be used in other bacterial species with minimal modification. The synthetic degradation systems can be used in both Gram negative (e.g., *E. coli*) and Gram-positive (e.g., *L. lactis*) bacteria. Also provided herein are codon-optimized versions of such proteases that can be genomically integrated into e.g., *E. coli*. Such integrated proteases provide much stronger and faster inducible degradation of the protein targets and are contemplated herein for use in an industrial or commercial setting. The genomically integrated proteases have the added advantage of lacking a need for an antibiotic or other selection mechanism to maintain a plasmid and are therefore ideal for industrial or commercial use.

One aspect provided herein relates to a composition comprising a modified protein degradation tag derived from a *Mesoplasma florum* degradation tag, wherein the modified degradation tag comprises altered degradation dynamics compared to the unmodified *Mesoplasma florum* degradation tag.

In one embodiment of this aspect and all other aspects described herein, the *Mesoplasma florum* degradation tag is mf-ssrA (SEQ ID NO:27).

In another embodiment of this aspect and all other aspects described herein, the modified protein degradation tag is degraded by an mf-Lon protease or a homolog thereof from a member of the *Mycoplasma* family (e.g., *Mycoplasma pneumoniae, Mycoplasma genitalium, Mycoplasma pulmonis, Mycoplasma, synoviae, Mycoplasma penetrans, Mycoplasma fermentans*, etc).

In another embodiment of this aspect and all other aspects described herein, wherein the modified protein degradation tag has increased specificity to degradation by mf-Lon or a homolog thereof than the unmodified degradation tag.

In another embodiment of this aspect and all other aspects described herein, wherein the modified protein degradation tag has decreased sensitivity to degradation by endogenous bacterial proteases than the unmodified degradation tag. In certain embodiments, the endogenous bacterial protease is from a Gram-positive or Gram-negative bacterium. In one embodiment, the endogenous bacterial protease is an *E. coli* protease. In another embodiment, the endogenous bacterial protease is a *L. lactis* protease.

In one embodiment of this aspect and all other aspects described herein, wherein the modified protein degradation tag has increased sensitivity to degradation by endogenous bacterial proteases than the unmodified degradation tag. In certain embodiments, the endogenous bacterial protease is from a Gram-positive or Gram-negative bacterium. In one embodiment, the endogenous bacteria protease is an *E. coli* protease or a *L. lactis* protease.

In another embodiment of this aspect and all other aspects described herein, wherein the modified protein degradation tag has decreased sensitivity to degradation by mf-Lon protease than the unmodified degradation tag.

In one embodiment of this aspect and all other aspects described herein, wherein the modified protein degradation tag has increased specificity to degradation by an mf-Lon protease or a homolog thereof than the unmodified degradation tag.

In another embodiment of this aspect and all other aspects described herein, wherein the modified protein degradation tag is not degraded by ClpXP or a bacterial Lon protease (e.g., *E. coli* or *L. lactis* Lon protease).

In another embodiment of this aspect and all other aspects described herein, the modified protein degradation tag comprises a mutation(s) in amino acid residues 24-27 compared to the unmodified degradation tag. Alternatively, the modified protein degradation tag comprises a mutation(s) in one or more of amino acid residues 1-13. In another embodiment, the modified protein degradation tag comprises a mutation(s) in one or more of amino acids 13-15 of the protein degradation tag (e.g., amino acids 13-15 of mf-ssrA (SEQ ID NO:27)).

In another embodiment of this aspect and all other aspects described herein, the mutation(s) comprise one or more arginine and/or glutamine residues not present in the unmodified degradation tag.

In another embodiment of this aspect and all other aspects described herein, the modified protein degradation tag is selected from the sequences in Table 7, Table 8 or SEQ ID NOs: 1-26.

Another aspect provided herein relates to a system for tunable expression of a target protein in a cell, the system comprising: (a) a modified protein degradation tag fused to a target protein, wherein the modified degradation tag is derived from a *Mesoplasma florum* degradation tag and comprises altered degradation dynamics compared to the unmodified *Mesoplasma florum* degradation tag, and (b) a protease capable of degrading the modified protein degradation tag that is not expressed constitutively by the bacterial cell in which the system is to be expressed, wherein introduction of the modified degradation tag fusion protein of (a) and the protease of (b) permits tunable expression of the target protein in the bacterial cell.

In one embodiment of this aspect and all other aspects described herein, the protease comprises mf-Lon or a variant or homolog thereof.

Another aspect provided herein relates to a system for tunable expression of a target protein in a bacterial cell, the system comprising: (a) a protein degradation tag fused to a target protein, and (b) an exogenous *Mesoplasma* Lon protease capable of degrading the tagged protein. The protein degradation tag is at least 10 amino acids in length, and comprises the amino acid sequence PTF and/or the amino acid sequence YAFA (SEQ ID NO: 29), each of which may optionally have one or more amino acid substitutions to provide tunable degradation rates. For example, the sequence PTF may be positioned within amino acids 10 to 20, numbered according to SEQ ID NO: 1, and in some embodiments is positioned within amino acids 12 to 18 of the tag. The sequence PTF may be position at about amino acids 13 to 15 of the degradation tag. Alternatively, the sequence may contain one, two, or three amino acid substitutions altering the degradation rates. Exemplary sequences replacing the sequence PTF and providing reduced degradation rates are RAI, APN, PDS, QPT, AQP, PSP, ERA, PDG, FKL, and WLG. Each of these sequences may likewise have one or two amino acid substitutions providing additional degradation rates. In these or other embodiments, the sequence YAFA (SEQ ID NO: 29) is positioned within amino acids 18 to 30 of the degradation tag (the degradation tag can be less than 50 or less than 30 amino acids in some embodiments), and in some embodiments the sequence YAFA (SEQ ID NO: 29) is positioned within amino acids 22 to 28, such as at amino acids 24 to 27 (numbered according to SEQ ID NO:1). The sequence YAFA (SEQ ID NO: 29) may include one or more amino acid substitutions to thereby alter the degradation rate of the tagged protein, and in some embodiments the one or more substitution leads to a higher degradation rate. Exemplary sequences replacing YAFA (SEQ ID NO: 29) are described herein as SEQ ID NOS: 2-17, and such sequences may be further modified to increase the degradation rate. Some non-limiting examples of sequences replacing YAFA (SEQ ID NO: 29) include RLQL (SEQ ID NO: 30), YLSQ (SEQ ID NO: 31), RRRV (SEQ ID NO: 32), HAQP (SEQ ID NO: 33), RARQ (SEQ ID NO: 34), and ICRL (SEQ ID NO: 35). In some embodiments the modifications to the sequence YAFA (SEQ ID NO: 29) include one or more acidic or basic residues. The remaining portions of the tag (e.g., amino acids 1 to 12 and 16 to 23 numbered according to SEQ ID NO:1) are less critical for tuning the degradation rate, but in some embodiments have the sequence as set forth in SEQ ID NO:1, with one or more amino acid substitutions, deletions, or insertions that allow for the desired degradation rate. The *Mesoplasma* Lon protease that is co-expressed in the bacterial cell (e.g., Gram-negative (*E. coli*) or Gram-positive (*L. lactis*) bacterium) can have at least 70% identity to SEQ ID NO: 28, or in other embodiments, at least 80%, at least 90%, at least 95%, or at least 98% identity to SEQ ID NO: 28.

```
                            (SEQ ID NO. 28; Genbank Accession No: YP_053647.1)
  1 mskkiklpif girgsfivpg ikenlevgrk ntlasvnyai knsnnqmiai pqidasvekp 61 efsdlhefgi lidfevikew kdnsltistn piqrckvisf fenedqvpya eveliesind 121 fsdeelkeli ekisdaiktk aslvtkqikq lisgesddls lafdsimfkl apskiltnpe 181 yitspslktr wsiiekiifa edgiitrnae sidaarqkne ieqelnhklk ekmdkqqkey 241 ylrekmriik delededdsd dsslekyker lakepfpeev krkimasikr vealqsgtpe 301 wnteknyidw mmsipwweet edltdlkyak kildkhhygm kkvkeriiey lavktktksl 361 kapiitivgp pgvgktslak siaeavgknf vkvslggvkd eseirghrkt yvgsmpgrii 421 qtmkrakvkn plflldeidk masdhrgdpa samlevldpe qnkefsdhyi eepydlsqvm 481 fiatanyped ipealydrme iinlssytei ekvkiagdyl vpkaieqhel tseeisfteg 541 aineiikyyt reagvrqler hinsiirkyi vknlngemdk ividekqvnd llgkrifdht 601 ekqeesqigv vtglaytqfg gdilpievsl ypgkgnlilt gklgevmkes atialtyvks 661 nfekfgvdkk vfeendihvh vpegavpkdg psagititta lisalsdkpv skeigmtgei
```

-continued 721 tlrgnvlpig glreksisas rsglktiiip kknerdldei pdevkaklki ipaekyeevf 781 aivfktk In one embodiment of this aspect and all other aspects described herein, upon introduction into the bacterial cell, the initial expression level of the target protein tagged with a modified pdt is increased as compared to the initial expression level of the target protein when not fused to the modified degradation tag.

In another embodiment of this aspect and all other aspects described herein, the system further comprises a second degradation tag fused to the protease of (b).

In another embodiment of this aspect and all other aspects described herein, the second degradation tag is degraded by a protease constitutively expressed by the cell.

In another embodiment of this aspect and all other aspects described herein, the second degradation tag is modified to have altered degradation properties compared to a wild-type degradation tag.

In another embodiment of this aspect and all other aspects described herein, wherein the system further comprises a genetic toggle switch.

In another embodiment of this aspect and all other aspects described herein, the genetic toggle switch is based on reciprocal transcriptional repression.

In another embodiment of this aspect and all other aspects described herein, the target protein is involved in cell wall biosynthesis, cell division, metabolism (e.g., metabolism of five or six carbon sugars, kreb's cycle, or aerobic respiration), and/or chemotactic motility.

Another aspect described herein relates to a bacterial screening assay comprising: a bacterial cell expressing (a) a modified protein degradation tag fused to a target protein, wherein the modified degradation tag is derived from a *Mesoplasma florum* degradation tag and comprises altered degradation dynamics compared to the unmodified *Mesoplasma florum* degradation tag, and (b) a protease capable of degrading the modified protein degradation tag that is not expressed constitutively by the bacterial cell.

In one embodiment of this aspect and all other aspects described herein, the initial expression level of the target protein is increased compared to the initial expression level of the target protein alone or when fused to an unmodified protein degradation tag.

In another embodiment of this aspect and all other aspects described herein, the bacterial cell is a Gram-positive or Gram-negative bacterial cell. In one embodiment of this aspect and all other aspects described herein, the Gram-positive bacterial cell is an *L. lactis* cell. In another embodiment of this aspect and all other aspects described herein, the Gram-negative bacterial cell is an *E. coli* cell.

In another embodiment of this aspect and all other aspects described herein, wherein the assay further comprises a second degradation tag fused to the protease of (b).

In another embodiment of this aspect and all other aspects described herein, the second degradation tag is degraded by a protease constitutively expressed by the cell.

In another embodiment of this aspect and all other aspects described herein, the second degradation tag is modified to have altered degradation properties compared to a wild-type degradation tag.

In another embodiment of this aspect and all other aspects described herein, the assay further comprises a genetic toggle switch.

In another embodiment of this aspect and all other aspects described herein, the genetic toggle switch is based on reciprocal transcriptional repression.

In another embodiment of this aspect and all other aspects described herein, the target protein is involved in cell wall biosynthesis, cell division, metabolism (e.g., metabolism of five or six carbon sugars, kreb's cycle, or aerobic respiration), and/or chemotactic motility.

In another embodiment of this aspect and all other aspects described herein, the target protein is a candidate drug target.

In another embodiment of this aspect and all other aspects described herein, the target protein is a candidate antibiotic target.

In another embodiment of this aspect and all other aspects described herein, the assay further comprises an output product.

In another embodiment of this aspect and all other aspects described herein, the output product comprises a reporter molecule, an enzyme, or a selection marker.

In another embodiment of this aspect and all other aspects described herein, the reporter molecule comprises a measurable signal of fluorescence, color or luminescence.

Also provided herein, in another aspect, are methods relating to the identification of a candidate antibiotic target in a bacterial cell, the method(s) comprising: (a) expressing in a bacterial cell, (i) a first modified protein degradation tag fused to a target protein, wherein the modified degradation tag comprises altered degradation dynamics by a protease compared to an unmodified degradation tag, (ii) a protease capable of degrading the modified protein degradation tag of (a), wherein the protease is not constitutively expressed by the bacterial cell, (b) measuring an output product, wherein a decrease in a positive output product indicates that the target protein is a candidate antibiotic target, or wherein an increase in a negative output product indicates that the target protein is a candidate antibiotic target.

In certain embodiments of this aspect and all other aspects described herein, the bacterial cell is a Gram-positive or Gram-negative bacterial cell. In one embodiment of this aspect and all other aspects described herein, the Gram-positive bacterial cell is an *L. lactis* cell. In another embodiment of this aspect and all other aspects described herein, the Gram-negative bacterial cell is an *E. coli* cell.

Also provided herein, in another aspect, are kits comprising: (a) a vector encoding a modified protein degradation tag and a multiple cloning site, wherein the modified degradation tag is derived from a *Mesoplasma florum* degradation tag and comprises altered degradation dynamics compared to the unmodified *Mesoplasma florum* degradation tag, and (b) optionally, a vector encoding a protease capable of degrading the modified protein degradation tag, and (c) instructions for use in cells that do not express the protease of (b).

Another aspect provided herein relates to a method for using pdt or modified pdts to simultaneously tag multiple endogenous proteins, which can permit coordinated control of multiple cellular pathways using a protease as described herein.

BRIEF DESCRIPTION OF THE DRAWINGS

(FIG. 1A) Schematic of the tunable protein degradation system where induction of mf-lon by anhydrotetracycline (aTc) allows the protease to degrade constitutively expressed GFP in a pdt-dependent manner. Targeted mutagenesis of two regions of pdt-identified tags with altered recognition by mf-Lon (letters) or endogenous E. coli proteases (numbers). (FIG. 1B) GFP-pdt expressed from the constitutive $P_{lacIq}$ promoter showed increased degradation in the transition from logarithmic to stationary phase growth. GFP fluorescence and optical density (600 nm) were measured by flow cytometry and microplate reader. (FIG. 1C) Panel of pdt number variants that show altered degradation by endogenous E. coli proteases. Fluorescence was measured 10 h after aTc induction of cells in mid-log growth. The fluorescence units are arbitrary with untagged GFP set to 100, and the error bars represent the mean±standard deviation (SD) of three biological replicates.

(FIGS. 2A-2B) Flow cytometry measurements of GFP degradation following mf-Lon induction with 50 ng/ml aTc. Data show the geometric mean fluorescence of >10,000 cells as a percentage of the non-induced control for each pdt variant, and the error bars represent the mean±standard deviation (SD) of three biological replicates. (FIG. 2A) PDT number variants maintain nearly identical mf-Lon-mediated degradation dynamics. (FIG. 2B) PDT letter variants display altered mf-Lon-mediated degradation rates. (FIG. 2C) Panel of hybrid pdt variants. Strains expressing the indicated GFP-pdt fusion were measured by plate fluorimetry 10 h after aTc induction. Fluorescence units in a log scale are arbitrary with untagged GFP set to 100. (FIG. 2D) Control of GFP-pdt#5 degradation using transcriptional and post-translational control of mf-Lon. Fusion of E. coli ssrA tag variants (ec-LAA, ec-AAV, ec-ASV) to mf-Lon provides control of mf-Lon activity across a range of transcriptional induction levels. Inactivation of mf-Lon protease activity (S692A) blocks GFP degradation. Data were collected 10 h after aTc induction using GFP-pdt#5 as the degradation target.

(FIG. 3A) Schematic of the synthetic toggle switch in which reciprocal transcriptional repression by TetR and LacI form a bistable circuit. GFP and mCherry serve as fluorescent reporters for the LacI+ and TetR+ toggle states, respectively. Addition of a pdt tag to LacI enables a protease-driven switch to the mCherry+ state. (FIG. 3B) Flow cytometry scatter plots show GFP and mCherry fluorescence 0, 4, and 8 h after mf-Lon expression from the inducible promoter $P_{BAD}$. Degradation of LacI-pdt#5 causes the toggle to switch from the GFP+ state to the mCherry+ state by 8 h while the untagged toggle remains in the GFP+ state. Magenta lines indicate the gate parameters used to define the GFP+ and mCherry+ states: cells bounded in the lower left quadrant are considered negative for both GFP and mCherry. (FIG. 3C) The percentage of cells in the mCherry+ state following mf-Lon induction. Data collected by flow cytometry were measured using the parameters shown in (b), and error bars represent the mean±standard deviation (SD) of three biological replicates. See FIG. 7 for data showing that non-induced strains did not shift to mCherry+.

(FIG. 4A) Schematic of our recombineering method for genomic insertion of pdt variants, adapted from Datsenko and Wanner[23]. Red recombinase-assisted insertion of a transformed PCR product containing the desired pdt variant is followed by Flp recombinase-mediated excision of the accompanying kanamycin cassette using the surrounding FRT sites. The resulting insertion contains the pdt variant and an 83 bp scar including the remaining FRT site. (FIG. 4B) Growth of strains following protease-driven depletion of MurA. Protease induction during early-log phase growth (arrow) caused cells containing murA-pdt#1 to lyse after ~3 h, as measured by optical density (600 nm). Cells containing the weakened variants pdt#1A and pdt#1B show a delayed response. Error bars represent the mean±standard deviation (SD) of six biological replicates. See FIG. 9A for data showing wild-type growth of non-induced cells. (FIG. 4C) DIC microscopy images of bacteria after depletion of FtsZ. Bacteria with ftsZ-pdt#10 form filaments, while untagged wild-type bacteria maintain normal length. The fluorescence micrograph overlay showing constitutive GFP expression serves as a visual aid. (FIG. 4D) Disk diffusion assay on a chemotactic motility plate showing inducible CheZ degradation. Cells were stabbed into the chemotaxis plate following addition of 250 ng aTc to the center disk and were imaged after 18 h at 30°.

(FIG. 9A) Growth of murA-pdt strains in the absence of mf-Lon induction. Strains containing the indicated pdt variants display nearly identical growth rates to the wild-type strain as measured by optical density (600 nm). Data were collected simultaneously with the experimental data shown in FIG. 4B. (FIG. 9B) The growth rate of the ftsZ-pdt#10 strain in the absence of mf-Lon induction was nearly identical to wild-type cells. (FIG. 9C) Disk diffusion assay on a control chemotaxis plate shows that the cheZ-pdt#10 strain exhibits normal chemotactic behavior when no aTc is added to the center disk. This provides further evidence that the chemotactic deficiency of the cheZ-pdt#10 strain in FIG. 4C was specifically due to aTc induction of mf-Lon. Cells were stabbed into the chemotaxis plate following addition of 5 µl water to the center disk and were imaged after 18 h at 30° C.

FIG. 11A shows a panel of pdt number variants that show altered steady-state levels. Fluorescence was measured 6 hours after ATc induction of cells in exponential growth. As an experimental control, the pdt#3 variant was tested in a strain that did not contain the mf-Lon expression cassette (#3 con). Fluorescence units are arbitrary, with untagged GFP set to 100. FIGS. 11B-C show flow cytometry measurements of GFP degradation following mf-Lon induction with 50 ng/ml ATc. Data show the geometric mean fluorescence of at least 5,000 cells as a percentage of the non-induced control for each pdt variant. FIG. 11B shows pdt number variants maintain similar mf-Lon-mediated degradation dynamics. FIG. 11C shows that pdt letter variants display altered mf-Lon-mediated degradation rates. FIG. 11D shows a panel of hybrid pdt variants. Strains expressing the indicated GFP-pdt fusion were measured by flow cytometry 6 hours after ATc induction. Fluorescence units are arbitrary with untagged GFP set to 100. The error bars in all figures show the standard deviation of three biological replicates.

FIG. 12A shows a comparative analysis of pdt-mediated degradation of mCherry and GFP. Pdt letter variants were fused to GFP and mCherry, and the percent fluorescence remaining after mf-Lon induction (50 ng/ml ATc for 6 h) is shown. Fluorescent data were collected by flow cytometry, and the pdt variants shown are pdt#3, #3A, #3B, #3C, #3D, #3E, listed in order of increasing percent fluorescence. The best-fit line is y=1.09x−0.01 with an $R^2$ value of 0.99. FIG. 12B shows transcription and post-translation-based control of mf-Lon-mediated pdt degradation. Inducible transcription provides control of mf-Lon-mediated degradation of GFP-pdt#3 across a range of ATc induction levels. Fusion of the E. coli ssrA tag variants ec-AAV and ec-ASV to mf-Lon shift the GFP degradation profile, and inactivation of mf-Lon protease activity (S692A) blocks GFP degradation. Data were collected 6 hours after ATc induction using GFP-pdt#3 as the degradation target. FIG. 12C shows pdt-dependent degradation of mCherry in L. lactis. Nisin induced mf-Lon expression in L. lactis causes pdt-dependent mCherry degradation. Data show the geometric mean fluorescence as a percent of the fluorescence of uninduced cells. Nisin induction was 3 ng/ml. FIG. 12D shows a comparative analysis of pdt letter variants in E. coli and L. lactis. Pdt letter variants were fused to mCherry, and the percent fluorescence remaining after mf-Lon induction is shown (6 hour induction, E. coli: 50 ng/ml ATc and L. lactis: 3 ng/ml nisin). Fluorescent data were collected by flow cytometry, and the pdt variants shown are pdt#3, #3A, #3B, #3C, #3D, #3E, listed in order of increasing percent fluorescence. The best-fit line is y=1.79x+0.11 with an $R^2$ value of 0.92. For all figures, error bars show the standard deviation of three biological replicates.

FIG. 13A shows the growth of strains following protease-driven depletion of MurA. Protease induction during early exponential phase growth (arrow) causes cells containing murA-pdt#1 to lyse within 1 hour, as measured by optical density (OD600). Cells containing the weakened pdt letter variants show a delayed response. Error bars show the standard deviation of six biological replicates. FIG. 13B shows DIC-fluorescence overlay images of cells after ATc induction for 3 hours. Cells containing ftsZ-pdt#5 form filaments while untagged wild-type bacteria maintain normal length. The fluorescence micrograph overlay showing constitutive GFP expression serves as a visual aid. FIG. 13C shows a disk diffusion assay on a chemotactic motility plate shows loss of chemotactic motility due to pdt dependent CheZ degradation. Cells were stabbed into the chemotaxis plate following addition of 250 ng ATc to the center disk. FIG. 13D shows that cells containing murA-pdt#1D show increased sensitivity to fosfomycin upon simultaneous induction with 4 ng/ml ATc (induced). OD600 measurements were taken 6 hours after ATc and fosfomycin treatment and are presented as a percent of the OD600 of cells not exposed to fosfomycin (untreated). FIG. 13E shows data indicating that pdt-dependent degradation of RecA causes hypersensitivity to the quinolone norfloxacin that matches the known hypersensitivity of a recA deletion strain (ΔrecA). Where indicated, cells were induced with 50 ng/ml ATc for 2 hours before treatment with norfloxacin (25 ng/ml) for 2 hours. Survival was measured by colony forming units (CFU) and is presented as a percent of CFUs measured immediately before norfloxacin treatment.

FIG. 14A shows GFP and GFP-pdt levels in E. coli strains containing an in-frame deletion of the indicated E. coli protease gene. GFP, GFP-pdt, and GFP-pdt#3 were constitutively expressed from the PlacIq promoter, and fluorescence was measured by flow cytometry. Optical density of exponential and stationary phase cells was approximately 0.3 and 1.6 respectively. Fluorescence units are arbitrary, with untagged GFP set to 100 for both the exponential phase and stationary phase conditions. Error bars show the standard deviation of three biological replicates.

FIG. 16A shows pdt number variant correlation between mCherry and GFP in *E. coli*. The pdt variants, listed in order of increasing percent mCherry fluorescence, are pdt, pdt#2, pdt#3, pdt#5. The simple linear regression line is y=1.26x−0.07 with an $R^2$ value of 0.95. FIG. 16B shows pdt number variant correlation between *L. lactis* and *E. coli*. The pdt number variants, listed in order of increasing percent fluorescence in *E. coli*, are pdt#1, pdt, pdt#2, pdt#3, pdt#5. The simple linear regression line is y=0.60x+0.17 with an $R^2$ value of 0.61. Error bars in both figures show the standard deviation of three biological replicates.

DETAILED DESCRIPTION

Figure 1A:
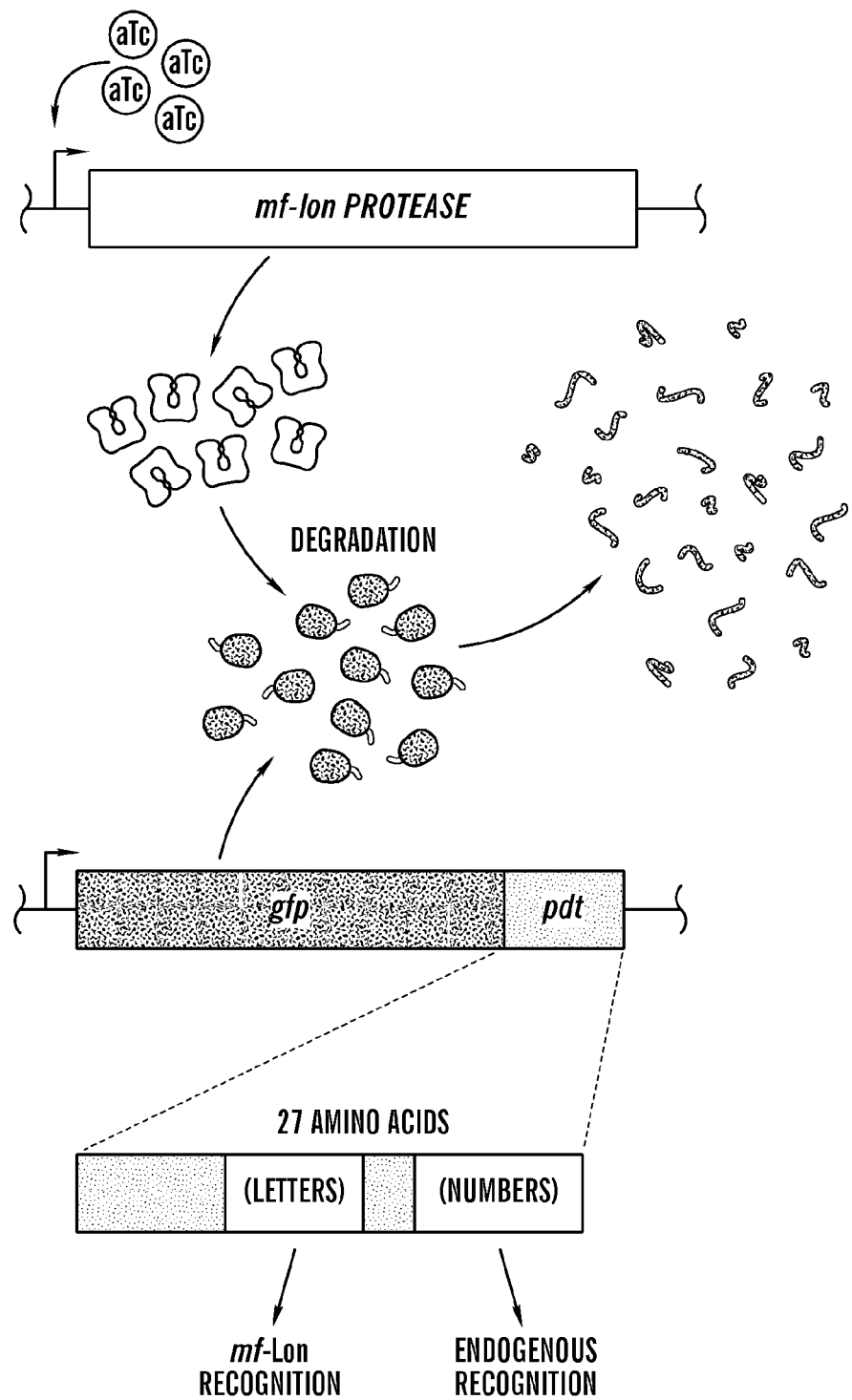
FIGS. 1A-1C demonstrate protein degradation tag characterization.

Exogenous control of protein biosynthesis through transcriptional and translational regulation is well established[1-5], but robust and tunable control of protein degradation in bacterial systems is not as developed. As described herein, synthetic degradation components and systems that do not rely on host cell degradation systems and can function in a wide range of bacteria were developed (e.g., gram-positive and gram-negative bacteria). Specifically, as described herein, tmRNA components of the Gram-positive bacterium *Mesoplasma florum* were used to create synthetic degradation components and systems and demonstrate their functionality in *E. coli* and *L. lactis*. Previous work by Gur and Sauer[15] found that the *M. florum* ssrA tag (mf-ssrA) is degraded by its endogenous Lon protease (mf-Lon), but not by ClpXP or the *E. coli* Lon homolog. Furthermore, mf-Lon does not recognize or degrade ec-ssrA, providing a protease and cognate degradation tag with orthogonal functionality.

A fluorescence based assay platform for inducible protein degradation in bacteria (e.g., *E. coli* and *L. lactis*) was produced that incorporates mf-ssrA and mf-Lon, and takes advantage of the size and complexity of the 27 amino acid mf-ssrA tag to engineer variants, termed herein "protein degradation tags (pdts)," with altered degradation dynamics. Distinct regions of the degradation tag were targeted for mutations that affect recognition by either mf-Lon or endogenous bacterial proteases, and the resulting tag variants were combined to create hybrid tags with predictable and independent control of both the initial level and the inducible degradation rate of attached proteins. To further validate the systems, hybrid tags were incorporated into synthetic genetic systems to enable protease-based switching of a genetic toggle switch and then used genomic tag insertions to control endogenous bacterial processes, without disrupting their existing regulatory architecture. Accordingly, these *facile* and tunable protein degradation components and systems provide several advantages over current bacterial degradation systems, and expand the repertoire of regulatory mechanisms available to biologists and engineers.

Definitions

As used herein, the term "protein degradation tags (pdts)" refers to a small amino acid sequence that, when fused to a target protein, marks the protein for degradation by a cognate protease in a bacterial cell. Examples of pdt and cognate protease pairs include, but are not limited to *E. coli* ssrA (ec-ssrA)/*E. coli* Lon (ec-Lon), and *Mesoplasma florum* ssrA (mf-ssrA)/*Mesoplasma florum* Lon (mf-Lon).

As used herein, the term "modified protein degradation tag" refers to a degradation tag that has been modified to have altered expression and/or degradation dynamics compared to the unmodified degradation tag.

As used herein the term "target protein" refers to any protein that is desired to be expressed in the cell. In some embodiments, the "target protein" is a "candidate drug target" (e.g., a candidate antibiotic target." Such candidate drug targets can be identified by expressing the target protein fused to a modified pdt in a cell to achieve the desired level of expression and/or rate of degradation to determine the effect of expression levels on a cellular process e.g., bacterial cell wall biosynthesis, cell division and motility. The candidate drug targets can also be tested for expression levels and rates of degradation in the presence of a drug.

As used herein, the term "altered degradation dynamics" refers to an increase or decrease in the rate of recognition or degradation of the modified pdt and the target protein by the cognate protease compared to the rate of recognition or degradation of the unmodified pdt and the target protein. For example, a modified pdt can be degraded by its cognate protease at an increased rate compared to its unmodified counterpart. Alternatively, in some embodiments, the modified pdt is degraded at a decreased, i.e., slower rate by its cognate protease than the unmodified degradation tag from which it is derived. Further, a modified pdt can also be used to modify the initial expression level of the target protein in a cell, which is referred to herein as "altered expression" or "altered initial expression levels". It is contemplated herein that such modified pdts can be used to increase or decrease the initial expression level of the target protein as compared to the same protein fused to the unmodified pdt counterpart.

The terms "increase", or "enhance" or "activate" are all used herein to generally mean an increase by a statistically significant amount. However, for the avoidance of any doubt, the terms "increased", "increase" or "enhance" or "activate" means an increase in the amount of expression or rate of degradation of a target protein of a modified pdt fusion protein by at least about 5%, or least 10% as compared to the level of expression or rate of degradation of an unmodified pdt fusion protein, for example an increase of at least about 20%, or at least about 30%, or at least about 40%, or at least about 50%, or at least about 60%, or at least about 70%, or at least about 80%, or at least about 90% or up to and including a 100% increase or any increase between 10-100%, or at least about a 2-fold, or at least about a 3-fold, or at least about a 4-fold, or at least about a 5-fold or at least about a 10-fold increase, or any increase between 2-fold and 10-fold or greater as compared to degradation system comprising an unmodified pdt fusion protein.

Conversely, the term "decrease," "decreased," or "reduced" are all used herein to generally mean a decrease in expression level or degradation rate of a pdt fusion protein comprising a modified pdt by a statistically significant amount, for example, by at least about 5%, or least 10% as compared to the level of expression or rate of degradation of an unmodified pdt fusion protein, for example a decrease of at least about 20%, or at least about 30%, or at least about 40%, or at least about 50%, or at least about 60%, or at least about 70%, or at least about 80%, or at least about 90% or up to and including a 100% decrease or any decrease between 10-100%, or at least about a 2-fold, or at least about a 3-fold, or at least about a 4-fold, or at least about a 5-fold or at least about a 10-fold decrease, or any decrease between 2-fold and 10-fold or greater as compared to degradation system comprising an unmodified pdt fusion protein.

The term "statistically significant" or "significantly" refers to statistical significance and generally means a two standard deviation (2SD) as compared to the other value. The term refers to statistical evidence that there is a difference. The decision is often made using the p-value.

As used herein, the term "cognate protease" or "paired protease" refers to a protease that can recognize a modified pdt. as that term is used herein, and thereby degrade the target protein fused to the modified pdt. In some embodiments, it is preferred that the cognate protease is not constitutively expressed in the cell that the system is designed to be used in. This can be achieved, in part, by using a cognate protease/pdt pair from a highly divergent bacterium (such as *Mesoplasma florum* or another member of the *Mycoplasma* family) and expressing them in a cell (e.g., gram-negative bacteria such as *E. coli*, gram-positive bacteria such as *L. lactis*, or a eukaryote) that does not constitutively express a protease with the ability to recognize or degrade proteins tagged with the modified pdt from the highly divergent bacterium. Also contemplated herein is the use of ssrA tags and/or cognate proteases from the *Mycoplasma* family (e.g., *Mycoplasma pneumoniae*, *Mycoplasma genitalium*, *Mycoplasma pulmonis*, *Mycoplasma, synoviae*, *Mycoplasma penetrans*, *Mycoplasma fermentans*, etc).

As used herein, the terms "constitutively expressed" or "expressed constitutively" are used interchangeably herein and refer to a protease that is native to the cell in which the methods and systems described herein are employed and wherein the protease comprises proteolytic activity (e.g., recognition and degradation of proteins) in the cell (e.g., a basal proteolytic activity). For example, in an *E. coli* cell, ec-Lon is considered to be constitutively expressed, while mf-Lon is not. mf-Lon is considered to be "exogenously expressed" in an *E. coli* cell.

As used herein, the term "tunable expression" refers to the ability of the systems described herein to control the level of expression of a target protein in a cell. This can be achieved, for example, by selecting a modified protein degradation tag that confers specific expressional characteristics when fused to the target protein, e.g., (i) an increased or decreased initial expression level of the target protein compared to the expression of the target protein alone or fused to an unmodified pdt, or (ii) an increased or decreased rate of degradation by the cognate protease compared to the rate of degradation by the cognate protease of the target protein alone or fused to an unmodified pdt. Alternatively, the expression level of the cognate protease can be tuned to a desired level of expression (e.g., mRNA or protein) or activity level by e.g., (i) modifying the amount of the nucleic acid construct encoding the cognate protease that is introduced to the cell, (ii) controlling the expression of the cognate protease using an inducible promoter or biological circuit encoded by the nucleic acid construct, or (iii) fusing a degradation tag (or modified degradation tag) to the cognate protease that is recognized and degraded at a desired rate by a protease constitutively expressed in the cell to which the system is expressed.

As used herein, the term "capable of degrading" refers to a protease that can recognize and degrade, at least partially, a protein tagged with a pdt or modified pdt as described herein. Thus, "capable of degrading" can mean that the protein tagged with a pdt or modified pdt is degraded by at least 10% compared to the protein tagged with the pdt or modified pdt in the absence of the protease; preferably the pdt/protein or modified pdt/protein fusion is degraded by at least 20%, at least 30%, at least 40%, at least 50%, at least 60%, at least 70%, at least 80%, at least 90%, at least 95%, at least 99%, or even 100% (i.e., the mRNA or protein level of the protein tagged with a pdt or modified pdt is below standard detection levels using e.g., FACS, ELISA, fluorescence microscopy, etc). In addition, it is contemplated herein that the term "capable of degrading" refers to a rate of degradation of a protein tagged with a pdt or modified pdt, rather than by expression level alone. For example, a protease is "capable of degrading" a tagged protein even if the degradation occurs at a reduced rate, e.g., the rate of degradation of a modified pdt fusion protein is reduced by at least 10%, at least 20%, at least 30%, at least 40%, at least 50%, at least 60%, at least 70%, at least 80%, at least 90% or more compared to the rate of degradation of an unmodified pdt fusion protein or the target protein expressed in the absence of a pdt tag. Further, one of skill in the art will also appreciate that the rate of degradation of a tagged protein can be increased compared to its untagged counterpart, e.g., by at least 10%, at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold or more. Exemplary proteases capable of degrading a pdt or modified pdt as described herein include, but are not limited to, mf-Lon, or a variant or homolog thereof (e.g., a Lon protease from another member of the *Mycoplasma* family).

The term "nucleic acid construct" as used herein refers to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences may also be positioned between the two sequences. The insertion of sequences may also lead to the expression of fusion proteins, or serves as ribosome binding sites. In some embodiments, the expression construct, consisting of a linkage of promoter and nucleic acid sequence to be expressed, can exist in a vector integrated form and be inserted into a plant genome, for example by transformation.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter can be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter may comprise an inducible, constitutive or tissue-specific promoter.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of an RNA molecule but does not necessarily require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, a biological converter switch that comprises a sequence encoding a recombinase and a recombinase recognition sequence encompasses both the recombinase and a recombinase recognition sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Protein Degradation Tag Variants

As defined herein, a "degradation tag" or "protein degradation tag" is a genetic addition to the end of a nucleic acid sequence that modifies the protein that is expressed from that sequence, such that the protein undergoes e.g., faster degradation by a protease or cellular degradation mechanisms. Thus, such protein degradation tags 'mark' a protein for degradation, thereby decreasing a protein's half-life.

One of the useful aspects of degradation tags is the ability to detect and regulate gene activity in a time-sensitive manner. Typically, protein degradation tags operate through the use of protein-degrading enzymes, such as proteases, within the cell. Degradation tags can encode, for example, a sequence of about eleven amino acids at the C-terminus of a protein, wherein the sequence is normally generated in *E. coli* when a ribosome gets stuck on a broken ("truncated") mRNA. Without a normal termination codon, the ribosome can't detach from the defective mRNA. A special type of RNA known as ssrA ("small stable RNA A") or tmRNA ("transfer-messenger RNA") rescues the ribosome by adding the degradation tag followed by a stop codon. This allows the ribosome to break free and continue functioning. The tagged, incomplete protein can get degraded by the proteases ClpXP or ClpAP. Although the initial discovery of the number of amino acids encoding for an ssRA/tmRNA tag was eleven, the efficacy of mutating the last three amino acids of that system has been tested. Thus, the tags AAV, ASV, LVA, and LAA are classified by only three amino acids.

The use of protein degradation tags for inducible degradation of a target protein is limited by the presence of endogenous constitutively active proteases in bacterial cells. Researchers have aimed to solve this limitation by modifying the *E. coli* ssrA (ec-ssrA) degradation tag to modify the degradation rate of attached proteins in bacteria. The protein degradation tags as described herein are modified from degradation tags of the highly divergent Gram-positive bacteria *Mesoplasma florum*, particularly mf-ssrA, however ssrA tags from other members of the *Mycoplasma* family are also contemplated herein (e.g., ssrA tags from *Mycoplasma pneumoniae, Mycoplasma genitalium, Mycoplasma pulmonis, Mycoplasma, synoviae, Mycoplasma penetrans,* or *Mycoplasma fermentans*, etc) The genetic divergence of *M. florum* from other bacteria enables the degradation system described herein to function in a wide range of Gran-negative and Gram-positive bacteria, as well as eukaryotes. The degradation tag from *M. florum* is recognized and degraded only by its endogenous Lon protease (mf-Lon) and is not recognized or degraded by ClpXP or the *E. coli* or *L. lactis* Lon homologs. Thus, provided herein are protein degradation tags derived from mf-ssrA. In some embodiments, the protein degradation tag (pdt) comprise altered characteristics including, altered initial protein levels of a target protein, and/or altered protease-induced degradation dynamics.

In some embodiments of the aspects described herein, the protein degradation tag is a modified mf-ssrA tag. The size of the degradation tag enables targeted mutagenesis of distinct regions of the tag to generate tags with independent control of recognition by endogenous proteases and by the cognate protease mf-Lon (or a variant or homolog thereof) used in the systems described herein. Other mutations can be introduced into the mf-ssrA tag, for example, by targeted mutations, deletions or addition of other amino acids in the tag in order to affect recognition by endogenous proteases or proteases that specifically target the tag for degradation. In another embodiment, the protein degradation tag comprises a modified ssrA tag from another *Mycoplasma* species.

The unmodified mf-ssrA tag comprises the sequence:

(SEQ ID NO: 27)
```
  1 mgehvialnk kakfnyeile tweagielyg peiksirnhe aniaeafili rkkeaflina 61 nikkydyanf vkgidplrtr klllhkkein kilkrvmlek ltivplrlyl kgnyakleig 121 lgrgkkihdk retikkrdie rkemrkyky.
```

In some embodiments of the aspects described herein, the pdt tag comprises a sequence that is selected from the group consisting of sequences that encode for the peptides in Table 7 (SEQ ID NOs: 1-26) or Table 8. The inventors have found that deletion of the first 13 amino acids of mf-ssrA which completely abrogates recognition by mf-Lon, but alterations in individual amino acids in this region changes sensitivity to mf-Lon degradation. The inventors have also shown that varying amino acids 13-15 can vary specificity towards mf-Lon. Therefore, in one embodiment a mutation in amino acids 13-15 is contemplated for generating a modified pdt as described herein. Mutations within amino acids 1-13 can be used to generate a modified pdt, provided that the recognition of mf-Lon or a variant or homolog thereof is not completely abrogated. The inventors have found that tags with variants in amino acids 25-27 of mf-ssrA show increased specificity to mf-Lon because they have are modified to have decreased sensitivity to endogenous E. coli proteases, while their sensitivity to mf-Lon remains relatively unchanged. The inventors have also found that variants in amino acids 13-15 of mf-ssrA show decreased sensitivity and specificity to mf-Lon. Mutations in each of these regions are contemplated for use in generating a modified pdt as described herein.

Also contemplated herein is the use of an *E.coli* ssrA-tag sequence (e.g., ANDENYALAA (SEQ ID NO: 36)) for use with a system as described herein for the microorganisms *Pseudomonas*, *Staphylococcus*, and/or *Acinetobacter*. The sequences below are nucleotide sequences of the corresponding tmRNA genes that contain the tag sequences. They are translated in all three forward reading frames to reveal the potential peptide coding regions. The underlined region indicates the *E. coli* ssrA-tag sequence in each sequence.

```
E. coli ssrA-tag sequence: ANDENYALAA (SEQ ID NO: 36)

>914794-915261_1 Acinetobacter sp. ADP1 chromosome, complete genome
GYKLHSNESGLCYSVILIWGCYWLRRW**SS*MHAESAFSLVNKICILIVANDETYALAA

*GQFVRFLEYLWFRNPTVAHAHKSV*SQASGLYTKLRGSHLVPCSSGHWVLKQ*TISKHV

VFSSVVLADAGSTPAISTKIT*INQPITKVAFLLSF (SEQ ID NOS 37-42, respectively, in
order of appearance)

>914794-915261_2 Acinetobacter sp. ADP1 chromosome, complete genome
VINCIAIFQGCAIV*YSSGDVIGFDAGDEAHRCMPRAHFLS*IKFAF**SQTTKLTL*LP

KGSLSAS*NTCGLGTRP*RTHTSPYRVKPRGFIPNLEDRILYPVRRVTGC*NNRRYLSM*

YSRV*CWRTRVQLPPSPPKLLK*ISRLLKWLFYCHX (SEQ ID NOS 43-53, respectively, in
order of appearance)

>914794-915261_3 Acinetobacter sp. ADP1 chromosome, complete genome
L*IA*QFFRVVL*CNTHLGMLLASTLVMKLIDACRERIFSRK*NLHFNSRKRRNLRSSCL

RAVCPLPRILVV*EPDRSARTQVRIESSLGALYQT*RIASCTLFVGSLGVKTIDDI*ACS

ILECSAGGRGFNSRHLHQNYLNKSAAY*SGFFIVIX (SEQ ID NOS 54-60, respectively, in
order of appearance)

>837441-837907_1 Staphylococcus aureus subsp. aureus MSA476 chromosome,
complete genome
SYMCFCKLQKYDLFDLLFRGRSWIRQGSPELIKRVGGLSSSSTHTVYNNWQIKQ*FRSSC

LIALCIA*QHFLYAVNAIQP**DMLNTAV*SLFRRNLIKLASCWLFITFHDAKPFDKLHT

*KDVYQDLWTRVQIPPSPYL*PTTFVDVGFFICFLS (SEQ ID NOS 61-67, respectively, in
order of appearance)

>837441-837907_2 Staphylococcus aureus subsp. aureus MSSA476 chromosome,
complete genome
VICAFVNYKSMICLIYYFGDVHGFDRGPPSSLSVSEGCLRHQHTQFIITGKSNNNFAVAA

*SHSASPNSISYMLLTRFNLNRIC*TLPFEVCLEET*SS*HHVGCLSLFMMRNLSINYTR

RKMCIRTSGRGFKSRRLHICSLQPLWMWAFLYVFYX (SEQ ID NOS 68-71, respectively, in
order of appearance)

>837441-837907_3 Staphylococcus aureus subsp. aureus MSSA476 chromosome,
complete genome
LYVLL*ITKV*FV*FIISGTFMDSTGVPRAH*ACRRVVFVINTHSL**LANQTTISQ*LP

NRTLHRLTAFPICC*RDSTLIGYAKHCRLKSV*KKLNQASIMLVVYHFS*CETFR*TTHV

ERCVSGPLDAGSNPAVSIFVAYNLCGCGLFYMFFI (SEQ ID NOS 72-81, respectively, in
order of appearance)

>c901924-901466_1 Pseudomonas aeruginosa PAO1 chromosome, complete genome
WTLAALCRRLVVDLSRFWGRLGFDAGNKT*GACRAGSRTRKFAAANL*LPTTTTTL*LLN
```

-continued

```
AASSR*GMPVNPKRLSDRTGSPPSSL*T*RLKLIQLAPSTLPLGPRGVNSVELLAKHVEPI

AESWPTGVQIPPAPPNAKR*APDFPSEFQGLFL  (SEQ ID NOS 82-88, respectively, in
order of appearance)

>c901924-901466_2 Pseudomonas aeruginosa PAO1 chromosome, complete genome
GLSQPFAVDWSSTCQGFGAD*DSTPVTKLEGHAELVAELVNSLLQTYSCQRRQLRSSCLM

RLAVARGCL*TRNDCQIEQDRRQVRCRRNG*NSYSSLQAPCHSGGAELTQ*SWLSM*NR*

RRAGGRGFKSPRLHQMQRDKPLIFLVNFRGFFX  (SEQ ID NOS 89-94, respectively, in
order of appearance)

>c901924-901466_3 Pseudomonas aeruginosa PAO1 chromosome, complete genome
DSRSPLP*TGRRPVKVLGPIRIRRR*QNLRGMPSW*QNS*IRCCKLIVANDDNYALAA*C

G*QSLGDACKPETTVR*NRIAAKFAVDVTAKTHTARSKHPATRAARS*LSRAG*ACRTDS

GELADGGSNPPGSTKCKEISP*FS**ISGAFSX  (SEQ ID NOS 95-103, respectively, in
order of appearance)
```

Other useful pdt tag sequences can be developed, for example, using the fluorescence-based in vivo test platform as described herein in the Examples section.

It is further contemplated herein that a modified pdt can be generated using a homolog or variant of mf-ssrA (e.g., an ssrA tag from another member of the *Mycoplasma* family). Similarly, it also contemplated herein that a protease capable of degrading a pdt or modified pdt as described herein can be obtained from a member of the *Mycoplasma* family or derived from a protease from a member of the *Mycoplasma* family (e.g., a modified Lon protease from another *Mycoplasma* family member).

In addition, it is contemplated herein that one of skill in the art can attach one or more pdts or modified pdts to a plurality of endogenous proteins, thereby permitting coordinated control of multiple cellular pathways by activating one or more cognate proteases, as described herein.

Also provided herein are vectors encoding the pdt sequence and a multiple cloning site for expression of a fusion protein comprising a target protein and the pdt sequence. Vector constructs for expression of such fusion proteins will generally require regulatory elements, e.g., promoters, enhancers, etc., to ensure the expression of the construct in target cells. These and other specifics for vectors and constructs are described in further detail below in the section entitled "Component Parts".

In some embodiments, the nucleic acid sequence encoding the protease is codon optimized Methods for codon optimization of a nucleic acid sequence are known to those of skill in the art. For example, a nucleic acid sequence can be modified to encode a recombinant polypeptide variant wherein specific codons of the nucleic acid sequence have been changed to codons that are favored by a particular host, resulting in enhanced levels of expression (see, e.g., Haas et al., Curr. Biol. 6:315, 1996; Yang et al., Nucleic Acids Res. 24:4592, 1996). Other methods for codon optimization include, but are not limited to, modification of translation initiation regions, alteration of mRNA structural elements, and the use of different codon biases.

In certain embodiments, protease is genomically integrated into the bacterium e.g., *E. coli* or *L. lactis*. Methods for genomically integrating a nucleic acid sequence into a bacterial genome are known to those of ordinary skill in the art. Genomic integration permits the expression of the modified protease in a bacterium and as such, does not require selection using an antibiotic or other selection mechanism to maintain a plasmid in a culture of bacteria. Thus, genomic integration has the added advantage of producing a stronger and/or faster inducible degradation or protein targets, thereby allowing one of skill in the art more options for controlling degradation of a target protein(s). Genomic integration of a nucleic acid sequence encoding a modified protease is particularly useful in an industrial or commercial setting in which controlled degradation of a protein target is desired, without the need for cumbersome plasmid selection steps.

Degradation Modules and Systems

The degradation systems described herein are highly modular, requiring only a small peptide tag and a single protease to function. Unlike other degradation systems, the systems described herein permit predictable and independent control of both the initial protein level and inducible degradation rate of any targeted protein. Furthermore, this degradation system does not require disruption of any host genes or pathways to enable the system to function, and is transferable to other bacteria (e.g., gram-negative and gram-positive bacteria) and eukaryotes with minimal modifications. The use of a unique degradation tag and cognate protease enables inducible targeted protein degradation. In addition, the use of a plurality of unique degradation tags (two or more different tags) and their cognate proteases enables inducible targeted protein degradation of a plurality of tagged proteins (e.g., 2, 3, 4 or more), thereby permitting one of skill in the art to control multiple cellular pathways in a coordinately controlled fashion.

The system can be used to control endogenous cellular processes, which is useful in any process that requires control or circumvention of cellular pathways, such as metabolic engineering for production of pharmaceuticals or other compounds.

The degradation system described herein can be used to control a wide variety of synthetic circuits for use in fields such as biofabrication and biosensor design. It can be used to control cell movement and therefore allow engineered targeting of cells to specific niches in the body for subsequent expression or release of therapeutic proteins or compounds. Other examples include its use in a vaccine delivery system whereby the degradation system can induce cell lysis to release cytoplasmic antigen contents.

The degradation system described herein also offers pharmaceutical companies a *facile* method to identify the phenotypes associated with targeted protein inhibition (in this case through degradation) before beginning the expensive and labor-intensive process of identifying potent protein-specific small-molecule inhibitors. Thus, in one embodiment, the degradation system described herein is used in a screening assay or as a screening platform to identify bacterial targets for drug development (e.g., antibiotic development).

In one embodiment, the systems described herein comprise a modified mf-ssrA degradation tag fused to a target protein and a cognate protease that recognizes and degrades the modified degradation tag, or vectors thereof. In another embodiment, the systems described herein comprise an ssrA tag and/or a cognate protease, or vectors thereof, from another *Mycoplasma* or related species.

Also provided herein are a variety of biological outputs that can be used to indicate the status of a cell process (e.g., metabolic state, apoptosis, necrosis, growth etc.) or the level of the target protein in the cell using the synthetic degradation systems and protein degradation tags herein. These biological outputs, or "output products," as defined herein, refer to products that can be used as markers of specific states of the system as described herein. An output sequence can include a protein or an RNA molecule for the target protein or a detectable protein that is used to track or mark the state of the cell upon expression of the degradation system in a bacterial cell or upon initiation of inducible degradation using the system described herein. Such output products can be used to distinguish between various states of a cell. For example, upon expression and/or induction of the degradation system in the cell, the output gene product of the target protein can cause detectable changes in a variety of cellular pathways including, e.g., in response to changes in chemicals in the external environment or in response to drug exposure (e.g., antibiotic).

In some embodiments of the aspects described herein, the output products are "reporters." As defined herein, "reporters" refer to proteins that can be used to measure gene expression. Reporters generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. In some embodiments, reporters are used to quantify the rate or degree of target protein degradation in the cell. In some embodiments, reporters can be fused in-frame to other protein coding sequences to identify where a protein is located in a cell or organism.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In other embodiments, flow cytometers can be used for measuring the distribution in reporter activity across a large population of cells. In some embodiments, plate readers can be used for taking population average measurements of many different samples over time. In other embodiments, instruments that combine such various functions can be used, such as multiplex plate readers designed for flow cytometers, and combination microscopy and flow cytometric instruments.

Fluorescent proteins are convenient ways to visualize or quantify the output of a module or a biological circuit chemotactic converter described herein. Fluorescence can be readily quantified using a microscope, plate reader or flow cytometer equipped to excite the fluorescent protein with the appropriate wavelength of light. Since several different fluorescent proteins are available, multiple gene expression measurements can be made in parallel. Non-limiting examples of fluorescent proteins are provided in Table 1.

TABLE 1

Examples of Fluorescent Protein Reporters

| Name | Protein | Description | Tag | Emission | Excitation | Length |
|---|---|---|---|---|---|---|
| BBa_E0030 | EYFP | enhanced yellow fluorescent protein derived from *A. victoria* GFP | None | 527 | 514 | 723 |
| BBa_E0020 | ECFP | engineered cyan fluorescent protein derived from *A. victoria* GFP | None | 476 | 439 | 723 |
| BBa_E1010 | mRFP1 | engineered mutant of red fluorescent protein from *Discosoma striata* (coral) | None | 607 | 584 | 681 |
| BBa_E2050 | mOrange | derivative of mRFP1, yeast-optimized | None | 562 | 548 | 744 |
| BBa_E0040 | GFPmut3b | green fluorescent protein derived from jellyfish *Aequeora victoria* wild-type GFP (SwissProt: P42212 | None | 511 | 501 | 720 |
| BBa_J52021 | | dnTraf6-linker-GFP | | | | 1446 |
| BBa_J52026 | | dnMyD88-linker-GFP | | | | 1155 |
| BBa_I715022 | | Amino Portion of RFP | | | | 462 |
| BBa_I715023 | | Carboxyl portion of RFP | | | | 220 |
| BBa_I712028 | | CherryNLS - synthetic construct monomeric red fluorescent protein with nuclear localization sequence | | | | 733 |
| BBa_K125500 | | GFP fusion brick | | | | 718 |
| BBa_K106000 | | GFP, AarI BD part | | | | 714 |
| BBa_K106004 | | mCherry, AarI AB part | | | | 708 |
| BBa_K106005 | | mCherry, AarI BD part | | | | 708 |
| BBa_K106028 | | GFP, AarI AB part | | | | 714 |
| BBa_K165005 | | Venus YFP, yeast optimized for fusion | | | | 744 |
| BBa_K157005 | | Split-Cerulean-cCFP | | | | 261 |
| BBa_K157006 | | Split-Cerulean-nCFP | | | | 483 |

TABLE 1-continued

Examples of Fluorescent Protein Reporters

| Name | Protein | Description | Tag | Emission | Excitation | Length |
|---|---|---|---|---|---|---|
| BBa_K157007 | | Split-Venus-cYFP | | | | 261 |
| BBa_K157008 | | Split-Venus-nYFP | | | | 486 |
| BBa_K125810 | | slr2016 signal sequence + GFP fusion for secretion of GFP | | | | 779 |
| BBa_K082003 | GFP | GFP(+LVA) | | | | 756 |
| BBa_K156009 | | OFP (orange fluorescent protein) | | | | 864 |
| BBa_K156010 | | SBFP2 (strongly enhanced blue fluorescent protein) | | | | 720 |
| BBa_K106671 | | GFP, Aar1 AD part | | | | 714 |
| BBa_K294055 | GFPmut3b | GFP RFP Hybrid | None | 511 | 501 | 720 |
| BBa_K192001 | | CFP +tgt +lva | | | | 858 |
| BBa_K180001 | GFPmut3b | Green fluorescent protein (+LVA) | LVA | | | 754 |
| BBa_K283005 | | lpp_ompA_eGFP_streptavidin | | | | 1533 |
| BBa_K180008 | mCherry | mCherry (rights owned by Clontech) | | | | 708 |
| BBa_K180009 | mBanana | mBanana (rights owned by Clontech) | | | | 708 |

Luminescence can be readily quantified using a plate reader or luminescence counter. Luciferases can be used as output products for various embodiments described herein, for example, measuring low levels of gene expression, because cells tend to have little to no background luminescence in the absence of a luciferase. Non-limiting examples of luciferases are provided in Table 2.

TABLE 2

Examples of Luciferases

| Name | Description | Length |
|---|---|---|
| BBa_J52011 | dnMyD88- linker-Rluc | 1371 |
| BBa_J52013 | dnMyD88- linker-Rluc -linker-PEST191 | 1872 |
| BBa_I712019 | Firefly luciferase—luciferase from *Photinus pyralis* | 1653 |

In other embodiments, enzymes that produce colored substrates can be quantified using spectrophotometers or other instruments that can take absorbance measurements including plate readers. Like luciferases, enzymes like β-galactosidase can be used for measuring low levels of gene expression because they tend to amplify low signals. Non-limiting examples of such enzymes are provided in Table 3.

TABLE 3

Examples of Enzymes that Produce Colored Substrates

| Name | Description | Length |
|---|---|---|
| BBa_I732006 | lacZ alpha fragment | 234 |
| BBa_I732005 | lacZ (encoding beta-galactosidase, full-length) | 3075 |
| BBa_K147002 | xylE | 924 |

Another reporter output product for use in the different aspects described herein includes fluoresceine-A-binding (BBa_K157004).

In some embodiments of the aspects described herein, the target protein is itself a transcriptional activator or repressor, the production of which by an output product sequence can result in a further change in state of the cell, and provide additional input signals to subsequent or additional modules or biological circuit chemotactic converters. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Non-limiting examples of transcriptional regulators as output products are provided in Table 4.

TABLE 4

Examples of Transcriptional Regulators

| Name | Protein | Description | Tag | Direction | Uniprot | Length |
|---|---|---|---|---|---|---|
| BBa_C0079 | lasR-LVA | lasR activator from *P. aeruginosa* PAO1(+LVA) | LVA | Forward | P25084 | 756 |
| BBa_C0077 | cinR | cinR activator from *Rhizobium leguminosarum* (+LVA) | LVA | Forward | ~Q84HT2 | 762 |
| BBa_C0179 | lasR | lasR activator from *P. aeruginosa* PAO1(no LVA) | None | Forward | P25084 | 723 |
| BBa_J07009 | ToxR | toxicity-gene activator from *Vibrio cholerae* | None | Forward | P15795 | 630 |
| BBa_K118001 | | appY coding sequence encoding a DNA-binding transcriptional activator | | | | 753 |
| BBa_K137113 | | rcsA | | | | 624 |
| BBa_K131022 | | LuxO D47E, *Vibrio harveyi* | | | | 1362 |

TABLE 4-continued

Examples of Transcriptional Regulators

| Name | Protein | Description | Tag | Direction | Uniprot | Length |
|---|---|---|---|---|---|---|
| BBa_K131023 | | LuxO D47A, *Vibrio harveyi* | | | | 1362 |
| BBa_K082006 | | LuxR-G2F | | | | 753 |
| BBa_K294205 | | This is a coding sequence of heat shock protein from *E. coli* | | | | 402 |
| BBa_S04301 | lasR-LVA | C0079:B0015 | LVA | Forward | P25084 | 918 |
| BBa_K266002 | lasR-LVA | LasR + Term | LVA | Forward | P25084 | 918 |
| BBa_C0012 | LacI | lacI repressor from *E. coli* (+LVA) | LVA | Forward | P03023 | 1128 |
| BBa_C0040 | TetR | tetracycline repressor from transposon Tn10 (+LVA) | LVA | Forward | P04483 | 660 |
| BBa_C0050 | CI HK022 | cI repressor from phage HK022 (+LVA?) | LVA | Forward | P18680 | 744 |
| BBa_C0051 | CI lambda | cI repressor from *E. coli* phage lambda (+LVA) | LVA | Forward | P03034 | 750 |
| BBa_C0052 | CI 434-LVA | cI repressor from phage 434 (+LVA) | LVA | Forward | P16117 | 669 |
| BBa_C0053 | C2 P22 | c2 repressor from *Salmonella* phage P22 (+LVA) | LVA | Forward | P69202 | 687 |
| BBa_C0073 | mnt-weak | mnt repressor (weak) from *Salmonella* phage P22 (+LVA) | LVA | Forward | P03049 | 288 |
| BBa_C0075 | cI TP901 | TP901 cI repressor from phage TP901-1 (+LVA) | LVA | Forward | none | 579 |
| BBa_C0074 | penI | penI repressor from *Bacillus licheniformis* (+LVA) | LVA | Forward | P06555 | 423 |
| BBa_C0072 | mnt | mnt repressor (strong) from *Salmonella* phage P22 (+LVA) | LVA | Forward | P03049 | 288 |
| BBa_C2001 | Zif23-GCN4 | Zif23-GCN4 engineered repressor (+LVA, C2000 codon-optimized for *E. coli*) | LVA | Forward | P03069 | 300 |
| BBa_C0056 | CI 434 | cI repressor from phage 434 (no LVA) | None | Forward | P16117 | 636 |
| BBa_J06501 | LacI-mut2 | LacI repressor (temperature-sensitive mut 265) (+LVA) | LVA | Forward | ~P03023 | 1153 |
| BBa_J06500 | LacI-mut1 | LacI repressor (temperature-sensitive mut 241) (+LVA) | LVA | Forward | ~P03023 | 1153 |
| BBa_C2006 | | MalE.FactorXa.Zif268-GCN4 | | | | 1428 |
| BBa_I715032 | | lacIq reverse | | | | 1128 |
| BBa_I732100 | | LacI | | | | 1086 |
| BBa_I732101 | | LRLa | | | | 1086 |
| BBa_I732105 | | ARL2A0101 | | | | 1086 |
| BBa_I732106 | | ARL2A0102 | | | | 1086 |
| BBa_I732107 | | ARL2A0103 | | | | 1086 |
| BBa_I732110 | | ARL2A0203 | | | | 1086 |
| BBa_I732112 | | ARL2A0301 | | | | 1086 |
| BBa_I732115 | | ARL4A0604 | | | | 1086 |
| BBa_K091001 | | LsrR gene | | Forward | | 954 |
| BBa_K091121 | | LacI wild-type gene | | | | 1083 |
| BBa_K091122 | | LacI_I12 protein | | | | 1083 |
| BBa_K143033 | | LacI (Lva−, N-terminal deletion) regulatory protein | | | | 1086 |
| BBa_K142000 | | lacI IS mutant (IPTG unresponsive) R197A | | | | 1128 |
| BBa_K142001 | | lacI IS mutant (IPTG unresponsive) R197F | | | | 1128 |
| BBa_K142002 | | lacI IS mutant (IPTG unresponsive) T276A | | | | 1128 |
| BBa_K142003 | | lacI IS mutant (IPTG unresponsive) T276F | | | | 1128 |
| BBa_K106666 | | Lac Repressor, AarI AB part | | | | 1104 |
| BBa_K106667 | | Lac Repressor, AarI BD part | | | | 1107 |
| BBa_K142004 | | lacI IS mutant (IPTG unresponsive) R197A T276A | | | | 1128 |
| BBa_K106668 | | Tet Repressor, AarI AB part | | | | 618 |
| BBa_K106669 | | Tet Repressor, AarI BD part | | | | 621 |
| BBa_K142005 | | lacI IS mutant (IPTG unresponsive) R197A T276F | | | | 1128 |
| BBa_K142006 | | lacI IS mutant (IPTG unresponsive) R197F T276A | | | | 1128 |
| BBa_K142007 | | lacI IS mutant (IPTG unresponsive) R197F T276F | | | | 1128 |
| BBa_K082004 | LacI | LacI-wild type | | | | 1083 |
| BBa_K082005 | LacI | LacI-Mutant | | | | 1083 |
| BBa_C0062 | LuxR | luxR repressor/activator, (no LVA?) | None | Forward | P12746 | 756 |
| BBa_C0071 | rhlR-LVA | rhlR repressor/activator from *P. aeruginosa* PA3477 (+LVA) | LVA | Forward | P54292 | 762 |

TABLE 4-continued

Examples of Transcriptional Regulators

| Name | Protein | Description | Tag | Direction | Uniprot | Length |
|---|---|---|---|---|---|---|
| BBa_C0080 | araC | araC arabinose operon regulatory protein (repressor/activator) from E. coli (+LVA) | LVA | Forward | P0A9E0 | 915 |
| BBa_C0171 | rhlR | rhlR repressor/activator from P. aeruginosa PA3477 (no LVA) | None | Forward | P54292 | 729 |
| BBa_K108021 | | Fis | | | | 297 |

In other embodiments of the various aspects described herein, genes encoding selection markers are used as output product sequences. "Selection markers," as defined herein, refer to protein coding sequences that confer a selective advantage or disadvantage to a biological unit, such as a cell. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, are those that are toxic to the cell. Positive selection markers are frequently used during cloning to select against cells transformed with the cloning vector and ensure that only cells transformed with a plasmid containing the insert. Non-limiting examples of selection marker output products are provided in Table 5.

In some embodiments of the aspects described herein, output product sequences encode "biosynthetic enzymes" that catalyze the conversion of substrates to products. For example, such biosynthetic enzymes can be combined together along with or within modules to construct pathways that produce or degrade useful chemicals and materials, in response to specific signals. These combinations of enzymes can reconstitute either natural or synthetic biosynthetic pathways. These enzymes have applications in specialty chemicals, biofuels, and bioremediation.

For example, N-Acyl Homoserine lactones (AHLs or N-AHLs) are a class of signaling molecules involved in bacterial quorum sensing. "Quorum sensing" refers to a method of communication between bacteria that enables the coordination of group based behavior based on population

TABLE 5

| Name | Protein | Description | UniProt | KEGG | Length |
|---|---|---|---|---|---|
| BBa_T9150 | PyrF | orotidine 5 | P08244 | eco:b1281; | 741 |
| BBa_J31002 | AadA-bkw | kanamycin resistance backwards (KanB) [cf. BBa_J23012 & BBa_J31003] | P0AG05 | none | 816 |
| BBa_J31003 | AadA2 | kanamycin resistance forward (KanF) [cf. BBa_J23012 & BBa_J31002] | P0AG05 | none | 816 |
| BBa_J31004 | CAT-bkw | chloramphenicol acetyltransferase (backwards, CmB) [cf. BBa_J31005] | P62577 | none | 660 |
| BBa_J31006 | TetA(C)-bkw | tetracycline resistance protein TetA(C) (backwards) [cf. BBa_J31007] | P02981 | | 1191 |
| BBa_J31005 | CAT | chloramphenicol acetyltransferase (forwards, CmF) [cf. BBa_J31004] | P62577 | none | 660 |
| BBa_J31007 | TetA(C) | tetracycline resistance protein TetA(C) (forward), [cf. BBa_J31006] | P02981 | | 1191 |
| BBa_K145151 | | ccdB coding region | | | 306 |
| BBa_K143031 | | Aad9 Spectinomycin Resistance Gene | | | 771 |
| BBa_K156011 | | aadA (streptomycin 3'-adenyltransferase) | | | 789 |

An output product sequence can encode an enzyme for use in different relating to the synthetic degradation systems described herein. In some embodiments, an enzyme output can be used as a response to a particular input. For example, expression of a target protein or conversely, inducible degradation of the target protein, with or without exposure to an effector agent (e.g., an antibiotic), can "turn on" a modular component that encodes an output gene product an enzyme that can degrade or otherwise destroy the toxin.

density. In synthetic biology, genetic parts derived from quorum sensing systems have been used to create patterns on a lawn of bacteria and to achieve synchronized cell behavior. AHL can diffuse across cell membranes and is stable in growth media over a range of pH values. AHL can bind to transcriptional activators such as LuxR and stimulate transcription from cognate promoters. Several similar quorum sensing systems exists across different bacterial species; thus, there are several known enzymes that synthesize or degrade different AHL molecules that can be used for the modules and protein degradation systems described herein.

TABLE 6

Examples of AHLs

| Name | Protein | Description | Direction | Uniprot | KEGG | E.C. | Length |
|---|---|---|---|---|---|---|---|
| BBa_C0061 | luxI-LVA | autoinducer synthetase for AHL | Forward | P12747 | none | none | 618 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0070 | rhlI-LVA | autoinducer synthetase for N-butyryl-HSL (BHL) and HHL | Forward | Q02QW5 | none | none | 642 |
| BBa_C0076 | cinI | autoinducer synthetase | Forward | Q1MDW1 | none | none | 702 |
| BBa_C0078 | lasI | autoinducer synthetase for PAI from *Pseudomonas aeruginosa* | Forward | P33883 | pae:PA1432 | none | 642 |
| BBa_C0161 | luxI | autoinducer synthetase for AHL (no LVA) | Forward | P12747 | none | none | 585 |
| BBa_C0170 | rhlI | autoinducer synthetase for N-butyryl-HSL (BHL) and HHL (no LVA) | Forward | Q02QW5 | none | none | 609 |
| BBa_C0178 | lasI | autoinducer synthetase for PAI from *Pseudomonas aeruginosa* (no LVA) | Forward | P33883 | pae:PA1432 | none | 609 |
| BBa_K091109 | | LuxS | | | | | 516 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0160 | aiiA | autoinducer inactivation enzyme aiiA (no LVA) | Forward | Q1WNZ5 | none | 3.1.1.— | 756 |

Also provided herein are biological modules, such as genetic toggle switches, comprising the protein degradation tags described herein, as well as different nucleic acid and protein components, including promoters, transcriptional activators, transcriptional repressors, recombinases, and output products, to be used as or within synthetic cellular degradation systems. The ability to manipulate and combine different components and modules provides flexibility in input and output responses of the degradation systems described herein.

As demonstrated herein in the Examples, the protein degradation tags described herein can be incorporated into genetic toggle switches and permit protease-based switching in synthetic circuits. Accordingly, provided herein, in some aspects are genetic toggle switches comprising one or more protein degradation tags described herein. A "genetic toggle switch," as defined herein, refers to a synthetic, addressable cellular memory unit or module that can be constructed from any two repressible promoters arranged in a mutually inhibitory network. A genetic toggle switch exhibits robust bistable behavior. By "robust bistable behavior" is meant that the toggle switch exhibits bistability over a wide range of parameter values and that the two states are tolerant of fluctuations inherent in gene expression, i.e., a genetic toggle switch does not flip randomly between states. Bistability of a genetic toggle switch is possible with any set of promoters and repressors as long as a minimum set of conditions are fulfilled, as described, for example, in T. S. Gardner et al., Nature (2000) 403: 339-342.

Bistability of a genetic toggle switch, as described herein, arises from a mutually inhibitory arrangement of at least two repressor sequences. The product of each repressor sequence, i.e., the repressor, can inhibit, at a transcriptional level, a translational level, or a combination thereof, the expression of a product encoded by the other repressor sequence. Thus, in the absence of an appropriate input or inducing agent, such as a transcriptional activating agent, two stable states are possible: a first state in which a first repressor is expressed and inhibits expression of a second repressor sequence, and a second state in which the second repressor is expressed and inhibits expression of the first repressor sequence. For example, in some aspects, repressors act at the transcriptional level, whereby a first promoter sequence drives expression of a first repressor sequence that encodes for a repressor specific for a second promoter sequence. The second promoter sequence, in turn, drives expression of a second repressor sequence that encodes for a repressor specific for a second promoter sequence. In such an aspect, switching between the two states (i.e., expression of the first or second repressor) is mediated by the presence of an exogenous or endogenous input agent, such as an agent that prevents repressor binding to the currently inactive promoter. In such an embodiment, the agent permits the opposing repressor to be maximally transcribed until it stably represses the originally active promoter. In other embodiments of the aspects described herein, repressors in a genetic toggle switch can act at the translational level, whereby a first repressor encodes a product, such as an inhibitory RNA molecule, that inhibits or prevents translation of the second repressor, or causes degradation of the second repressor mRNA. In other embodiments of the aspects described herein, different repressors in a genetic toggle switch can use different mechanisms of repression, i.e., transcriptional, translational, or combinations thereof.

In one embodiment of this aspect and all such aspects described herein, a genetic toggle switch comprises two different repressible promoter sequences driving expression of two sequences encoding different repressors, such that each promoter can be inhibited by the repressor transcribed by the other promoter. In such an embodiment, the genetic toggle switch comprises a first repressible promoter sequence ($rP_1$) that drives the transcription of a second repressor sequence ($R_2$), which encodes a repressor specific for the second repressible promoter sequence, and a second repressible promoter sequence ($rP_2$) that drives the transcription of a first repressor sequence ($R_1$), which encodes a repressor specific for the first repressible promoter sequence.

In some embodiments, the genetic toggle switches are implemented on plasmids, such as plasmids derived from *E. coli*. In some embodiments, the nucleic acid sequences of the promoters and repressors of the genetic toggle switch are contained or present on a single plasmid. In other embodiments, the nucleic acid sequences of the promoters and repressors of the genetic toggle switch are contained or present on multiple plasmids.

In one embodiment of this aspect and all such aspects described herein, the genetic toggle switch comprises a Ptrc-2 promoter that drives the expression of a temperature-sensitive λ repressor (cIts), and a $P_L$s1con promoter that drives the expression of a Lac repressor. In such an embodiment, the genetic toggle is switched between states by pulses of isopropyl-b-D-thiogalactopyranoside (IPTG) and thermal pulses. For example, a pulse of IPTG permits expression of cIts driven by the Ptrc-2 promoter, as the IPTG prevents the Lac repressor from binding to the Ptrc-2 promoter. Expression of cIts maintains the state of transcription from the Ptrc-2 promoter by binding and repressing the $P_L$s1con promoter, thus preventing Lac repressor expression and inhibition of the Ptrc-2 promoter. In contrast, a thermal pulse inhibits the cIts repressor, thus preventing cIts binding to the $P_L$s1con promoter, and permitting expression of the Lac repressor. Expression of the Lac repressor further maintains the state of transcription from the $P_L$s1con promoter by binding to and repressing the Ptrc-2 promoter, thus preventing cIts repressor expression and inhibition of the $P_L$s1con promoter.

In another embodiment of this aspect and all such aspects described herein, the genetic toggle switch comprises a Ptrc-2 promoter that drives the expression of a Tet repressor (Tet), and a $P_L$tetO-1 promoter that drives the expression of a Lac repressor. In such an embodiment, the genetic toggle switch is switched between states by a pulse of IPTG or a pulse of anhydrotetracycline (aTc). For example, a pulse of IPTG permits expression of Tet driven by the Ptrc-2 promoter, as the IPTG will prevent the Lac repressor from binding to the Ptrc-2 promoter. Expression of Tet maintains the state of transcription from the Ptrc-2 promoter by binding and repressing the $P_L$tetO-1 promoter, thus preventing Lac repressor expression and inhibition of the Ptrc-2 promoter. In contrast, a pulse of anhydrotetracycline inhibits the Tet repressor, thus preventing Tet binding to the $P_L$tetO-1 promoter, and permitting expression of the Lac repressor. Expression of the Lac repressor further maintains the state of transcription from the $P_L$tetO-1 promoter by binding to and repressing the Ptrc-2 promoter, thus preventing Tet repressor expression and inhibition of the $P_L$tetO-1 promoter.

For use in the genetic toggle switches and protein degradation systems described herein, it is possible to use any set of promoters and repressors as long as they fulfill a minimum set of conditions, as described, for example, in T. S. Gardner et al., Nature (2000) 403: 339-342. In some embodiments of the invention, the promoters useful in the genetic toggle switches are presented under the section entitled Promoters.

Degradation tag sequences are also provided for use in the genetic toggle switches and protein degradation systems described herein to enhance degradation of a protein expressing the tag (e.g., an mf-Lon protease or a variant or homolog thereof as described herein). The ability to add degradation tags to the proteins encoded by the genetic toggle switches and protein degradation systems described herein provide an additional layer of regulation and control of the modules. Non-limiting examples of such degradation tag sequences for use in the genetic toggle switches and protein degradation systems described herein are provided in Table 7, Table 8 or SEQ ID NOs: 1-26. Accordingly, in some embodiments of the aspects described herein, a genetic toggle switch comprises a protein degradation tag sequence.

In some embodiments, the rates of protein synthesis of transcriptional repressors for use in the genetic toggle switches described herein can also be modified by adding or modifying sequences for a ribosome binding site (RBS). In some embodiments, an RBS is placed downstream of a promoter sequence and upstream of a sequence encoding a transcriptional repressor being transcribed from that promoter.

In some embodiments, a genetic toggle switch can further comprise an output product sequence (OP) that encodes an output product, such as a protein or an RNA molecule, expression of which reflects or is indicative of the state of the genetic toggle switch. In such embodiments, the genetic toggle switch comprises a first repressible promoter sequence ($rP_1$) that drives the transcription of a second repressor sequence ($R_2$) that encodes a repressor specific for the second repressible promoter sequence, and a second repressible promoter sequence ($rP_2$) that drives the transcription of a first repressor sequence ($R_1$), which encodes a repressor specific for the first repressible promoter sequence, as well as the transcription of an output sequence (OP), i.e., the genetic toggle switch comprises $rP_1$-$R_2$ and $rP_2$-$R_1$-OP. In such embodiments, when the second repressible promoter is active and transcribing the first repressor and the output sequence, the toggle switch is considered in the "on" state. In such embodiments, the expression of the output product can be thought of as a digital output 00000001, in the binary system. In some embodiments of various aspects described herein, multiple genetic toggle switches are combined, each having a different output product that represents the state of that particular genetic toggle switch, such that the digital output of that combination of toggle switches is dependent on how many of the genetic toggle switches are in the "ON" state.

As used herein, a "digital output" refers to an output that can be represented in a binary format. The binary numeral system, or base-2 number system, represents numeric values using two symbols, 0 and 1. More specifically, the usual base-2 system is a positional notation with a radix of 2. Owing to its implementation in digital electronic circuitry using logic gates, the binary system is used internally by all modern computers. A "bit," as defined herein, is a binary digit. The numeric value represented by a combination of modules of the invention, for example, genetic toggle switches, is dependent upon the value assigned to each module when it is in the "on" state. For example, in those embodiments described herein where a combination of three genetic toggle switches is used, the digital output is represented as 00000000, when no genetic toggle switch is "on". When 1 genetic toggle switch is "on," i.e., transcribing the output product, the state is 00000001. When 2 genetic toggle switches are "ON," the state is 00000010. When all 3 genetic toggle switches are "on," the state is 00000011. A "byte" represents a collection of eight bits. A byte can hence be defined as a collection of 8 bits, such that 256 values or states can be represented, ranging from 0 to 255, i.e., 00000000 to 11111111.

Any such output product as described herein can be utilized. In some embodiments, where the expression of an output product is driven by only one of the two promoters in a toggle switch, the output product can encode a reporter protein or a reporter RNA molecule. In some embodiments, the reporter protein is a fluorescent reporter protein, e.g., green fluorescent protein. In some embodiments, where multiple genetic toggle switches are combined, each output sequence encodes for a different output product. For example, when a combination of three genetic toggle switches are combined, the output product sequences can encode for green fluorescent protein, yellow fluorescent protein, and red fluorescent protein, such that expression of all three fluorescent proteins represents a digital output of 00000011 for that combination of switches. Detection of the output products of the modules described herein can be performed using any method known to one of skill in the art, including, but not limited to, fluorescent detectors, such as microscopes and flow cytometers, luminescent detectors, quantitative PCR, Western blot analysis, etc., based on the nature of the output product being detected.

In other embodiments, each promoter in a genetic toggle switch can drive expression of an output product, such that the expression of one output product represents one digital output and expression of an output product driven by the opposing promoter represents another digital output, i.e., the "on" and "off" states of a single genetic toggle switch are represented by the expression of a different output product, which can be assigned in an arbitrary manner by a skilled artisan or user, or based on the design of the circuit in which the genetic toggle switch is a component. In such embodiments, the designation of which output product expression corresponds to which state, i.e., "on" or "off," can be determined by the skilled artisan.

In order to further enhance and expand the range and sensitivity of genetic toggle switches for use in the degradation systems described herein, it is useful to create libraries of genetic toggle switches with multiple interoperable repressors, such as transcriptional repressors. Thus, in some embodiments of the aspects described herein, a library of transcriptional repressors and activators can be targeted towards unique promoters with minimum crossover, using engineered zinc-finger proteins fused to transcriptional activation and repression domains.

To create such libraries, unique promoters containing sequence sites known to bind to engineered zinc-finger proteins can be synthesized. These sites are made up of three sequences, each of which is at least 3 DNA base pairs long. Each 3 base pair sequence binds to a single zinc-finger domain. Thus, in some embodiments, each complete engineered zinc-finger transcription factor contains three zinc-finger domains to target a total 9 base pair region of DNA.

In some embodiments, the number of zinc-finger domains used in a complete engineered zinc-finger transcription factor is 1. In some embodiments, the number of zinc-finger domains used in a complete engineered zinc-finger transcription factor is 2. In some embodiments, the number of zinc-finger domains used in a complete engineered zinc-finger transcription factor is 3. In some embodiments, the number of zinc-finger domains used in a complete engineered zinc-finger transcription factor is 4. In some embodiments, the number of zinc-finger domains used in a complete engineered zinc-finger transcription factor is 5. In some embodiments, the number of zinc-finger domains used in a complete engineered zinc-finger transcription factor is 6. In some embodiments, the number of zinc-finger domains used in a complete engineered zinc-finger transcription factor is 7. In some embodiments, the number of zinc-finger domains used in a complete engineered zinc-finger transcription factor is 8. In some embodiments, the number of zinc-finger domains used in a complete engineered zinc-finger transcription factor is 9. In some embodiments, the number of zinc-finger domains used in a complete engineered zinc-finger transcription factor is 10. In some embodiments, the number of zinc-finger domains used in a complete engineered zinc-finger transcription factor is 11. In some embodiments, the number of zinc-finger domains used in a complete engineered zinc-finger transcription factor is 12. In some embodiments, the number of zinc-finger domains used in a complete engineered zinc-finger transcription factor is 13. In some embodiments, the number of zinc-finger domains used in a complete engineered zinc-finger transcription factor is 14. In some embodiments, the number of zinc-finger domains used in a complete engineered zinc-finger transcription factor is 15. In some embodiments, the number of zinc-finger domains used in a complete engineered zinc-finger transcription factor is 15. In some embodiments, the number of zinc-finger domains used in a complete engineered zinc-finger transcription factor is 17. In some embodiments, the number of zinc-finger domains used in a complete engineered zinc-finger transcription factor is 18. In some embodiments, the number of zinc-finger domains used in a complete engineered zinc-finger transcription factor is 19. In some embodiments, the number of zinc-finger domains used in a complete engineered zinc-finger transcription factor is 20. In some embodiments, the number of zinc-finger domains used in a complete engineered zinc-finger transcription factor is at least 25, at least 50, at least 100, or more.

Representative examples of zinc-finger pools created for the bolded 3 base pair sequences are shown below (M L Maeder et al., *Molecular Cell* 2008: 31, 294-301):

| F1 | | | | F2 | | | | F3 | | | |
| --- | --- | --- | --- | --- | --- | --- | --- | --- | --- | --- | --- |
| GAA | GCA | GGA | GTA | GAA | GCA | GGA | GTA | GAA | GCA | GGA | GTA |
| GAC | GCC | GGC | GTC | GAC | GCC | GGC | GTC | GAC | GCC | GGC | GTC |
| GAG | GCG | GGG | GTG | GAG | GCG | GGG | GTG | GAG | GCG | GGG | GTG |
| GAT | GCT | GGT | GTT | GAT | GCT | GGT | GTT | GAT | GCT | GGT | GTT |
| TAA | TCA | TGA | TTA | TAA | TCA | TGA | TTA | TAA | TCA | TGA | TTA |
| TAC | TCC | TGC | TTC | TAC | TCC | TGC | TTC | TAC | TCC | TGC | TTC |
| TAG | TCG | TGG | TTG | TAG | TCG | TGG | TTG | TAG | TCG | TGG | TTG |
| TAT | TCT | TGT | TTT | TAT | TCT | TGT | TTT | TAT | TCT | TGT | TTT |

Using such pools, complete engineered zinc-finger proteins containing at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more zinc-fingers that can target synthetic promoters can be selected.

In some embodiments, the engineered zinc-finger proteins are fused to transcriptional activation domains, for e.g., VP16, VP64, p65, Gal4, α-subunit of RNA polymerase, Wild-type CRP (amino acid residues 1-209), CRP D1(residues 1-180), CRP D2 (residues 137-190), CRP D3 (residues 137-180) and CRP D4 (residues 151-168). In other embodiments, the engineered zinc-finger proteins are fused to transcriptional repressor domains e.g., SKD, KRAB (Margolin et al., 1994), SNAG, Kid, Ume6, CRP, SID (Ayer et al., 1996). Thus, an engineered zinc-finger protein can be used as a transcriptional activator or transcriptional repressor, depending on the requirements of the various embodiments described herein, by fusing an engineered zinc-finger protein with an appropriate transcriptional activator or transcriptional repressor domain. Non-limiting examples of methods of engineering zinc-finger proteins and transcriptional activation domains for fusion are discussed, for example, at Kwang-Hee B. et al, Nature Biotechnology 2003: 21, p. 275-280; R-J Kwon et al., Biotechnology Letters (2006) 28: 9-15; P. Blancafort et al., PNAS, 2005, 102: 33, p.11716-11721; J. T. Stege et al., The Plant Journal (2002) 32, 1077-1086; J. Y. Lee et al., Nucleic Acids Research, 2008, 36:16; K-S Park et al., Nature Biotechnology, 2003, 21:10, p.1208-1214; R. R. Beerli et al., PNAS, 2000, 97:4, p. 1495-1500; P. Blancafort et al., Nature Biotechnology 2003: 21, p. 269-274; D-k Lee, et al., Genome Res., 2003, 13: 2708-2716. Interoperability of such fusion engineered zinc-finger proteins can be assessed by combinatorial addition of the different engineered zinc-finger transcription factors to determine how promoter activity is affected.

To enhance cooperativity of engineered zinc-finger-based transcription factors, in some embodiments, engineered zinc-finger-based transcription factors can be further engineered to dimerize, using dimerization domains such as leucine zipper domains. In some embodiments, the affinity of monomeric engineered-zinc finger proteins can be increased or decreased by site-directed mutagenesis of amino acids known to contact the DNA backbone and/or bases. Non-limiting examples of methods to achieve such affinity modification are discussed, for example, at J. L. Pomerantz, et al., Biochemistry, 1998, 37: 4, p. 965-970, and S. A. Wolfe et al., Structure, 2000, 8:7, p. 739-750.

Pairwise combinations of the engineered zinc-finger-based transcriptional repressors can be conducted to identify mutually-repressing transcription factors and test for bistability, for use in the genetic toggle switches and other modules described herein. In some embodiments, the ability to flip genetic toggle switches can be assessed by overexpressing transcriptional repressors one by one. Thresholds for switching between repressors in such genetic toggle switches can be modulated by changing the promoters in the toggle switch to affect, for example, binding efficiency and repression efficiency.

Also provided herein are biological modules such as single invertase memory modules, comprising different nucleic acid and protein components, such as promoters, transcriptional activators, transcriptional repressors, recombinases, and output products, to be used in combination with the degradation system(s) described herein. The ability to manipulate and combine different components and modules provides flexibility in input and output responses of the inducible degradation system described herein.

In some aspects, a "single invertase memory module" is provided as a biological module for use with the inducible degradation system described herein. A "single invertase memory module (SIMM)," as defined herein, refers to a stable, switchable bit of memory that uses recombinases, such as Cre and $flp_e$, which can invert DNA between two oppositely oriented cognate recombinase recognition sites. A unique feature and advantage of SIMMs, of relevance to their with the methods and compositions described herein, is the ability to design such SIMMs to lack both "leakiness" and mixtures of inverted and non-inverted states that can be caused by expressing recombinases independently from their cognate recognition sites. Thus, the use of SIMMs in the biological circuit chemotactic converters described herein allows for the maintenance of memory, and provides the ability to control and maintain discrete states by expressing recombinases between their cognate recognition sites.

At a minimum, a SIMM is a nucleic acid-based module comprising a recombinase sequence located between its cognate recombinase recognition sites, i.e., $RRS_{for}$-RC-$RRS_{rev}$, where $RRS_{for}$ is a forward recombinase recognition site; RC is a recombinase sequence encoding a recombinase that recognizes $RRS_{for}$ and $RRS_{rev}$; and $RRS_{rev}$ is a reverse recombinase recognition site. Upon recombinase expression following activation of an upstream promoter, the recombinase causes a single inversion of the nucleic acid between the cognate recognition sites, i.e., the recombinase nucleic acid sequence or $RRS_{for}$-$RRS_{rev}$. Any further transcription from the upstream promoter yields antisense RNA of the recombinase gene rather than sense RNA, and therefore no further recombinase protein is produced. Thus, the inversion event is discrete and stable, and does not result in a mixture of inverted and non-inverted states. The upstream promoter driving expression of the SIMM can be a promoter sequence within an upstream SIMM, another modular component, a component of the same SIMM, or be an isolated promoter sequence.

In some aspects, the SIMM further comprises an upstream promoter sequence, i.e., P-$RRS_{for}$-RC-$RRS_{rev}$, where P is a promoter sequence. In other aspects, a SIMM comprises the recombinase sequence located between its cognate recombinase recognition sites, and further comprises an inverted inducible promoter sequence upstream of the recombinase sequence, i.e., $RRS_{for}$-$iP_{inv}$-RC-$RRS_{rev}$, where $RRS_{for}$ is a forward recombinase recognition site, $iP_{inv}$ is an inverted promoter sequence, RC is a recombinase sequence, and $RRS_{rev}$ is a reverse recombinase recognition site. Upon recombinase expression following activation of an upstream promoter, the recombinase causes a single inversion of the DNA between the cognate recognition sites, including the nucleic acid sequence encoding itself, i.e., the recombinase nucleic acid sequence. Any further transcription from the upstream promoter yields antisense RNA of the recombinase gene rather than sense RNA, and therefore no further recombinase protein is produced. Further, the inverted promoter is now in the proper orientation to drive transcription of components of any downstream modules, for example, another SIMM. In some embodiments of the aspects described herein, the promoter is a constitutive promoter. In other embodiments of the aspects described herein, the promoter is a inducible promoter. In some embodiments, the inducible promoter is a repressible promoter. In some embodiments, the inducible promoter is activated by an activating agent.

In some embodiments of the aspects described herein, a SIMM can use any recombinase for encoding memory, rather than only unidirectional recombinases. In some embodiments, the recombinase is encoded between its cognate recombinase recognition sequences. In other embodiments, the recombinase is encoded outside of its cognate recombinase recognition sequences. In those embodiments where the recombinase is encoded outside of its cognate recombinase recognition sequences, the SIMM can be used as, for example, a waveform generator, such that the input or inputs that lead to recombinase expression results in constant inversion between the recombinase recognition sequences and is used to generate pulses of outputs. Such outputs can be any of the output products described herein. In some embodiments, the output is a fluorescent protein.

A SIMM can further comprise one or more components, including, but not limited to, degradation tag sequences, ribosome binding sequences, translational terminator sequences, and anti-sense sequences, that are added to, for example, enhance translation of mRNA sequences for protein synthesis, prevent further transcription downstream of the recombinase, or enhance degradation of the recombinase mRNA sequence or protein sequence once the recombinase sequence has been expressed. Such additional 'parts' or components, by enhancing the fidelity and accuracy of the biological modules, such as SIMMs, permit, for example, increased numbers and combinations of biological modules and improve the capabilities of the biological circuit chemotactic converters described herein.

Accordingly, in some embodiments, protein degradation tag sequences are also provided for use in the SIMMs and degradation systems described herein to enhance degradation of a protein expressing the tag (e.g., an mf-Lon protease as described herein). The ability to add one or more degradation tags to the proteins encoded by the SIMMs and systems described herein provides an additional layer of regulation and control of the modules. Non-limiting examples of such degradation tag sequences are provided in SEQ ID NOs: 1-26. Accordingly, in some embodiments of the aspects described herein, a SIMM further comprises a protein degradation tag sequence downstream of the recombinase sequence, i.e., the SIMM comprises i.e., the SIMM comprises $RRS_{for}$-RC-D-$RRS_{rev}$, where D is a degradation tag sequence. In other embodiments, a SIMM further comprises both an inverted promoter sequence and a degradation tag sequence upstream and downstream respectively of the recombinase sequence, i.e., the SIMM comprises $RRS_{for}$-$iP_{inv}$-RC-D-$RRS_{rev}$, where $iP_{inv}$ is an inverted promoter sequence and D is a degradation tag sequence.

In other embodiments of the aspects described herein, a SIMM can further comprise one or more ribosome binding site sequences (RBSs) to promote efficient and accurate translation of the mRNA sequences for protein synthesis. RBSs are useful components for modulating the efficiency and rates of synthesis of the proteins or other outputs encoded by the biological converter switches described herein. Non-limiting examples of such RBS sequences for use in the SIMMs described herein. Accordingly, in some embodiments of these aspects, a SIMM further comprises a ribosome binding site upstream of the recombinase sequence, i.e., the SIMM comprises $RRS_{for}$-RBS-R-$RRS_{rev}$, where RBS is a ribosome binding site. In other aspects, a SIMM further comprises both an inverted promoter sequence and a ribosome binding site upstream of the recombinase sequence, i.e., the SIMM comprises $RRS_{for}$-$iP_{inv}$-RBS-RC-$RRS_{rev}$, where $iP_{inv}$ is an inverted promoter sequence and RBS is a ribosome binding site sequence.

In other embodiments of the aspects described herein, one or more terminator sequences can be added to a SIMM to prevent activation of downstream genes or modules by an upstream promote sequence. Terminator sequences can be added to the end of, for example, the sequence encoding a recombinase in a SIMM, to prevent further transcription downstream of the recombinase. Thus, terminator sequences are useful with the methods and compositions described herein to prevent unwanted transcription driven by activation of the various modules. Non-limiting examples of such terminators for use in the SIMMs are described herein. Accordingly, in some embodiments of these aspects, a SIMM further comprises a transcriptional terminator sequence downstream of the recombinase sequence, i.e., $RRS_{for}$-RC-T-$RRS_{rev}$, where T is a terminator sequence. In other embodiments, a SIMM further comprises both an inverted promoter sequence and a terminator sequence upstream and downstream respectively of the recombinase sequence, i.e., the SIMM comprises $RRS_{for}$-$iP_{inv}$-RC-T-$RRS_{rev}$, where $iP_{inv}$ is an inverted promoter sequence and T is a terminator sequence.

In further embodiments of these aspects, a SIMM comprises both a ribosome binding site upstream of the recombinase sequence and a protein degradation tag sequence downstream of the recombinase sequence, i.e., the SIMM comprises $RRS_{for}$-RBS-RC-D-$RRS_{rev}$. In some embodiments, a SIMM further comprises an inverted promoter sequence and ribosome binding site upstream of the recombinase sequence, and a protein degradation tag sequence downstream of the recombinase sequence, i.e., the SIMM comprises $RRS_{for}$-$iP_{inv}$ RBS-RC-D-$RRS_{rev}$. In some embodiments of these aspects, a SIMM comprises both a protein degradation tag sequence and a transcriptional terminator sequence downstream of the recombinase sequence, i.e., the SIMM comprises $RRS_{for}$-$iP_{inv}$ RC-D-T-$RRS_{rev}$. In some embodiments, a SIMM further comprises an inverted promoter sequence upstream of the recombinase sequence, and a protein degradation tag sequence and a terminator sequence downstream of the recombinase sequence, i.e., the SIMM comprises $RRS_{for}$-$iP_{inv}$-RC-D-T-$RRS_{rev}$. In some embodiments of these aspects, a SIMM further comprises a ribosome binding site upstream of the recombinase sequence and a terminator sequence downstream of the recombinase sequence, i.e., the SIMM comprises $RRS_{for}$-$iP_{inv}$-RBS-RC-T-$RRS_{rev}$. In some embodiments, a SIMM further comprises an inverted promoter sequence and ribosome binding site upstream of the recombinase sequence, and a terminator sequence downstream of the recombinase sequence, i.e., the SIMM comprises $RRS_{for}$-$iP_{inv}$-RBS-RC-T-$RRS_{rev}$.

In some particular embodiments of these aspects, a SIMM can further comprise a ribosome binding site upstream of the recombinase sequence, and protein degradation tag and transcriptional terminator sequences downstream of the recombinase sequence, i.e., $RRS_{for}$-$iP_{inv}$-RBS-RC-D-T-$RRS_{rev}$. In other such embodiments, a SIMM further comprises an inverted promoter sequence and ribosome binding site upstream of the recombinase sequence, and protein degradation tag and transcriptional terminator sequences downstream of the recombinase sequence, i.e., the SIMM comprises $RRS_{for}$-$iP_{inv}$-RBS-RC-D-T-$RRS_{rev}$. In such embodiments, the combined addition of an RBS, a transcriptional terminator sequence, and a degradation tag to the SIMM provides an enhanced ability to regulate and control expression of the recombinase encoded by the SIMM.

In some embodiments of the aspects described herein, a SIMM can further comprise or be designed to include an antisense RNA sequence downstream of and in an inverted orientation in respect to the sequence encoding the recombinase, which is specific for the recombinase mRNA, i.e., $RRS_{for}$-RC-$asRNA_{inv}$-$RRS_{rev}$, where $asRNA_{inv}$ is an inverted antisense RNA sequence. In such embodiments, upon expression of the recombinase protein, in response, for example, to activation of an upstream promoter, the recombinase flips the sequences in the SIMM flanked by the recombinase recognition sites, such that the recombinase sequence is in the inverted orientation and the sequence encoding the antisense RNA is in the forward direction, i.e., $RRS_{for}$-asRNA-$RC_{inv}$-$RRS_{rev}$. The inversion event prevents further transcription and translation of the recombinase sequence, while transcription of the sequence encoding the antisense RNA specific for the recombinase enhances degradation of any transcribed recombinase mRNA sequence remaining. In further embodiments, the SIMM can further comprise a ribosome binding site upstream of the recombinase sequence, protein degradation tag or transcriptional terminator sequences downstream of the recombinase sequence, or any combination thereof, i.e., $RRS_{for}$-RBS-RC-asRNA$_{inv}$-D-T-$RRS_{rev}$, such that expression of the recombinase is regulated by a combination of elements to ensure accuracy and fidelity of the SIMM.

In some embodiments of these aspects and all such aspects described herein, a SIMM can be designed so that it can be reset by placing an additional promoter sequence in an inverted orientation downstream of the reverse recombinase recognition site, i.e., $RRS_{for}$-RBS-RC-$RRS_{rev}$; where $iP_{inv}$ is an inverted inducible promoter sequence. Upon activation of the promoter, the state of such a SIMM is flipped from its inverted state back to its original state, when the recombinase sequence is in the inverted orientation. In some embodiments, the same reverse inducible promoter can be used throughout an entire set of SIMMs, such that a single inducer can be used to perform a global reset of all the SIMMs in the system.

In some embodiments of these aspects and all such aspects described herein, a SIMM comprises a forward recombinase recognition site sequence, an inverted promoter sequence, a ribosome binding site sequence, a recombinase gene sequence, and a reverse recombinase recognition site sequence, and a sequence encoding an output product, i.e., $RRS_{for}$ $iP_{inv}$-RC-$RRS_{rev}$-OP; where $RRS_{for}$ is a forward recombinase recognition sequence; $P_{inv}$ is an inverted promoter sequence; RC is a recombinase gene sequence encoding a recombinase that is specific for $RRS_{for}$ and $RRS_{rev}$; $RRS_{rev}$ is a reverse recombinase recognition sequence, and OP is an output product sequence. In such embodiments, upon expression of the recombinase, the sequence between the two recombinase recognition sites is inverted, resulting in termination of recombinase expression and allowing for the inverted promoter sequence to be in the appropriate direction to drive expression of the output gene sequence and any downstream modules. In some embodiments, the promoter is an inducible promoter. In some embodiments, the inducible promoter is a repressible promoter, or a promoter that can be activated by an activating agent. In such embodiments, the SIMM can further comprise degradation tags, ribosome binding sites, transcriptional terminator sequences, and antisense RNA sequences, as described herein, to add further regulatory capacities to the SIMM.

In other embodiments of these aspects and all such aspects described herein, a SIMM can comprise an inducible promoter sequence (iP), a forward recombinase recognition site sequence ($RRS_{for}$), an inverted sequence of a constitutive promoter ($P_{inv}$), a recombinase gene sequence (RC), a reverse recombinase recognition site sequence ($RRS_{rev}$), and an output product sequence (OP), i.e., iP-$RRS_{for}$-$iP_{inv}$-RC-$RRS_{rev}$-OP. In such embodiments, activation of the inducible promoter drives expression of the recombinase, which inverts the sequence between the two recombinase recognition sites, resulting in termination of recombinase expression, and allowing for the inverted, constitutive promoter sequence to be in the appropriate direction to drive expression of the output product sequence and any downstream modules, for example, one or more additional SIMMs. In some such embodiments, the SIMM can further comprise an additional inducible promoter in inverted orientation between the reverse recombinase recognition site sequence and the output product sequence, i.e., (iP-$RRS_{for}$-$iP_{inv}$-RC-$RRS_{rev}$-$iP_{2,inv}$-OP), such that the upon activation of the reverse promoter, the state of the system is flipped from its inverted state back to its original state. In some such embodiments, the first and second inducible promoters are induced by different agents. In all such embodiments, the SIMM can further comprise one or more components such as degradation tags, ribosome binding sites, transcriptional terminator sequences, and antisense RNA sequences to further regulate the activated and steady-states of the SIMM.

In some embodiments of these aspects and all such aspects described herein, one or more additional components can be added to the SIMMs to increase the utility or functionality of the SIMM for use with the methods and compositions provided herein. In some embodiments, a SIMM comprises a forward promoter sequence, a forward recombinase recognition sequence, a ribosome-binding site sequence, a recombinase gene sequence, a transcriptional terminator sequence, an inverted output product sequence, an inverted ribosome-binding site sequence, and a reverse recombinase recognition site sequence, i.e., $P_{for}$-$RRS_{for}$-RBS-RC-T-$OP_{inv}$-$RBS_{inv}$-$RRS_{rev}$; where $P_{for}$ is a forward promoter sequence; $RRS_{for}$ is a forward recombinase recognition sequence; RBS is a ribosome-binding site sequence; RC is a recombinase gene sequence encoding a recombinase that recognizes $RRS_{for}$ and $RRS_{rev}$; T is a transcriptional terminator sequence; $OP_{inv}$ is the inverted sequence of any gene that can be used as an output; $RBS_{inv}$ is an inverted ribosome-binding site sequence; and $RRS_{rev}$ is a reverse recombinase recognition sequence. In such embodiments, upon activation of the forward promoter ($P_{for}$), the recombinase gene (RC) is expressed, causing inversion of the sequence between the two recombinase recognition sequences ($RRS_{for}$ and $RRS_{rev}$), thus allowing for expression of the output product sequence that is no longer in the inverted direction. In some embodiments, the output product sequence encodes a transcriptional repressor or activator. In some embodiments, the output product sequence encodes a reporter gene.

In other embodiments of these aspects and all such aspects described herein, a SIMM is provided that comprises a forward promoter sequence, a forward recombinase recognition sequence, a ribosome-binding site sequence, a recombinase gene sequence, a ribosome-binding site sequence, an output product sequence, an inverted ribosome-binding site sequence, and a reverse recombinase recognition site sequence, i.e., $P_{for}$-$RRS_{for}$-RBS-RC-RBS-OP-$RBS_{inv}$-$RRS_{rev}$, where $P_{for}$ is a forward promoter; $RRS_{for}$ is a forward recombinase recognition sequence; RBS are ribosome-binding site sequences; RC is a recombinase gene sequence encoding a recombinase that recognizes $RRS_{for}$ and $RRS_{rev}$; OP is the sequence of any output product, such as a protein or RNA molecule; $RBS_{inv}$ is an inverted ribosome-binding site sequence; and $RRS_{rev}$ is a reverse recombinase recognition sequence. In such embodiments, activation of the forward promoter sequence results in expression of both the recombinase and the output product, and then upon inversion of the sequence due to the activity of the recombinase, the expression of the output product is shut off. Thus, in such embodiments, the SIMM creates a single pulse of expression of an output gene product. In some embodiments, the output product sequence encodes a transcriptional repressor or transcriptional activator. In other embodiments, the output product sequence encodes an RNA molecule, such as an iRNA molecule, an antisense RNA molecule, or a microRNA molecule. Other non-limiting examples of output products for use in the SIMMs described herein are reporter proteins (e.g., green fluorescent protein), transcription factors, transcriptional repressors, or RNA molecules, such as riboswitches in prokaryotic and mammalian cells, as well as short-hairpin RNAs, antisense RNA molecules, and microRNA molecules in mammalian cells (F. J. Isaacs, Nat Biotechnol 22, 841 (2004)). Further non-limiting examples of output products for use in the SIMMs described herein, are provided in the sections entitled "Output Products" and "RNA Molecule Components and Output Products."

The recombinases and recombination recognition sequences for use in the SIMMs described herein can be selected from any known or variant, i.e., engineered, recombinase or recombinase recognition sequences, as determined by a skilled artisan. In some embodiments of the various aspects described herein, the recombinase is a Cre recombinase and the recombinase recognition sites are LoxP sites or variants thereof. Alternative site-specific recombinases include, but are not limited to, 1) the Flp recombinase of the 2 pi plasmid of *Saccharomyces cerevisiae* (Cox (1983) Proc. Natl. Acad. Sci. USA 80:4223) which recognize FRT sites and variants thereof; 2) the integrase of *Streptomyces* phage. PHI.C31 that carries out efficient recombination between the attP site of the phage genome and the attB site of the host chromosome (Groth et al., 2000 Proc. Natl. Acad. Sci. USA, 97: 5995); 3) the Int recombinase of bacteriophage lambda (lambda-int/attP) (with or without Xis) which recognizes att sites (Weisberg et al. In: Lambda II, supra, pp. 211-250); 4) the xerC and xerD recombinases of *E. coli* which together form a recombinase that recognizes the 28 bp dif site (Leslie and Sherratt (1995) EMBO J. 14:1561); 5) the Int protein from the conjugative transposon Tn916 (Lu and Churchward (1994) EMBO J. 13:1541); 6) TpnI and the β-lactamase transposons (Levesque (1990) J. Bacteriol. 172:3745); 7) the Tn3 resolvase (Flanagan et al. (1989) J. Mol. Biol. 206:295 and Stark et al. (1989) Cell 58:779); 8) the SpoIVC recombinase of *Bacillus subtilis* (Sato et al. J. Bacteriol. 172:1092); 9) the Hin recombinase (Galsgow et al. (1989) J. Biol. Chem. 264:10072); 10) the Cin recombinase (Halter et al. (1988) EMBO J. 7:3991); 11) the immunoglobulin recombinases (Malynn et al. Cell (1988) 54:453); and 12) the FIMB and FIME recombinases (Blomfield et al., 1997 Mol. Microbiol. 23:705).

The inverted promoter sequence in a SIMM can be used to drive transcription of downstream components of that SIMM or other biological modules upon recombinase activation and inversion of the promoter to the forward direction. Accordingly, an inverted promoter sequence for use in the SIMMs described herein can be a constitutive or inducible promoter, depending upon the requirements of the degradation systems. Non-limiting examples of such promoter sequences for use in the modules and systems described herein are provided herein.

In some aspects, biological circuit chemotactic converters that provide the ability to convert input signals received into expression of specific "sensory receptors" or "sensors" can be used in combination with the methods and compositions described herein. Expression of such sensors enable a biological system, such as a natural or synthetic (e.g., artificial) cell, to activate the necessary molecular components to move, or chemotaxis, in response to a chemotactic signal. The modular nature of the biological circuit chemotactic converters described herein permits flexibility and expansion of the converters to vary the range and sensitivity of input signals to which the biological circuit chemotactic converters can respond, and increases the numbers and combinations of sensors that are expressed, depending on the specific input signals received. Such signals that can act as input signals to the biological circuit chemotactic converters described herein include, but are not limited to, concentrations of inducing agents, which may include biological agents such as pheromones, hormones, growth factors, metabolites, and the like; concentrations of chemicals, environmental byproducts, metal ions, and other such molecules or agents; light levels; temperature; mechanical stress; or electrical signals, such as currents and voltages. Exemplary biological circuit chemotactic converters can be found in U.S. Patent Application No. US 2013/0034907, the contents of which are incorporated by reference in their entirety.

Biological circuit chemotactic converters can be used in engineering complex behavioral phenotypes in cellular systems, such as prokaryotic, eukaryotic, or synthetic cells, including e.g., chemotactic responses in cellular organisms.

Bacterial Cells

The protein degradation modules and system(s) described herein are contemplated for use with any species of bacteria. In some embodiments, the bacterial cells are gram-negative cells and in alternative embodiments, the bacterial cells are gram-positive cells. Non-limiting examples of species of bacterial cells useful for engineering with the methods and compositions as described herein include, without limitation, a cell(s) from *Escherichia coli, Bacillus subtilis, Salmonella typhimurium* and various species of *Pseudomonas, Streptomyces*, and *Staphylococcus*. Other examples of bacterial cells that can be genetically engineered for use with the biological circuit chemotactic converters of the invention include, but are not limited to, cells from *Yersinia* spp., *Escherichia* spp., *Acinetobacter* spp., *Klebsiella* spp., *Bordetella* spp., *Lactococcus* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Staphylococcus* spp., *Vibrio* spp., *Bacillus* spp., and *Erysipelothrix* spp. In some embodiments, the bacterial cells are *E. coli* cells. In other embodiments, the bacterial cells are *Lactococcus lactis* cells. Other examples of organisms from which cells can be transformed or transfected with the synthetic degradation system described herein include, but are not limited to the following: *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides,* cyanobacteria, *Escherichia coli, Helicobacter pylori, Selnomonas ruminatium, Shigella sonnei, Zymomonas mobilis, Mycoplasma mycoides,* or *Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain *PCC6803, Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis,*

*Staphylococcus epidermidis, Zymomonas mobilis, Streptomyces phaechromogenes, Streptomyces ghanaenis, Halobacterium* strain GRB, and *Halobaferax* sp. strain Aa2.2.

Component Parts

Promoters, and Promoter Inducing, Activating and Repressing Agents

Also provided herein are promoters and promoter sequences are for use in controlling the initial or inducible degradation of a target protein as described herein.

The term "promoter," as used herein, refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments of the invention to regulate the state of a module or a switch. In addition, in various embodiments of the invention, a promoter can be used in conjunction with an "enhancer," which refers to a cis-acting regulatory sequence involved in the transcriptional activation of a nucleic acid sequence downstream of the promoter. The enhancer can be located at any functional location before or after the promoter, and/or the encoded nucleic acid.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

Alternatively, certain advantages are gained by positioning a coding nucleic acid segment under the control of a "recombinant promoter" or "heterologous promoter," which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the biological converter switches and modules disclosed herein (see, e.g., U.S. Pat. Nos. 4,683,202, 5,928,906, each incorporated herein by reference). Furthermore, it is contemplated that control sequences that direct transcription and/or expression of sequences within non-nuclear organelles such as mitochondria, chloroplasts, and the like, can be employed as well.

Inducible Promoters

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the biological circuit chemotactic converters, systems, and methods described herein are capable of functioning in both prokaryotic and eukaryotic host organisms. In some embodiments of the different aspects described herein, mammalian inducible promoters are included, although inducible promoters from other organisms, as well as synthetic promoters designed to function in a prokaryotic or eukaryotic host can be used. One important functional characteristic of the inducible promoters described herein is their ultimate inducibility by exposure to an externally applied inducer, such as an environmental inducer. Exemplary environmental inducers include exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

The promoters for use with the synthetic degradation system as described herein encompass the inducibility of a prokaryotic or eukaryotic promoter by, in part, either of two mechanisms. In some embodiments of these aspects, the system described herein comprises suitable inducible promoters that can be dependent upon transcriptional activators that, in turn, are reliant upon an environmental inducer. In other embodiments, the inducible promoters can be repressed by a transcriptional repressor, which itself is rendered inactive by an environmental inducer, such as the product of a sequence driven by another promoter. Thus, unless specified otherwise, an inducible promoter can be one that is induced by an inducing agent that positively activates a transcriptional activator, or one which is derepressed by an inducing agent that negatively regulates a transcriptional repressor. In such embodiments of the various aspects described herein where it is required to distinguish between an activating and a repressing inducing agent, explicit distinction will be made.

Inducible promoters that are useful in the biological circuit chemotactic converters and methods of use disclosed herein include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and Drosophila cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the biological circuit chemotactic converters described herein.

Inducible promoters useful in the biological circuit chemotactic converters, methods of use and systems described herein also include those that are repressed by "transcriptional repressors," which are subject to inactivation by the action of environmental, external agents, or the product of another gene. Such inducible promoters can also be termed "repressible promoters" where it is required to distinguish between other types of promoters in a given module or component of the biological switch converters described herein. Examples include prokaryotic repressors molecules that can transcriptionally repress eukaryotic promoters that have been engineered to incorporate appropriate repressor-binding operator sequences. Preferred repressors for use in the modules and methods described herein are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause dissociation of the tet repressor from the engineered promoter and allow transcription of the sequence downstream of the engineered promoter to occur.

An inducible promoter useful with the methods and systems as described herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as described herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

Promoters that are inducible by ionizing radiation can be used in certain embodiments, where gene expression is induced locally in a cell by exposure to ionizing radiation, such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems described herein can be $Zn^{2+}$ metallothionein promoter, metallothionein-1 promoter, human metallothionein HA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

Inducible promoters useful in combination with the degradation tags and systems described herein for in vivo uses can include those responsive to biologically compatible agents, such as those that are usually encountered in defined animal tissues. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as described herein results in a switch between the "on" or "off" states of the transcription of the operably linked heterologous target gene. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosupressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the modules and biological circuit chemotactic converters as disclosed herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the aspects described herein, components of the Lac system are utilized. For example, a lac operator (LacO) can be operably linked to tissue specific promoter, and control the transcription and expression of the heterologous target gene and another repressor protein, such as the TetR. Accordingly, the expression of the heterologous target gene is inversely regulated as compared to the expression or presence of Lac repressor in the system.

Components of the tetracycline (Tc) resistance system of *E. coli* that have also been found to function in eukaryotic cells and been used to regulate gene expression can also be used in the various aspects described herein. For example, the Tet repressor (TetR), which binds to tet operator (tetO) sequences in the absence of tetracycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized.

A temperature- or heat-inducible gene regulatory system can also be used with the degradation tags, systems, and methods described herein, such as the exemplary TIGR system comprising a cold-inducible transactivator in the form of a fusion protein having a heat shock responsive regulator, rheA, fused to the VP16 transactivator (Weber et al,. 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or -regulated promoter can be used in accordance with the modules, biological circuit chemotactic converters, and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-1 68; Ohtsuka & Hata (2000) Int J Hyperthermia 16(3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-1 90; Kiang et al. (1998) FASEB J 12(14):1571-16-579), calreticulin (Szewczenko-Pawlikowski et al. (1997) Mol Cell Biochem 177(1-2): 145-1 52); clusterin (Viard et al. (1999) J Invest Dermatol 112(3):290-296; Michel et al. (1997) Biochem J 328(Pt1):45-50; Clark & Griswold (1997) J Androl 18(3):257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):31 7-325) are upregulated in response to heat. In the case of clusterin, a 14 base pair element that is sufficient for heat-inducibility has been delineated (Michel et al. (1997) Biochem J 328(Pt1):45-50). Similarly, a two sequence unit comprising a 10- and a 14-base pair element in the calreticulin promoter region has been shown to confer heat-inducibility (Szewczenko-Pawlikowski et al. (1997) Mol Cell Biochem 177(1-2): 145-1 52).

Other inducible promoters useful in the various embodiments of the aspects described herein include the erythromycin-resistance regulon from *E. coli*, having repressible ($E_{off}$) and inducible ($E_{on}$) systems responsive to macrolide antibiotics, such as erythromycin, clarithromycin, and roxithromycin (Weber et al., 2002). The $E_{off}$ system utilizes an erythromycin-dependent transactivator, wherein providing a macrolide antibiotic represses transgene expression. In the $E_{on}$ system, the binding of the repressor to the operator results in repression of transgene expression. Therein, in the presence of macrolides gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the $Pip_{ON}$ and $Pip_{OFF}$ systems in their respective manners, as described therein.

Another example of a promoter expression system useful for the modules and biological circuit chemotactic converters described herein utilizes a quorum-sensing (referring to particular prokaryotic molecule communication systems having diffusible signal molecules that prevent binding of a repressor to an operator site, resulting in derepression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another can be utilized in the aspects described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72(6):653-660), the hsp27 promoter is activated by 17-β-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6): 1637-1 644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is up-regulated in human brain tumors (Takano et al. (1997) Exp Cell Res 237(1):38-45). A promoter employed in methods of the present invention can show selective up-regulation in tumor cells as described, for example, for mortalin (Takano et al. (1997) Exp Cell Res 237(1):38-45), hsp27 and calreticulin (Szew-czenko-Pawlikowski et al. (1997) Mol Cell Biochem 177 (1-2): 145-1 52; Yu et al. (2000) Electrophoresis 2 1(14): 3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B): 4579-4583; Strik et al. (2000) Anticancer Res 20(6B):4457-4552).

As described herein, the promoters in the modular components of the systems described herein, such as genetic toggle switches, can drive expression of an operably linked recombinase, repressor, or output product, thus regulating expression and consequent activity of said recombinase, repressor, or output product. In some embodiments of the various aspects described herein, promoter sequences are added to cellular degradation system in order to enumerate and input physiological events and stimuli, such as activation of gene networks or exposure to nutrients, toxins, metabolites, or any environmental exposure.

In some embodiments of the various aspects described herein, the promoter sequence that is employed is an inducible promoter that allows control of the expression of one or more components of the degradation system using one or more chemical inducers.

Antibodies Directed Against a Modified pdt

In some embodiments, it is desirable to use and/or generate an antibody reagent against a modified pdt or cognate protease as described herein. In one embodiment, the antibody reagent is directed against an unmodified region of a protein degradation tag as described herein. Such antibody reagents are contemplated to permit quantification of the tagged protein, for example, using an immunoblotting technique such as a Western blot. An antibody reagent against a pdt, a modified pdt, or a variant or homolog thereof as described herein can be used to determine the cellular location of the tagged protein by immunohistochemistry or immunofluorescence.

As used herein, the term "antibody reagent" refers to a protein that includes at least one immunoglobulin variable domain or immunoglobulin variable domain sequence and which specifically binds a given antigen (e.g., a modified or unmodified protein degradation tag as described herein). For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J. Immunol 1996; 26(3):629-39)) as well as complete antibodies. An antibody can have the structural features of IgA, IgG, IgE, IgD, IgM (as well as subtypes thereof). Antibodies can be from any source, including primate (human and non-human primate) and primatized antibodies. The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; Kabat definitions are used herein). Each VH and VL is typically composed of three CDRs and four FRs, arranged from amino-terminus to carboxy-terminus in the following order: FR1, CDR1, FR2, CDR2, FR3, CDR3, FR4. One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. One or more of the framework regions can be human, e.g., FR1, FR2, FR3, and FR4 of the HC or LC. For example, at least 70, 75, 80, 85, 90, 91, 92, 93, 94, 95, 96, 97, 98, 99, or 100% of an immunoglobulin variable domain, the constant region, the constant domains (CH1, CH2, CH3, CL1), or the entire antibody can be human or effectively human. Fully human monoclonal antibodies also can be prepared by immunizing mice transgenic for large portions of human immunoglobulin heavy and light chain loci. Following immunization of these mice (e.g., XENOMOUSE™ (Abgenix), HUMAB-MOUSE™ (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans. The term "antigen-binding fragment" is used herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242: 423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated. Antibody reagents to be used for protein analysis are widely available through commercial sources including AbCam (Cambridge, Mass.), New England Biolabs (Ipswich, Mass.), Santa Cruz Biotechnologies (Santa Cruz, Calif.), and Cell Signaling (Danvers, Mass.), among others. Antibodies and antibody reagents can also be raised against a polypeptide or portion of a polypeptide by methods known to those skilled in the art. Antibodies are readily raised in animals such as rabbits or mice by immunization with the gene product, or a fragment thereof (e.g., PSA or PSMA). Immunized mice are particularly useful for providing sources of B cells for the manufacture of hybridomas, which in turn are cultured to produce large quantities of monoclonal antibodies. While both polyclonal and monoclonal antibodies can be used in the methods described herein, it is preferred that a monoclonal antibody is used where conditions require increased specificity for a particular protein. Phage display can also be particularly effective in identifying antibody reagents useful for the methods and assays described herein. Briefly, one prepares a phage library (using e.g., m13, fd, or lambda phage), displaying inserts from 4 to about 80 amino acid residues using conventional procedures. The inserts can represent, for example, a completely degenerate or biased array. One then can select phage-bearing inserts which bind to the desired region of the pdt or modified pdt. This process can be repeated through several cycles of reselection of phage that bind to the pdt or modified pdt molecules. Repeated rounds lead to enrichment of phage bearing particular sequences. DNA sequence analysis can be conducted to identify the sequences of the expressed polypeptides. The minimal linear portion of the sequence that binds to the pdt or modified pdt molecules can be determined One can repeat the procedure using a biased library containing inserts containing part, or all, of the minimal linear portion plus one or more additional degenerate residues upstream or downstream thereof.

The antibodies can be coupled to specific diagnostic labeling agents for imaging of the protein or fragment thereof. Labels include, for example, fluorescent or chromogenic labels, as well as antibody fusion proteins, such as antibody-GFP fusions or antibody fusions to other fluorescent proteins known in the art (e.g., enhanced green fluorescent protein (EGFP), *Renilla reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED)). A wide variety of fluorescent labels are available from and/or extensively described in the Handbook of Fluorescent Probes and Research Products 8.sup.th Ed. (2001), available from Molecular Probes, Eugene, Oreg., as well as many other manufacturers. In other embodiments, the antibody reagent is fused to a molecule that is readily detectable either by its presence or activity, including, but not limited to, luciferase, chloramphenicol acetyl transferase, β-galactosidase, secreted placental alkaline phosphatase, β-lactamase, human growth hormone, and other secreted enzyme reporters. A protein tagged with a pdt or modified pdt can be detected or isolated using techniques which are well known to one of skill in the art, including but not limited to immunohistochemistry, Western blot analysis, (i e), immunoblotting, ELISA, immunoprecipitation, lateral flow immunoassay, radioimmunoassay, etc.

In one embodiment, the antibody reagent recognizes an epitope on a modified pdt as described herein. In another embodiment, the antibody reagent recognizes an epitope comprising a sequence of SEQ ID NOs: 1-26. In another embodiment, the antibody reagent recognizes an epitope within the unmodified region of a modified pdt. In another embodiment, the antibody reagent recognizes an epitope comprising amino acids 1-13, 13-15, or 25-27.

Screening Assays

The protein degradation compositions, modules, and systems described herein are useful to screen for agents for altering a cellular process such as cell wall biosynthesis, cell division and/or chemotactic motility. In one embodiment, the screening assay is used to identify a candidate drug target. In another embodiment, the screening assay is used to test candidate agents (e.g., candidate antibiotics) for their effect on degradation of a target protein.

Such assays for drug screening studies have an advantage over existing assays because they use modified protein degradation tags and cognate proteases from a highly divergent species of bacteria (e.g., *Mesoplasma florum*). For example, the methods, assays, systems, and kits described herein can be used to identify and/or test agents that can alter protein degradation of a target protein.

Accordingly, provided herein are methods for screening a test compound for biological activity, the method comprising: (a) expressing in a bacterial cell, (i) a first modified protein degradation tag fused to a target protein, wherein the modified degradation tag comprises altered degradation dynamics by its cognate protease compared to an unmodified degradation tag, (ii) a cognate protease capable of degrading the modified protein degradation tag of (a), wherein the protease is not constitutively expressed by the bacterial cell, (b) contacting the cell of step (a) with a candidate agent, and (c) measuring an output product that reflects the amount of the target protein of step (a), wherein a decrease in the output product indicates that the candidate agent increases the rate or level of protein degradation in the cell. The effect on the cell can be one that is observable directly or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, modulate cell wall biosynthesis, modulate chemotactic motility, or a combination thereof. In some instances, a biological activity can refer to the ability of a test compound to produce a toxic effect in a biological sample.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™, AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Kits

Another aspect of the technology described herein relates to kits for enhancing or preventing degradation of a target protein, kits for screening a candidate agent and/or kits for a system comprising a modified pdt and its cognate protease derived from *Mesoplasma florum* or a homolog or variant thereof. Described herein are kit components that can be included in one or more of the kits described herein. In one embodiment, the kits described herein comprise a nucleic acid construct encoding a modified protein degradation tag and a multiple cloning site, wherein the modified protein degradation tag is derived from *Mesoplasma florum* and comprises altered degradation dynamics by its cognate protease compared to the unmodified *Mesoplasma florum* protein degradation tag. In another embodiment, the kit further comprises a nucleic acid construct comprising a cognate protease optionally fused to a second degradation tag that is sensitive to degradation by a constitutively expressed protease in the cell in which the system is to be employed, and wherein the degradation tag is optionally modified to have altered degradation dynamics compared to its unmodified counterpart.

In one embodiment, the kits described herein can include a bacterial cell that does not constitutively express the cognate protease provided in the kit, for example, an *E. coli* cell. In one embodiment, one or more medium or medium components are provided in the kit.

In some embodiments, the components described herein can be provided singularly or in any combination as a kit. In addition, the kit optionally comprises informational material.

In some embodiments, the compound in the kit can be provided in a watertight or gas tight container which in some embodiments is substantially free of other components of the kit. For example, medium component can be supplied in more than one container, e.g., it can be supplied in a container having sufficient reagent for a predetermined number of screening reactions, e.g., 1, 2, 3 or greater. One or more of the components as described herein can be provided in any form, e.g., liquid, dried or lyophilized form. It is preferred that the compound(s) described herein are substantially pure and/or sterile. When the one or more components described herein are provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The informational material can be descriptive, instructional, marketing or other material that relates to the methods described herein and/or the use of a compound(s) described herein for the methods described herein. The informational material of the kits is not limited in its form. In one embodiment, the informational material can include information about the vector, multiple cloning site, promoters etc. In one embodiment, the informational material relates to methods for using the screening assay.

In addition to a compound(s) described herein, the composition of the kit can include other ingredients, such as a solvent or buffer, a stabilizer, a preservative, and/or an additional agent, e.g., for using the modified pdt tags, systems or screening assays as described herein.

The kit can include a component for the detection of the modified protein degradation tag and/or the cognate protease etc. In addition, the kit can include one or more antibodies that bind the tag or cognate protease, or primers for an RT-PCR or PCR reaction, e.g., a semi-quantitative or quantitative RT-PCR or PCR reaction. Such components can be used to assess the expression of each component in a cell or the degree or rate of protein degradation. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

EXAMPLES

Protein Degradation Tag Characterization

Figure 1B:
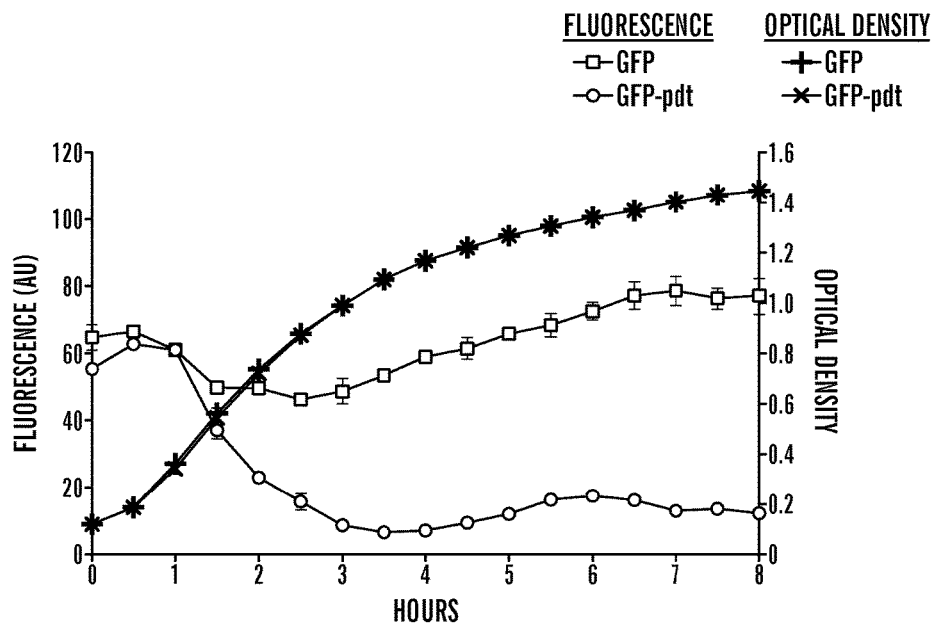

As described herein, GFP fluorescence was used to characterize mf-Lon-mediated protein degradation in *E. coli* and renamed the mf-ssrA tag "pdt" (protein degradation tag) to minimize confusion with the *E. coli* ssrA tag (FIG. 1A). During early logarithmic growth, constitutive expression of GFP bearing a C-terminal pdt fusion (GFP-pdt) resulted in fluorescence similar to untagged GFP, but GFP-pdt levels were markedly lower during late-log and stationary phase, indicating that pdt was recognized and degraded by one or more endogenous *E. coli* proteases (FIG. 1B).

Figure 1C:
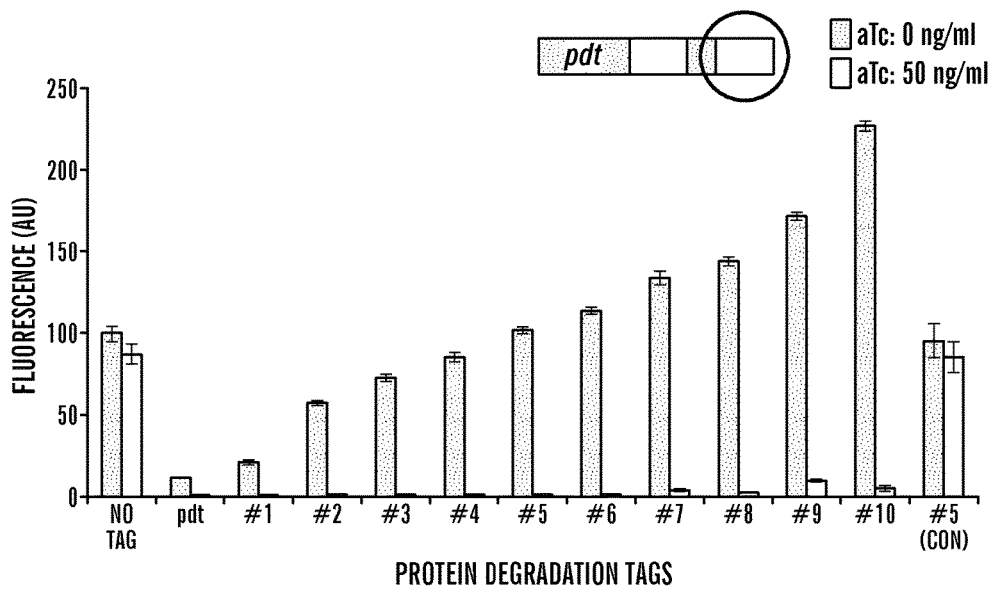
Figure 5:
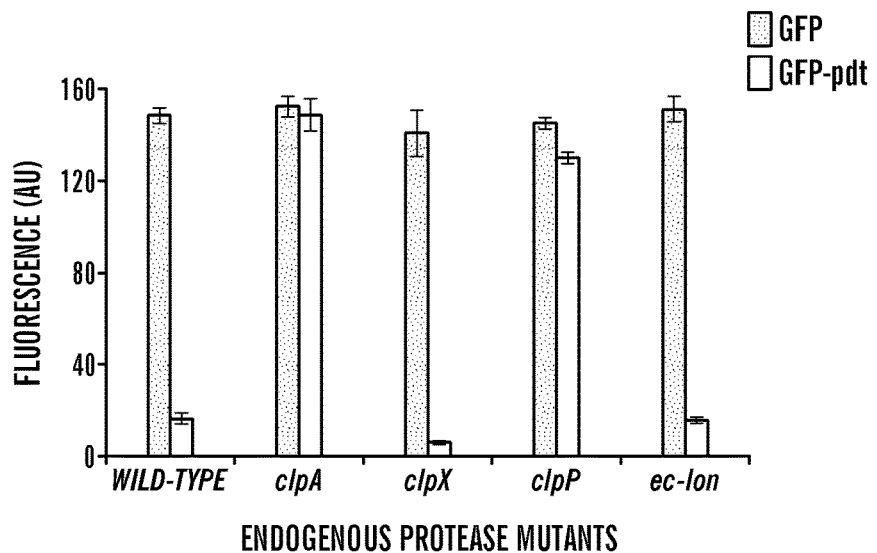
FIG. 5 demonstrates GFP-pdt degradation by endogenous E. coli proteases. Histogram of GFP and GFP-pdt levels in E. coli strains containing an in-frame deletion in the indicated protease gene. GFP and GFP-pdt were constitutively expressed from the PlacIq promoter, and fluorescence was measured by flow cytometry. Error bars represent the mean±standard deviation (SD) of three biological replicates.

It was therefore sought to generate pdt variants with increased resistance to endogenous degradation that remained fully susceptible to mf-Lon degradation. High GFP-pdt fluorescence in a ΔclpA mutant strain (FIG. 5) and weak sequence homology between pdt and the ClpA binding site on ec-ssrA[16] led us to target pdt residues 24-27 for mutagenesis (FIG. 1A, "numbers"). A 2000-member library of GFP-pdt clones were screened by plate fluorimetry to isolate GFP-pdt variants, denoted with numbers, that displayed both high initial protein levels and strong degradation following mf-Lon expression (FIG. 1C and Table 7).

Untagged GFP levels remained largely unaffected by mf-Lon expression while GFP-pdt displayed a 21-fold drop from its low initial levels, confirming the specificity of pdt-mediated mf-Lon degradation. The pdt variants identified in the screen displayed a range of initial GFP levels up to 23-fold higher than the parental pdt tag, and they exhibited up to a 60-fold drop in GFP following mf-Lon induction. Sequence analysis of these pdt variants showed that a majority contained multiple arginine and glutamine residues in the mutagenized region and none contained negatively charged residues (Table 7). Using these design criteria, additional pdt variants were engineered with high steady-state GFP levels that were effectively degraded by mf-Lon (Table 7).

Figure 2A:
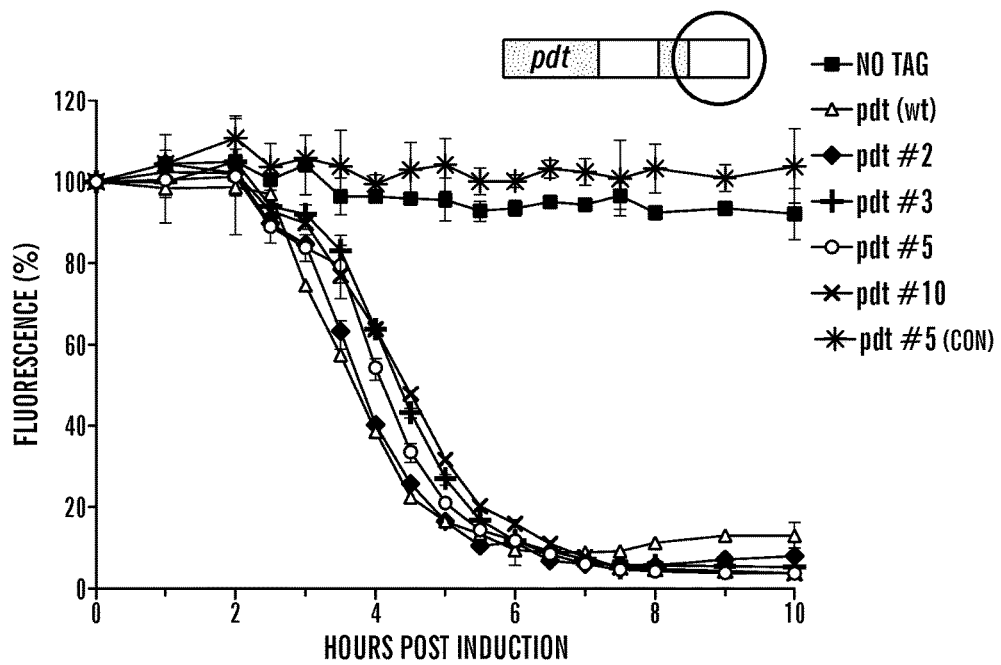
FIGS. 2A-2D demonstrate degradation dynamics of pdt variants and mf-Lon.
Figure 6:
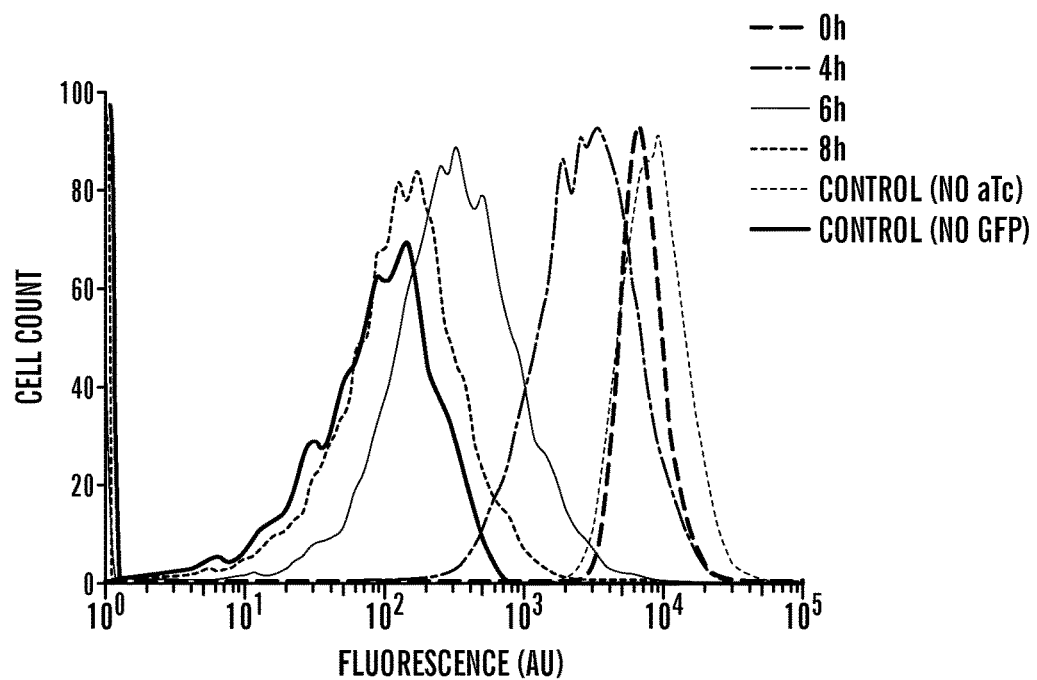
FIG. 6 demonstrates population-level degradation dynamics. Cells that constitutively express GFP-pdt#5 were induced to express mf-Lon (50 ng/ml aTc), and the GFP fluorescence of 10,000 cells was measured by flow cytometry at the indicated time post induction. The histogram plot shows a monomodal shift in the cell population over time. The control plot of cells that do not contain the GFP expression plasmid (no GFP) shows that mf-Lon express reduces GFP fluorescence to near baseline levels. The control plot of cells at 8 h that were not induced with aTc (no aTc) demonstrates that the fluorescence shift is dependent on aTc induction.

Flow cytometry was used to further characterize mf-Lon-mediated GFP-pdt degradation and it was found that the pdt variants displayed temporal degradation dynamics similar to wild-type pdt, reducing GFP levels ~20-50 fold by 7 h (FIG. 2A). Critically, GFP degradation did not occur in the absence of either mf-Lon or the pdt tag, and the tight monomodal shift in the fluorescent population distribution showed that degradation occurred across all cells in the experimental population (FIG. 6).

Figure 2B:
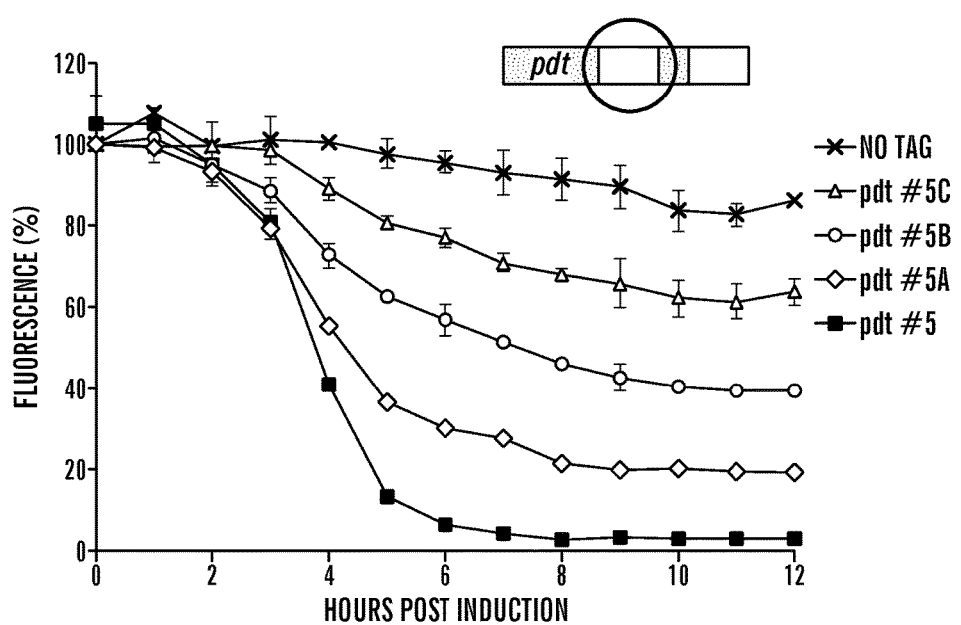

Next, the inventors sought to identify orthogonal pdt variants that alter mf-Lon recognition but not recognition by endogenous *E. coli* proteases (FIG. 1A, "letters"). GFP-pdt#5 was used as the parental tag because its basal level was similar to untagged GFP and then targeted pdt residues 13-15 for modification for three reasons: the homologous region in *Mycoplasma pneumoniae* is essential for Lon-mediated degradation[17], the region shows no homology to known ClpA, ClpX or SspB binding sites[16], and the residues are physically distant from those targeted in the first screen. Pdt variants that maintained initial GFP levels and displayed a range of mf-Lon dependent degradation rates were identified and denoted with letters (FIG. 2B and Table 7).

Figure 2C:
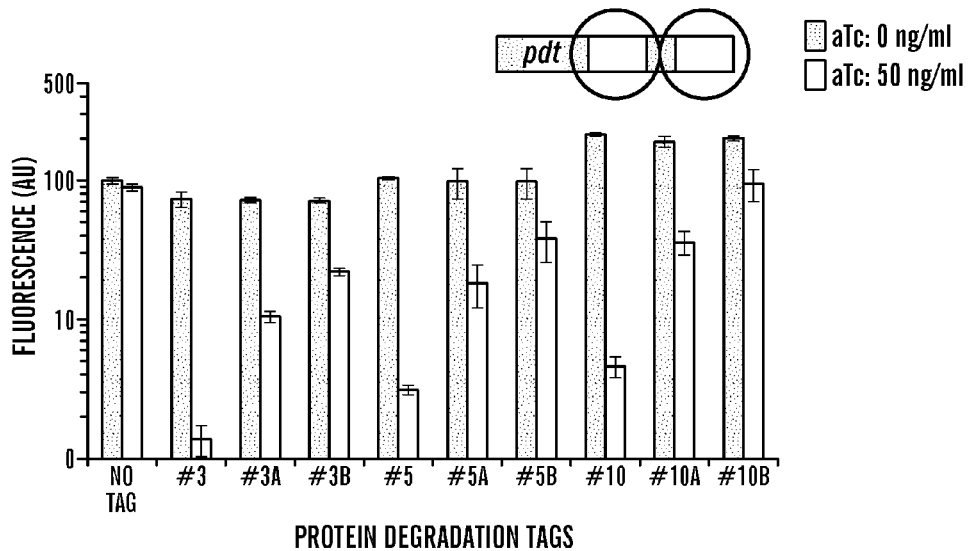

To determine if these letter variants could be combined with other number variants to create hybrid tags with predictable control over both the initial protein level and induced degradation rate, a panel of hybrid pdt variants was created and fluorescence was measured in the presence and absence of mf-Lon induction. As seen in FIG. 2C, the hybrid pdt variants functioned as predicted, independently controlling both degradation parameters according to the number and letter variants used.

Tunable Protease Expression

The degradation rate of pdt variants is dependent not only on their sequence and expression level, but also on the expression and degradation rate of mf-Lon. Using GFP-pdt#5 as a surrogate measure of mf-Lon protease levels, mf-Lon was characterized using transcriptional and post-translational control mechanisms. Fusion of the strong ec-ssrA tag ec-LAA to mf-Lon reduced mf-Lon protein levels below detectable levels even under full transcriptional induction (FIG. 2D), but fusion of the weakened ec-AAV tag allowed mf-Lon to degrade GFP-pdt#5 to 38% of its initial levels at maximal expression. Remarkably, the weakest ec-ssrA variant, ec-ASV, actually increased mf-Lon protein levels above wild-type levels, as evidenced by the reduced aTc concentration required to induce maximal GFP-pdt#5 degradation. Introduction of an inactivating mutation in the conserved active site of the mf-Lon protease domain (S692A)[18] completely abrogated its activity towards GFP-pdt#5, demonstrating that the observed reduction in GFP fluorescence following mf-Lon expression was due to mf-Lon-mediated GFP degradation and not solely unfolding by its AAA+ unfoldase domain[19].

Protease-Driven Control of a Synthetic Toggle Switch

Figure 3A:
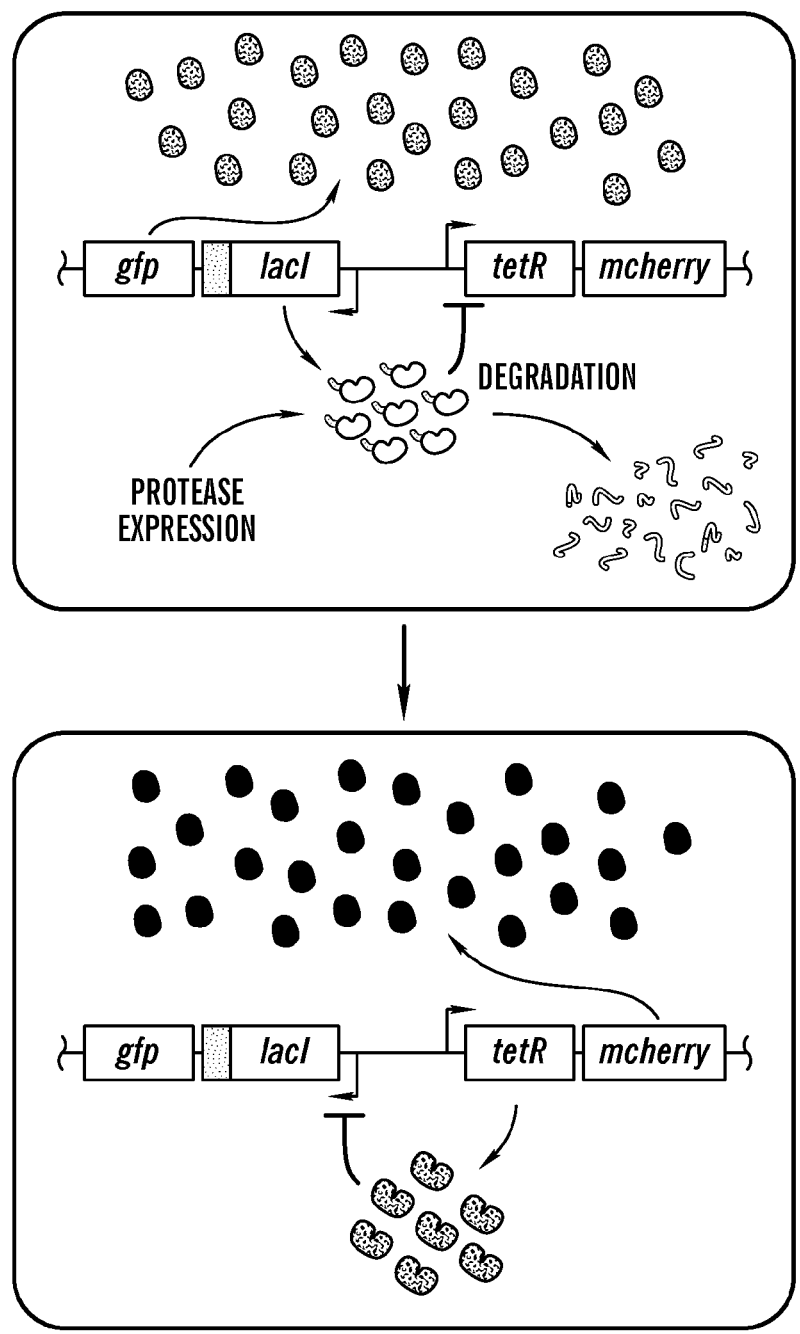
FIGS. 3A-3C demonstrate protease-driven control of a synthetic toggle switch.
Figure 3B:
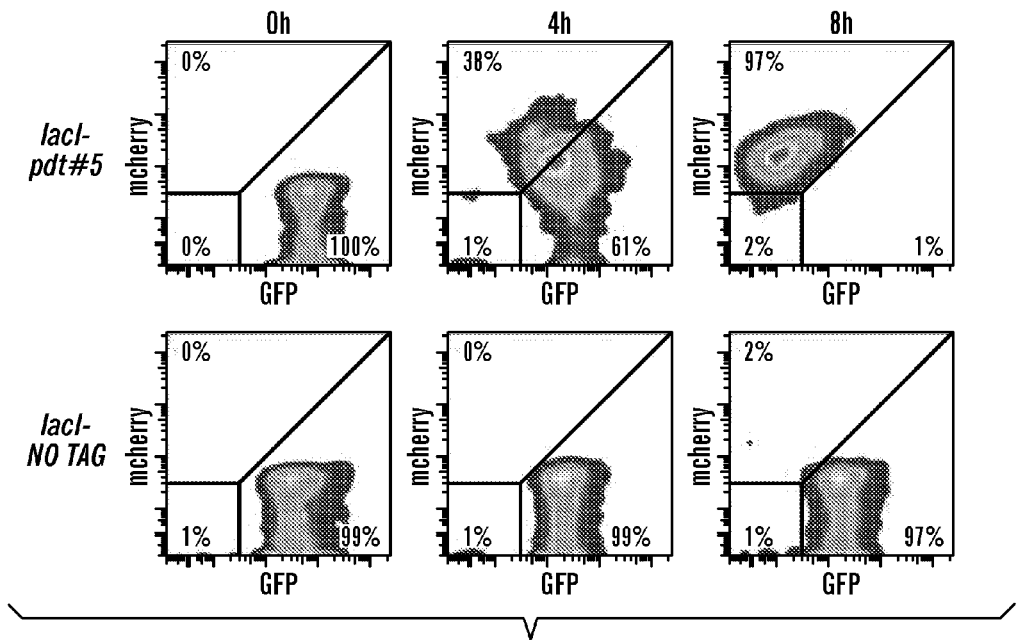
Figure 3C:
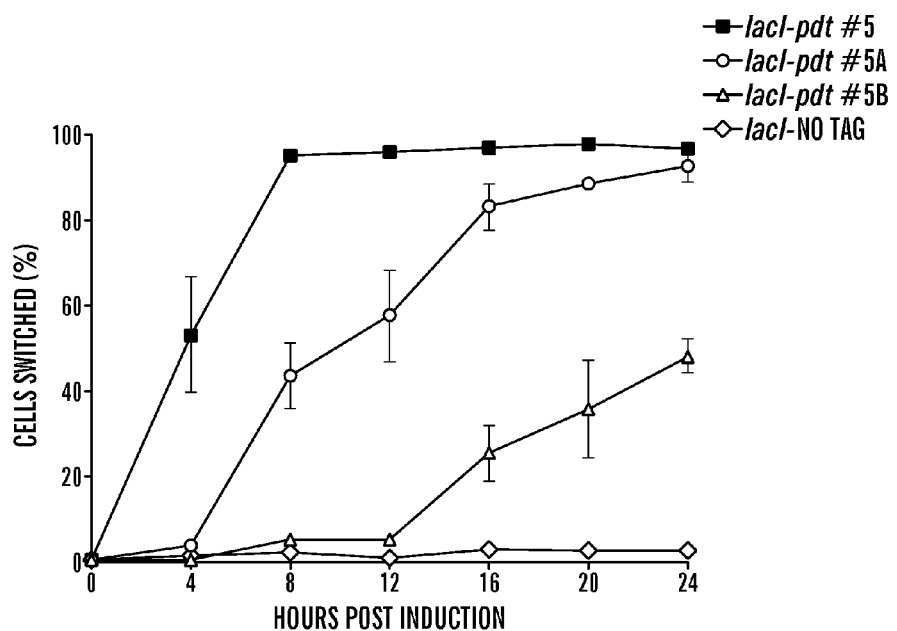
Figure 7:
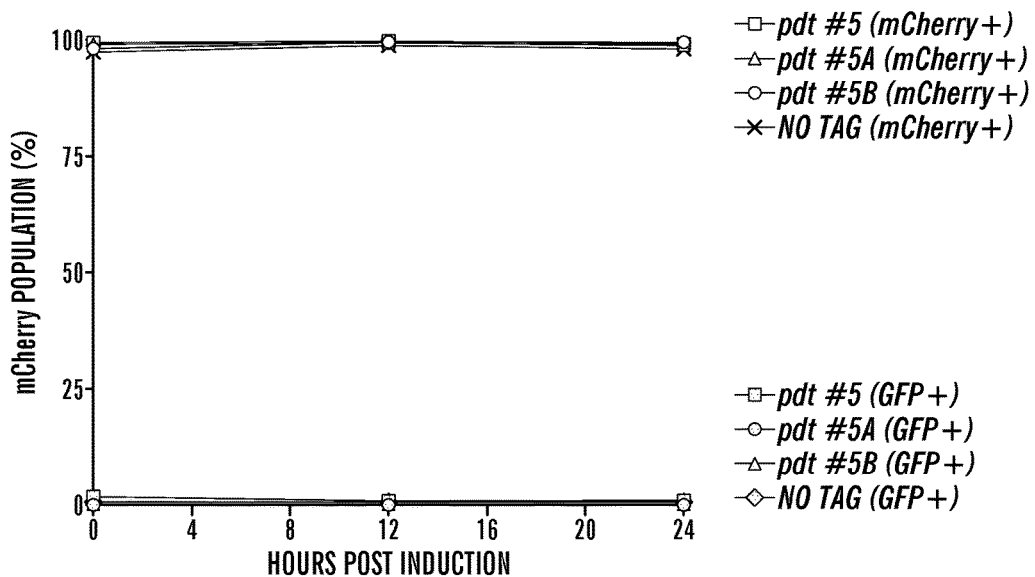
FIG. 7 demonstrates protease-inducible toggle switches are bistable. Cells containing a toggle switch with the indicated lacI-pdt fusion were switched into the GFP+ state or mCherry+ state with aTc or IPTG, respectively. The cells were then moved into non-inducing media and monitored over time for their toggle switch state using the parameters shown in FIG. 3B. All of the strains remained stable in their initial states and did not errantly switch states. Error bars represent the mean±standard deviation (SD) of three biological replicates.
Figure 8:
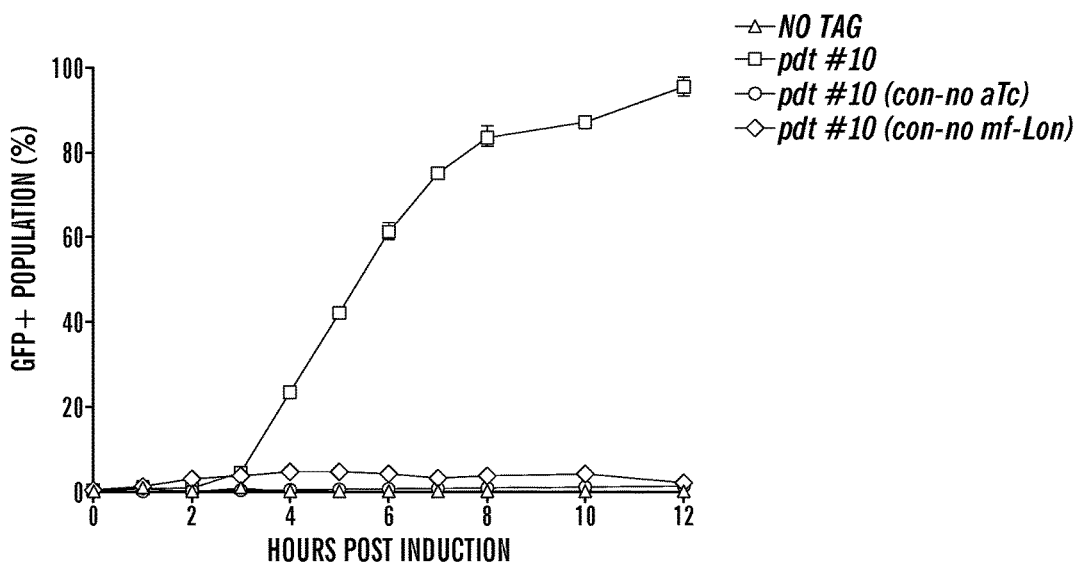
FIG. 8 depicts cells containing the toggle switch with the indicated tetR-pdt fusion were switched to the mCherry+ state with IPTG and allowed to stabilize in non-inducing media. Expression of mf-Lon was induced with 1 mM arabinose at 0 h, and the cells were monitored by flow cytometry for GFP and mCherry expression according to the parameters shown in FIG. 3B. A majority of cells that contained a tetR-pdt#10 fusion switched to the GFP+ state within 6 h of mf-Lon induction, while cells that contained the unmodified toggle switch (no tag) did not switch. Cells that contained the tetR-pdt#10 fusion but were not induced (no arabinose) or did not contain the mf-Lon expression plasmid also did not switch, demonstrating the specificity of mf-Lon mediated degradation of TetR-pdt#10. Error bars represent the mean±standard deviation (SD) of three biological replicates.

To test the degradation systems described herein in a synthetic circuit, pdt variants were incorporated into a genetic toggle switch based on reciprocal transcriptional repression[20]. As shown in FIG. 3A, LacI and TetR form a bistable circuit in which either LacI or TetR dominates, repressing transcription of the other to further enable its own expression. The repressors also control expression of the fluorescent reporters GFP and mCherry, allowing *facile* identification of the toggle switch state. To enable protease-based switching in the circuit, pdt#5 was fused to LacI and used flow cytometry to measure the switch rate and bistability of the toggle following mf-Lon expression from the arabinose-inducible $P_{BAD}$ promoter[21]. FIG. 3B shows that the circuit containing LacI-pdt#5 switched from the LacI+/GFP+ state to the TetR+/mCherry+ state within 8 h following mf-Lon induction, while the untagged circuit remained unchanged. Moreover, substitution of LacI-pdt#5 with the hybrid tags pdt#5A and pdt#5B caused delayed switching under identical induction conditions, as predicted from the GFP degradation data (FIG. 3C). Importantly, these LacI-pdt circuits remained bistable in the absence of mf-Lon induction (FIG. 7). Finally, fusion of pdt tags to TetR instead of LacI enabled protease-mediated switching to occur in the opposite direction (FIG. 8).

Tunable Control of Endogenous Bacterial Systems

Figure 4A:
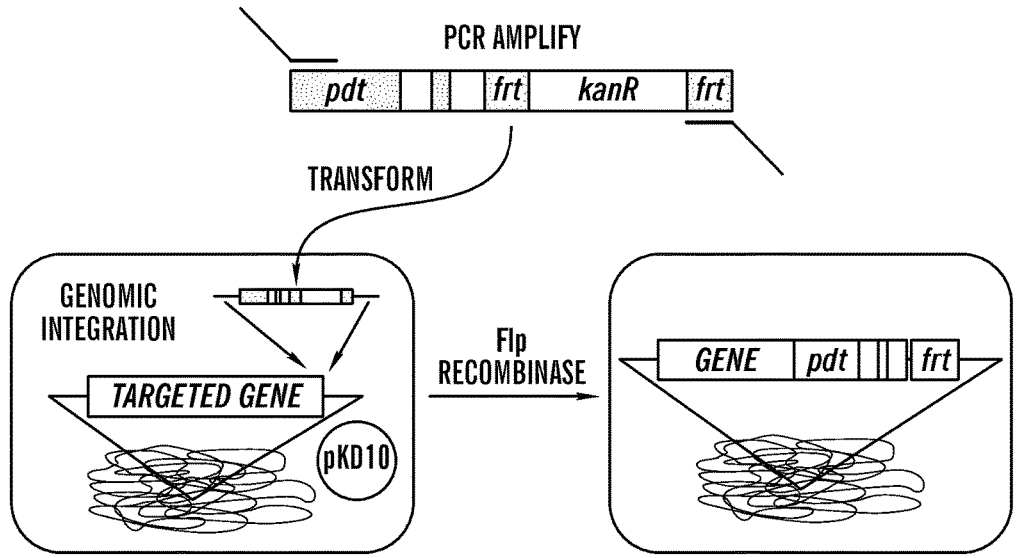
FIGS. 4A-4D demonstrate tunable control of endogenous bacterial systems.

A major goal of synthetic biology is to develop tools to control endogenous bacterial systems[22], so the inventors sought to determine if this degradation system could be used to control native genes that remain under natural transcriptional and translational regulation. As shown in FIG. 4A, a modified recombineering method[23,24] was used to insert pdt tags into the E. coli genome. Target genes involved in cell wall biosynthesis, cell division and chemotactic motility were selected because these cellular processes are well characterized and their disruption causes readily observable phenotypes.

Figure 4B:
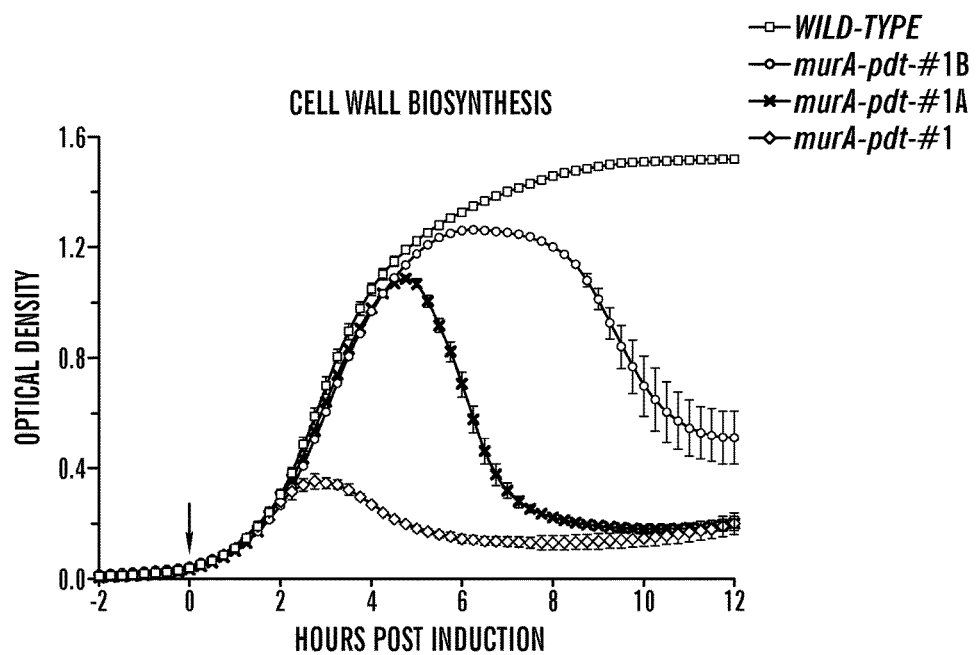
Figure 9A:
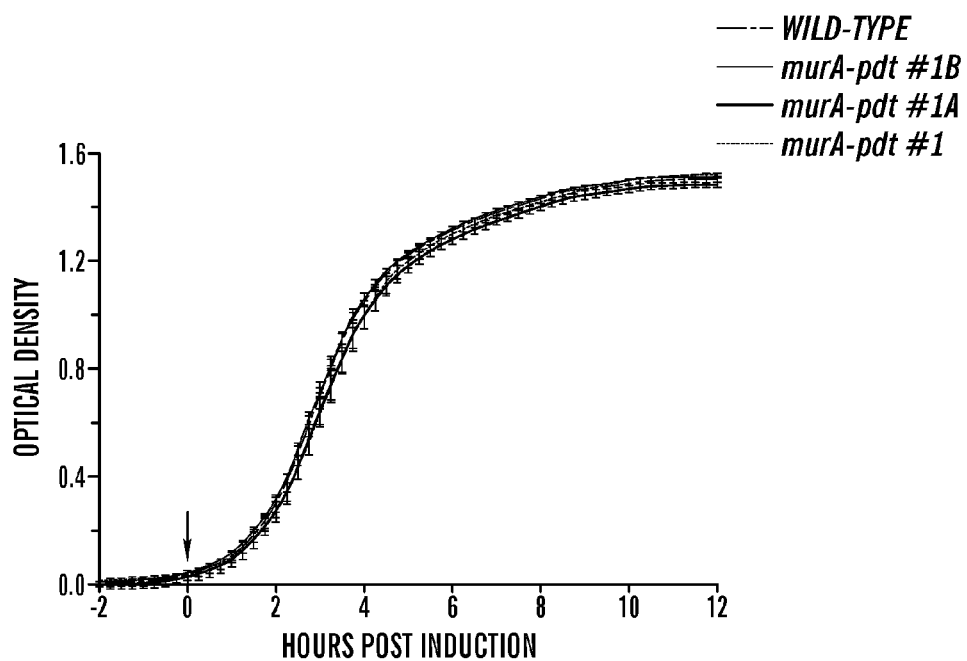
FIGS. 9A-9C depict endogenous protein degradation controls.
Figure 10:
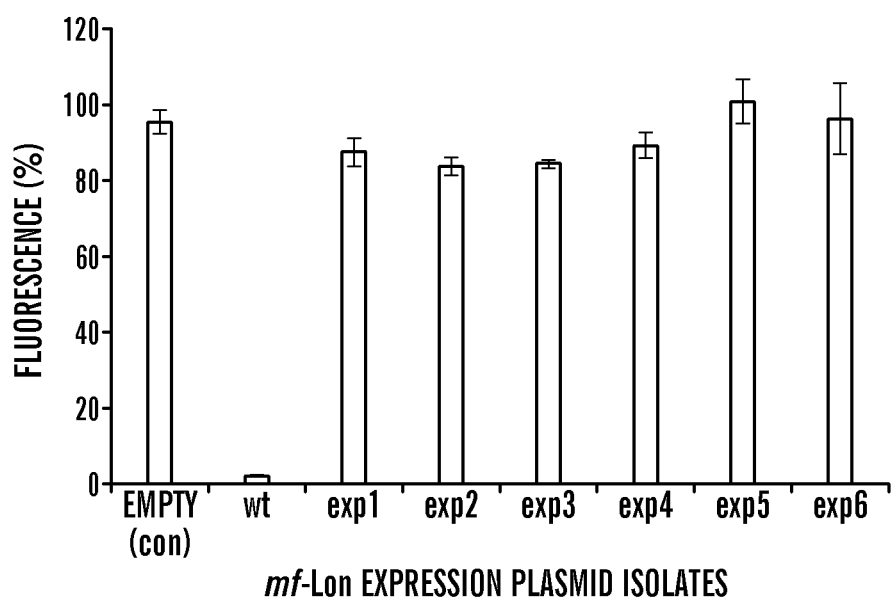
FIG. 10 depicts inactivating mutations in mf-Lon. A subset of cells with the murA-pdt#1 genomic insertion did not lyse and showed continued growth following mf-Lon induction, so individual surviving cells from six independent experiments were isolated and their mf-Lon expression plasmids were assayed for the ability to inducibly degrade GFP-pdt#5 in a new E. coli strain. In all six cases (exp1-exp6), the mf-Lon expression plasmid had lost nearly all proteolytic activity, allowing GFP-pdt#5 steady-state levels to remain high in contrast to the parental mf-Lon plasmid (wt) which reduced GFP to ~1% of non-induced levels. This indicates that the surviving cells escaped lysis through mutation of the mf-Lon plasmid and not mutation of the murA-pdt#1 fusion. Error bars represent the mean±standard deviation (SD) of three biological replicates.

MurA, an essential enzyme involved in peptidoglycan biosynthesis[25] whose depletion causes cell lysis measurable by a drop in optical density, was targeted first. FIG. 4B shows that the murA-pdt#1 genomic fusion caused cell lysis within 3 h of mf-Lon induction, while hybrid variants pdt#1A and pdt#1B caused delayed phenotypic responses that closely mimic those seen for pdt#5A and pdt#5B in the GFP degradation and toggle switch assays (see, for example, FIG. 2B and FIG. 3C). Importantly, cells containing MurA-pdt fusions show identical growth rates to wild-type bacteria in the absence of mf-Lon induction, demonstrating that the pdt variants do not interfere with MurA function (FIG. 9A). A subset of murA-pdt#5 cells grew despite mf-Lon induction, and isolates from six independent experiments all contained inactivating mutations in the mf-Lon expression plasmid (FIG. 10).

Figure 4C:
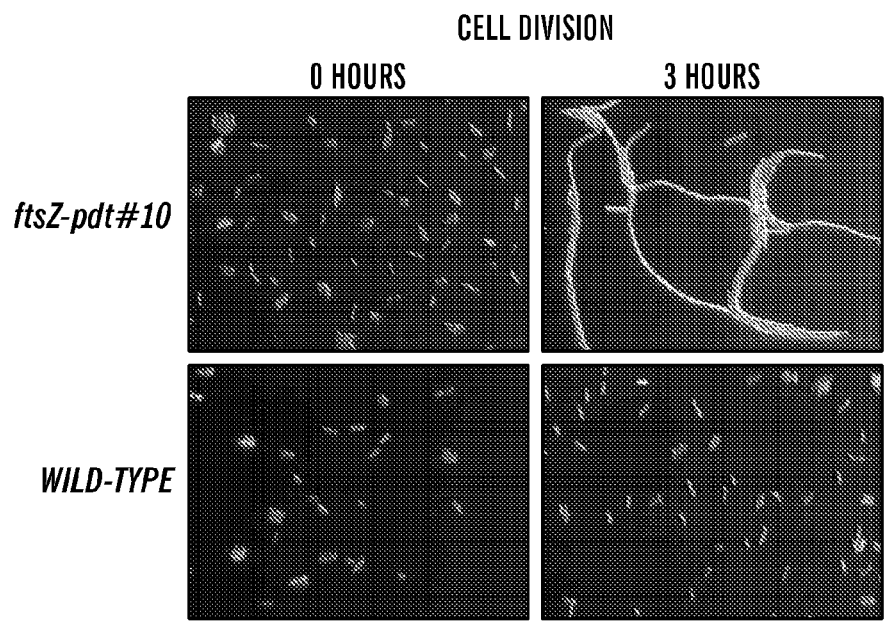
Figure 9B:
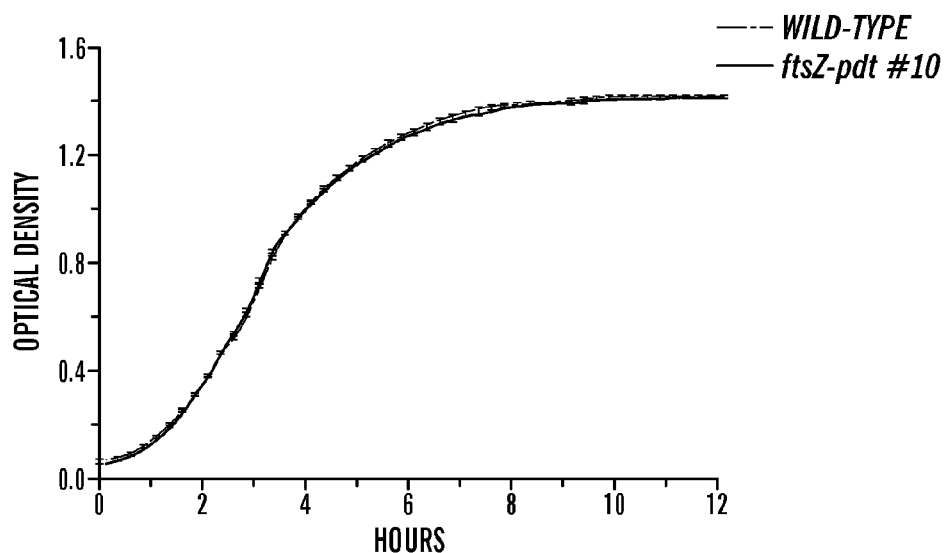
Figure 9C:
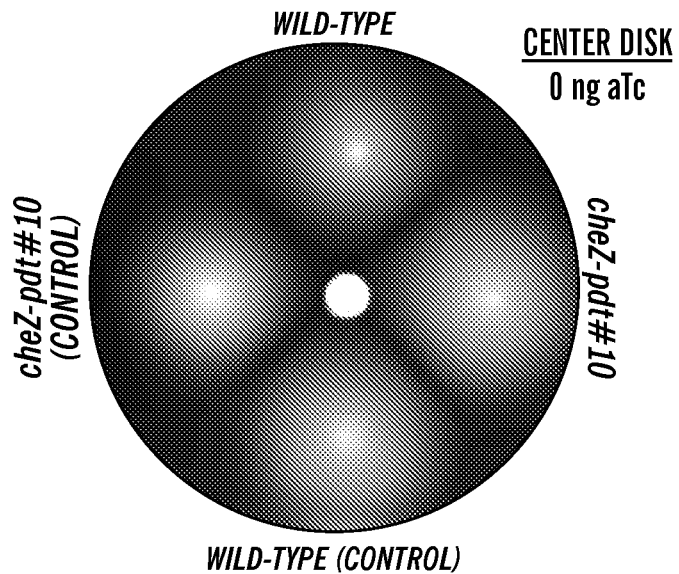

FtsZ, a tubulin homologue that forms the ring structure necessary for cell septation following genome replication,[26] was targeted next. As seen in FIG. 4C, mf-Lon expression caused distinct filamentation in ftsZ-pdt#10 cells but not wild-type cells within 3 h. The pdt#10 fusion had no discernible effect on FtsZ function under non-inducing conditions (0 h images), and its growth rate was identical to wild-type cells (FIG. 9B).

Figure 4D:
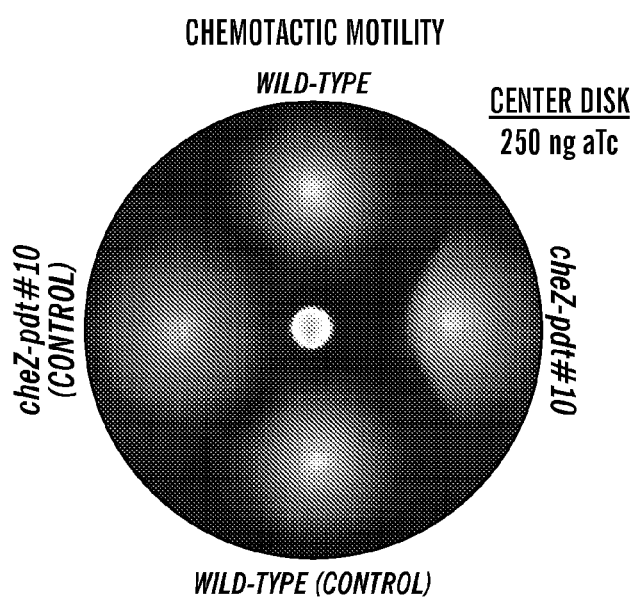

Last, we targeted CheZ, a member of the chemotaxis signaling system whose disruption prevents directed flagellar motility[27]. In a disk diffusion assay on motility agar, bacteria containing cheZ-pdt#10 lost chemotactic motility as they expressed mf-Lon upon exposure to the aTc gradient emanating from the center disk (FIG. 4D). Untagged bacteria (wild-type) and bacteria that did not express mf-Lon (control) maintained normal motility in the assay, confirming the specificity of aTc induced mf-Lon degradation of CheZ-pdt#10.

Figure 2D:
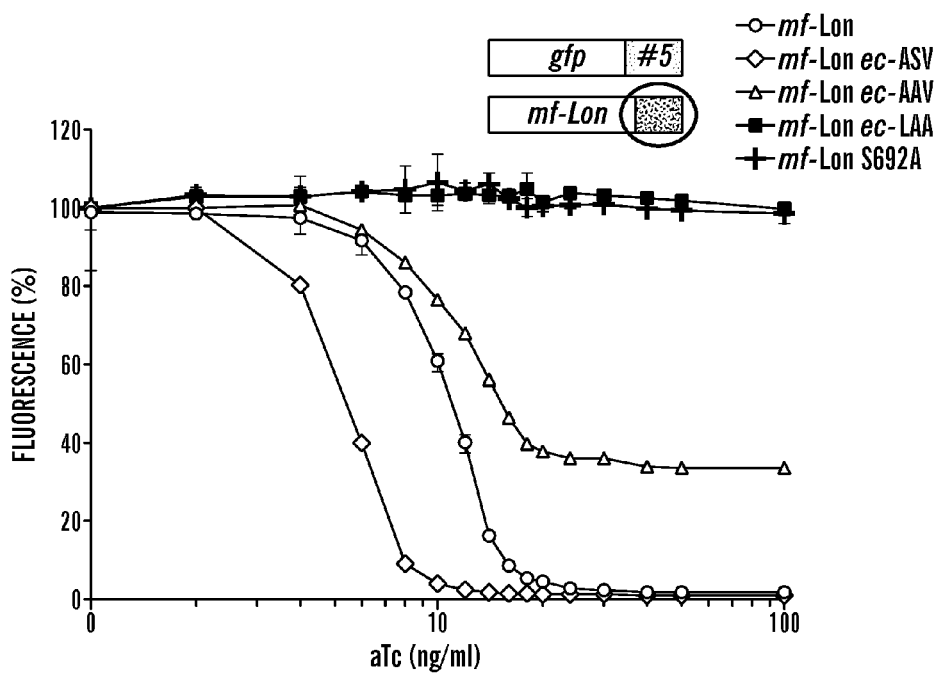

The synthetic degradation systems described herein are *facile* and modular, comprising a single protease gene and a small peptide tag that permit control over both the initial level and inducible degradation rate of attached proteins. The identified pdt variants described herein provide a 20-fold range of endogenous stability and up to 60-fold reduction in steady-state protein levels following mf-Lon induction. The relative instability of mf-Lon in E. coli inferred from the mf-Lon expression analysis indicates that both the degradation rate and final steady-state levels of pdt fusions can be readily improved by increasing mf-Lon expression and stability beyond that used in this study (FIG. 2D). The pdt mutagenesis screens were not saturating, so there are likely additional pdt variants with an expanded range of mf-Lon dependent degradation rates. Further, the N-terminal 13 amino acids of pdt are dispensable for in vitro degradation by mf-Lon[15], so it is possible to truncate tags that interfere with attached protein function, in some embodiments, without compromising mf-Lon recognition.

This degradation system represents an important advance in synthetic biology, where protein level control will provide an additional regulatory mechanism to aid in complex circuit design[28-32]. As demonstrated herein for a transcription-based toggle switch, existing synthetic circuitry can be readily modified with this system to enable post-translational control while leaving the original regulatory framework intact. Recent work by Huang et al.[33] also uses mf-Lon-mediated degradation to create a toggle switch, further demonstrating the utility of protease-driven control in synthetic systems. The system described herein can be used as a control mechanism in metabolic engineering[34-36] or as a tool to integrate multiple synthetic circuits[37,38].

The degradation systems described herein are dependent on transcriptional regulation to control mf-Lon expression, but the tripartite domain structure of mf-Lon[19,39] and the development of small molecule and light-induced domain interaction systems[40-42] indicate that, in some aspects and embodiments, post-translational control of mf-Lon activity can be used. For example, a similar approach was recently taken by Davis et al.[11] to enable rapamycin-induced protein degradation by ClpXP.

In some aspects, the technology described herein can be used in studying and controlling endogenous genetic systems. Single-step genomic insertion provides a simple and robust method to target pdt fusions to almost any E. coli gene. In the present study, genes in three distinct cellular pathways were targeted, and in each case the inserted pdt variants provided specific control over the targeted system without affecting function in the absence of mf-Lon expression. This ability to exert control over endogenous systems without rewiring the existing transcriptional regulatory networks can be used in a wide array of synthetic biology and bioengineering applications.

In some aspects, the pdt variants described herein can be used in studying essential genes whose cellular function and potential for targeted antibiotic development are major areas of research. Conventional methods for essential gene analysis use transcription or translation disruption and then rely on endogenous proteases to deplete the targeted protein, a passive process that depends on degradation dynamics that are unique to each protein[21,43,44]. In contrast, the pdt variants and systems thereof described herein specifically and actively target the essential protein for degradation, as shown for MurA and FtsZ. Like a similar system developed in M. smegmatis[45], in some aspects and embodiments, the pdt variants described herein can serve as a screening platform to identify essential genes that are most susceptible to degradation-induced cell death, an attractive phenotype for targeted antibiotic development. Post-translational control of mf-Lon activity can be particularly useful in such aspects and embodiments to minimize the time between induction and protein depletion. For identified protein targets, the pdt variants and systems thereof described herein enable precise control of steady-state protein levels, allowing targeted proteins to be inducibly degraded to levels that mimic chemical inhibition. Knowledge of the inhibition levels required to block protein function in vivo can aid in chemical biology design. The pdt variants and systems thereof described herein also offer chemical biologists a facile method to identify the phenotypes associated with targeted protein inhibition, in this case through degradation, before beginning the expensive and labor-intensive process of identifying potent protein-specific small-molecule inhibitors.

The pdt variants and systems thereof described herein are transferable to other bacteria outside of the highly divergent Mycoplasma genus that includes M. florum. Pdt and other Mycoplasma ssrA tags bear little resemblance to ssrA tags in any other sequenced bacteria[15], and Mycoplasma are the only organisms known to use Lon for targeted ssrA degradation, indicating that both pdt and mf-Lon will remain orthogonal in other Gram-negative and Gram-positive bacteria. Additional pdt number variants can be used to control degradation by endogenous proteases in these organisms, in some embodiments. The pdt variants and systems thereof described herein can also be transferred to eukaryotes such as S. cerevisiae, in some embodiments, where bacterial AAA+ proteases have been shown to retain ssrA-directed proteolytic activity[9].

TABLE 7

Protein degradation tag identification and characterization
(SEQ ID NOs: 1-26 in order of appearance)

| Name* | aa13-15** | aa24-27** | 0 ng/ml aTc | 50 ng/ml aTc | Fold Degradation |
|---|---|---|---|---|---|
| no tag | | | 100.00% | 86.9% | 1.2 |
| pdt | PTF | YAFA | 12.5% | 0.6% | 20.7 |
| pdt#1 | PTF | RLQL | 21.8% | 0.9% | 24.6 |
| pdt#2 | PTF | ICRL | 57.9% | 1.1% | 51.8 |
| pdt#3 | PTF | YLSQ | 73.1% | 1.2% | 61.8 |
| pdt#4 | PTF | YQYR | 85.7% | 1.7% | 51.0 |
| pdt#5 | PTF | RRRV | 102.0% | 2.1% | 48.7 |
| pdt#6 | PTF | HISP | 113.7% | 2.1% | 55.4 |
| pdt#7 | PTF | RICR | 133.8% | 4.2% | 31.7 |
| pdt#8 | PTF | HAQP | 143.8% | 3.0% | 48.4 |
| pdt#9 | PTF | RQRH | 171.5% | 10.1% | 17.0 |
| pdt#10 | PTF | RARQ | 226.7% | 5.5% | 41.5 |
| pdt#11 | PTF | FTQQ | 90.7% | 5.1% | 17.7 |
| pdt#12 | PTF | VVRR | 123.9% | 3.9% | 31.6 |
| pdt#13 | PTF | YRTP | 289.2% | 15.5% | 18.6 |
| pdt#S1 | PTF | RAQQ | 150.1% | 3.8% | 39.4 |
| pdt#S2 | PTF | RRQL | 158.7% | 3.6% | 44.9 |
| pdt#S3*** | PTF | QRQRQ | 99.8% | 2.6% | 38.7 |
| pdt#5A | RAI | RRRV | 98.9% | 18.4% | 5.4 |
| pdt#5B | APN | RRRV | 99.3% | 38.4% | 2.6 |
| pdt#5C | PDS | RRRV | 109.0% | 67.3% | 1.6 |
| pdt#5G | QPT | RRRV | 112.1% | 26.8% | 4.2 |
| pdt#5H | AQP | RRRV | 109.0% | 29.9% | 3.6 |
| pdt#5E | PSP | RRRV | 104.9% | 14.6% | 7.2 |
| pdt#5F | ERA | RRRV | 98.5% | 24.8% | 4.0 |
| pdt#5D | WLG | RRRV | 108.5% | 9.0% | 12.0 |

*S before number indicates that the pdt was forward engineeered (synthetic)
**aa indicates amino acid. The complete pdt tag amino acid sequence is here (targeted regions are underlined): AANKNEENTNEVPTFMLNAGQANYAFA?
***amino acids 23-27 were mutated in this pdt variant Methods Strain Construction. MG1655ΔlacIΔaraBAD was created through P1 phage transduction of lacI:kan from the Keio collection into MG1655 (ATCC no. 47076), and Red-recombinase mediated single-step homologous recombination was used to create the in-frame deletion of araBAD according to methods described previously. Flp recombinase was used to remove the kan$^r$ cassette in each case. DH5αλpir was used for cloning. The in-frame protease deletions were constructed by P1 phage transduction of the corresponding mutations from the Keio collection into MG1655pro, followed by kan$^r$ cassette removal as detailed above.

Plasmids. GFP-pdt variants were cloned into pZE21-MCS using KpnI and HindIII restriction sites, and the constitutive P$_{lacIq}$ promoter was inserted using the XhoI and KpnI sites. KpnI and HindIII sites were used to clone mf-lon into pZA11-MCS following removal of an internal HindIII site in mf-lon. For the toggle switch experiments, the PLtetO promoter in this plasmid was replaced with PBAD using the XhoI and KpnI sites. To generate pECT, the kan$^r$ cassette and surrounding FRT sites was PCR amplified from pKD131 and cloned into pWM915 using MluI and XhoI. PDT tag variants were cloned into pECT using XhoI and SacII, and were named according to the inserted pdt tag (e.g., pECT5A contains pdt#5A). Plasmid pECA102, Flp recombinase was cloned into pBAD24 using KpnI to make pBAD24-Flp, and the constitutively expressed sac cassette was subsequently cloned from pWM91 into pBAD24-Flp using partial MluI and SalI digestion and ligation. For the toggle switch experiments, lacI-pdt fusions were cloned into pKDL071-RBS8 using BsrGI and SacII. Plasmids were verified by sequencing and are deposited in GenBank.

Genomic insertion of PDT variants. PDT variants were amplified from their cognate pECT plasmid using primers P1 and P2 that contained additional 42 base 5' extensions with homology

P1:
(SEQ ID NO: 104)
GCGGCGAACAAAAACGAA

P2:
(SEQ ID NO: 105)
GGGGATCCGTCGACCTGC.

-continued

P1-murA
(SEQ ID NO: 106)
CTGCGCGCTTTAGGTGCAAATATTGAGCGTGTGAAAGGCGAAGCGGCGAA

CAAAAACGAA

P2-murA:
(SEQ ID NO: 107)
CTGGCGGTAGCCCCGCGAACGGGGCTGCCAGCTCTCAGACGAGGGGATCC

GTCGACCTGC

P1-ftsZ:
(SEQ ID NO: 108)
GATTATCTGGATATCCCAGCATTCCTGCGTAAGCAAGCTGATGCGGCGAA

CAAAAACGAA

P2-ftsZ:
(SEQ ID NO: 109)
GTTTAGCACAAAGAGCCTCGAAACCCAAATTCCAGTCAATTCGGGGATCC

GTCGACCTGC

P1-cheZ:
(SEQ ID NO: 110)
AGTCAGGATCAGGTGGACGATTTGTTGGATAGTCTTGGATTTGCGGCGAA

CAAAAACGAA

P2-cheZ:
(SEQ ID NO: 111)
CCGCCTGATATGACGTGGTCACGCCACATCAGGCAATACAAAGGGGATCC

GTCGACCTGC

Strains, Plasmids and Reagents. The *E. coli* K-12 derivative strain MG1655Pro (F-, λ-, Sp$^r$, lacI, tetR) published previously[1,46] was used as the wild-type strain in all cases except for the synthetic toggle experiments where MG1655ΔlacIΔaraBAD was prepared and used as described herein. Unless otherwise noted, bacteria were grown in Luria broth (LB) at 30° with shaking and mf-Lon expression was induced with 50 ng/ml aTc. Antibiotics carbenicillin (100 ug/ml) and kanamycin (30 ug/ml) were added to the media when appropriate. All plasmids and strain mutations were verified by sequencing, and plasmid maps will be deposited in GenBank.

GFP Degradation Platform. The GFP variant GFPmut3b[47] was used for all GFP expression. GFP-pdt variants were expressed from the constitutive $P_{lacIq}$ promoter[48] on a high-copy plasmid containing the ColE1 origin and a kanamycin-resistance cassette. The $P_{LtetO}$ promoter was used to express mf-Lon on a medium-copy plasmid containing the P15A origin and ampicillin-resistance cassette.

Flow Cytometry. GFP expression was measured using a FACSARIAII (BD BIOSCIENCES) flow cytometer with the following voltage settings: FCS, 340; SCS, 270; FITC (for GFP), 520; mCherry, 615. At least 10,000 cells were collected for each measurement and FloJo was used for data analysis.

Plate Fluorimetry and Optical Density. Fluorescence and optical density measurements were made with a SPECTRAMAX M5 microplate reader (MOLECULAR DEVICES) using excitation and emission wavelengths of 488 nm and 520 nm, respectively, with an emission filter cutoff at 515 nm Optical density was measured at 600 nm (OD600). All measurements were made in 200 μl in 96-well clear bottom plates.

PDT Mutagenesis Screens. Polymerase chain reaction (PCR) primers containing randomized nucleotides were used to mutagenize the indicated pdt codons. Plasmids containing the mutagenized tags fused to gfp were co-transformed with the mf-Lon expression plasmid into MG1655Pro. Transformants were picked into 96-well plates, grown to mid-log phase, diluted 1:20 into media with and without 50 ng/ml aTc and measured by plate reader after 10 h growth. Strains that exhibited the desired GFP degradation dynamics were further characterized by flow cytometry.

Synthetic Toggle Switch. The toggle switch plasmid pKDL071-RBS8, which served as the parental toggle switch, was generated by PCR mutagenesis of pKDL071 to contain an altered tetR ribosome binding site (RBS) that enhanced toggle bistability in the minimal media conditions used. Variants of lacI-pdt were generated by PCR and cloned into pKDL071-RBS8. The mf-Lon expression plasmid used in the GFP degradation platform was modified for use with the toggle switch by replacing the $P_{LtetO}$ promoter with the $P_{BAD}$ promoter to allow arabinose-induced expression. Cells containing the toggle switch and mf-Lon expression plasmids were grown in 200 μl in 96-well round bottom plates at 37° in M9 minimal media containing 0.2% glycerol and 0.05% casamino acids, and care was taken to maintain logarithmic growth throughout the experiment. Cells were grown for 6 h with either 30 ng/ml aTc or 500 μM Isopropyl β-D-1-thiogalactopyranoside (IPTG) to induce cells into the GFP+ or mCherry+ states, respectively. Cells were diluted 1:1000 into non-inducing media and allowed to grow for an additional 12 h. To induce mf-Lon, cells were grown at 37° shaking with or without 1 mM arabinose and then passaged every 4 h (~1:10 dilution) into media containing the same inducing conditions. At each time point, 40 μl were fixed with 1% paraformaldehyde in PBS and stored at 4° for up to 5 days. Cells that did not contain the toggle switch circuit were used to define the GFP and mCherry states shown in FIG. 3B.

Genomic Insertion of pdt Variants. Plasmid pECT was created to serve as a template for PCR amplification of the pdt variant cassettes shown in FIG. 4A. The inventors cloned the kanamycin-resistance cassette and surrounding FRT sites from pKD13[49] into pWM91[50] to generate pECT, which was further named according to the pdt tag variant cloned adjacent to the upstream FRT site (e.g., pECT-5A contains pdt#5A). To generate PCR products for genomic integration, PDT variants were amplified from their cognate pECT plasmid using primers P1 and P2 that contained additional 42 base 5' extensions with homology to the C-terminus and immediate 3' untranslated region (UTR) of the targeted gene, respectively. PCR products were electroporated into competent MG1655Pro cells containing pKD46 using published methods_ENREF_23[23], and successful genomic pdt insertions were verified by PCR following selection on kanamycin. To remove the kan$^r$ cassette, Flp recombinase was expressed from the $P_{BAD}$ promoter in pECA102, and the plasmid was subsequently cured by selection on LB agar plates containing 10% sucrose. A detailed description of the primers and plasmid construction is found herein.

MurA-Induced Lysis Growth Conditions. Strains were grown in 200 μl LB in 96-well round bottom plates with a lid at 30° shaking in a SPECTRAMAX M5 plate reader. OD600 measurements were taken every 15 minutes and normalized using media-only wells. Wells on the perimeter of the plate were filled with water and not used for bacterial growth.

FtsZ Microscopy. Differential interference contrast (DIC) and fluorescence microscopy images were taken with a Nikon ECLIPSE TI microscope using a 100× objective and a COLDSNAP HQ2 CCD camera (Photometrics) operated with NIS-Elements Advanced Research 3.2 software. For images of ftsZ-pdt filamentation, cells in mid-log growth in liquid cultures were induced with 50 ng/ml aTc, grown for 3 h at 30°, placed on a 300 µl pad containing PBS and 0.75% low-melt agarose (Boston Bioproducts) and immediately imaged.

Chemotactic Motility Plates. Cells in mid-log growth were stabbed into soft agar plates containing 1% tryptone, 0.5% NaCl and 0.3% agar. ATc dissolved in 5 µl water was added to sterile 6 mm disks in the center of the plates immediately prior to bacterial inoculation. Plates were incubated for 18 h at 30° before imaging with a GEL LOGIC 6000 PRO (Carestream).

REFERENCES

1. Lutz, R. & Bujard, H. Independent and tight regulation of transcriptional units in *Escherichia coli* via the LacR/O, the TetR/O and AraC/I1-I2 regulatory elements. Nucleic Acids Res 25, 1203-1210 (1997).
2. Isaacs, F. J. et al. Engineered riboregulators enable post-transcriptional control of gene expression. Nat Biotechnol 22, 841-847 (2004).
3. Topp, S. et al. Synthetic riboswitches that induce gene expression in diverse bacterial species. Applied and environmental microbiology 76, 7881-7884 (2010).
4. Lucks, J. B., Qi, L., Mutalik, V. K., Wang, D. & Arkin, A. P. Versatile RNA-sensing transcriptional regulators for engineering genetic networks. Proceedings of the National Academy of Sciences of the United States of America 108, 8617-8622 (2011).
5. Callura, J. M., Cantor, C. R. & Collins, J. J. Genetic switchboard for synthetic biology applications. Proceedings of the National Academy of Sciences of the United States of America 109, 5850-5855 (2012).
6. Moore, S. D. & Sauer, R. T. The tmRNA system for translational surveillance and ribosome rescue. Annu Rev Biochem 76, 101-124 (2007).
7. Janssen, B. D. & Hayes, C. S. The tmRNA ribosome-rescue system. Adv Protein Chem Struct Biol 86, 151-191 (2012).
8. Andersen, J. B. et al. New unstable variants of green fluorescent protein for studies of transient gene expression in bacteria. Appl Environ Microbiol 64, 2240-2246 (1998).
9. Gritty, C., Stricker, J., Pang, W. L., Bennett, M. R. & Hasty, J. A synthetic gene network for tuning protein degradation in *Saccharomyces cerevisiae*. Mol Syst Biol 3, 127 (2007).
10. Flynn, J. M., Neher, S. B., Kim, Y. I., Sauer, R. T. & Baker, T. A. Proteomic discovery of cellular substrates of the ClpXP protease reveals five classes of ClpX-recognition signals. Mol Cell 11, 671-683 (2003).
11. Davis, J. H., Baker, T. A. & Sauer, R. T. Small-molecule control of protein degradation using split adaptors. ACS Chem Biol 6, 1205-1213 (2011).
12. Neklesa, T. K. et al. Small-molecule hydrophobic tagging-induced degradation of HaloTag fusion proteins. Nat Chem Biol 7, 538-543 (2011).
13. Banaszynski, L. A., Chen, L. C., Maynard-Smith, L. A., Ooi, A. G. & Wandless, T. J. A rapid, reversible, and tunable method to regulate protein function in living cells using synthetic small molecules. Cell 126, 995-1004 (2006).
14. Bonger, K. M., Chen, L. C., Liu, C. W. & Wandless, T. J. Small-molecule displacement of a cryptic degron causes conditional protein degradation. Nat Chem Biol 7, 531-537 (2011).
15. Gur, E. & Sauer, R. T. Evolution of the ssrA degradation tag in *Mycoplasma*: specificity switch to a different protease. Proc Natl Acad Sci USA 105, 16113-16118 (2008).
16. Flynn, J. M. et al. Overlapping recognition determinants within the ssrA degradation tag allow modulation of proteolysis. Proc Natl Acad Sci USA 98, 10584-10589 (2001).
17. Ge, Z. & Karzai, A. W. Co-evolution of multipartite interactions between an extended tmRNA tag and a robust Lon protease in *Mycoplasma*. Mol Microbiol 74, 1083-1099 (2009).
18. Botos, I. et al. The catalytic domain of *Escherichia coli* Lon protease has a unique fold and a Ser-Lys dyad in the active site. The Journal of biological chemistry 279, 8140-8148 (2004).
19. Sauer, R. T. & Baker, T. A. AAA+ proteases: ATP-fueled machines of protein destruction. Annual review of biochemistry 80, 587-612 (2011).
20. Gardner, T. S., Cantor, C. R. & Collins, J. J. Construction of a genetic toggle switch in *Escherichia coli*. Nature 403, 339-342 (2000).
21. Guzman, L. M., Belin, D., Carson, M. J. & Beckwith, J. Tight regulation, modulation, and high-level expression by vectors containing the arabinose PBAD promoter. Journal of bacteriology 177, 4121-4130 (1995).
22. Moon, T. S. et al. Construction of a genetic multiplexer to toggle between chemosensory pathways in *Escherichia coli*. J Mol Biol 406, 215-227 (2011).
23. Datsenko, K. A. & Wanner, B. L. One-step inactivation of chromosomal genes in *Escherichia coli* K-12 using PCR products. Proc Natl Acad Sci USA 97, 6640-6645 (2000).
24. Sharan, S. K., Thomason, L. C., Kuznetsov, S. G. & Court, D. L. Recombineering: a homologous recombination-based method of genetic engineering. Nat Protoc 4, 206-223 (2009).
25. Brown, E. D., Vivas, E. I., Walsh, C. T. & Kolter, R. MurA (MurZ), the enzyme that catalyzes the first committed step in peptidoglycan biosynthesis, is essential in *Escherichia coli*. Journal of bacteriology 177, 4194-4197 (1995).
26. Adams, D. W. & Errington, J. Bacterial cell division: assembly, maintenance and disassembly of the Z ring. Nat Rev Microbiol 7, 642-653 (2009).
27. Silversmith, R. E. Auxiliary phosphatases in two-component signal transduction. Curr Opin Microbiol 13, 177-183 (2010).
28. Lu, T. K., Khalil, A. S. & Collins, J. J. Next-generation synthetic gene networks. Nat Biotechnol 27, 1139-1150 (2009).
29. Weber, W. & Fussenegger, M. Emerging biomedical applications of synthetic biology. Nat Rev Genet 13, 21-35 (2012).
30. Rodrigo, G., Landrain, T. E. & Jaramillo, A. De novo automated design of small RNA circuits for engineering synthetic riboregulation in living cells. Proceedings of the National Academy of Sciences (2012).
31. Tabor, J. J. et al. A synthetic genetic edge detection program. Cell 137, 1272-1281 (2009).
32. Pedraza, J. M. & van Oudenaarden, A. Noise propagation in gene networks. Science 307, 1965-1969 (2005).

33. Huang, D. C., Holtz, W. J. & Maharbiz, M. M. A genetic bistable switch utilizing nonlinear protein degradation. J Biol Eng 6, 9 (2012).
34. Fung, E. et al. A synthetic gene-metabolic oscillator. Nature 435, 118-122 (2005).
35. Tan, C., Marguet, P. & You, L. Emergent bistability by a growth-modulating positive feedback circuit. Nature chemical biology 5, 842-848 (2009).
36. Agapakis, C. M. & Silver, P. A. Modular electron transfer circuits for synthetic biology: insulation of an engineered biohydrogen pathway. Bioeng Bugs 1, 413-418 (2010).
37. Danino, T., Mondragon-Palomino, O., Tsimring, L. & Hasty, J. A synchronized quorum of genetic clocks. Nature 463, 326-330 (2010).
38. Slusarczyk, A. L., Lin, A. & Weiss, R. Foundations for the design and implementation of synthetic genetic circuits. Nat Rev Genet 13, 406-420 (2012).
39. Li, M. et al. Structure of the N-terminal fragment of *Escherichia coli* Lon protease. Acta Crystallogr D Biol Crystallogr 66, 865-873 (2010).
40. Levskaya, A. et al. Synthetic biology: engineering *Escherichia coli* to see light. Nature 438, 441-442 (2005).
41. Kennedy, M. J. et al. Rapid blue-light-mediated induction of protein interactions in living cells. Nat Methods 7, 973-975 (2010).
42. Spencer, D. M., Wandless, T. J., Schreiber, S. L. & Crabtree, G. R. Controlling signal transduction with synthetic ligands. Science 262, 1019-1024 (1993).
43. Goh, S., Boberek, J. M., Nakashima, N., Stach, J. & Good, L. Concurrent growth rate and transcript analyses reveal essential gene stringency in *Escherichia coli*. PLoS One 4, e6061 (2009).
44. Herring, C. D. & Blattner, F. R. Conditional lethal amber mutations in essential *Escherichia coli* genes. J Bacteriol 186, 2673-2681 (2004).
45. Wei, J. R. et al. Depletion of antibiotic targets has widely varying effects on growth. Proc Natl Acad Sci USA 108, 4176-4181 (2011).
46. Callura, J. M., Dwyer, D. J., Isaacs, F. J., Cantor, C. R. & Collins, J. J. Tracking, tuning, and terminating microbial physiology using synthetic riboregulators. Proc Natl Acad Sci USA 107, 15898-15903 (2010).
47. Cormack, B. P., Valdivia, R. H. & Falkow, S. FACS-optimized mutants of the green fluorescent protein (GFP). Gene 173, 33-38 (1996).
48. Muller-Hill, B., Crapo, L. & Gilbert, W. Mutants that make more lac repressor. Proc Natl Acad Sci USA 59, 1259-1264 (1968).
49. Baba, T. et al. Construction of *Escherichia coli* K-12 in-frame, single-gene knockout mutants: the Keio collection. Molecular systems biology 2, 2006 0008 (2006).
50. Metcalf, W. W. et al. Conditionally replicative and conjugative plasmids carrying lacZ alpha for cloning, mutagenesis, and allele replacement in bacteria. Plasmid 35, 1-13 (1996).
51. Baba, T. et al. Construction of *Escherichia coli* K-12 in-frame, single-gene knockout mutants: the Keio collection. Molecular systems biology 2, 2006 0008 (2006).
52. Datsenko, K. A. & Wanner, B. L. One-step inactivation of chromosomal genes in *Escherichia coli* K-12 using PCR products. Proc Natl Acad Sci USA 97, 6640-6645 (2000).
53. Metcalf, W. W., Jiang, W. & Wanner, B. L. Use of the rep technique for allele replacement to construct new *Escherichia coli* hosts for maintenance of R6K gamma origin plasmids at different copy numbers. Gene 138, 1-7 (1994).
54. Lutz, R. & Bujard, H. Independent and tight regulation of transcriptional units in *Escherichia coli* via the LacR/O, the TetR/O and AraC/I1-I2 regulatory elements. Nucleic Acids Res 25, 1203-1210 (1997).
55. Metcalf, W. W. et al. Conditionally replicative and conjugative plasmids carrying lacZ alpha for cloning, mutagenesis, and allele replacement in bacteria. Plasmid 35, 1-13 (1996).
56. Guzman, L. M., Belin, D., Carson, M. J. & Beckwith, J. Tight regulation, modulation, and high-level expression by vectors containing the arabinose PBAD promoter. Journal of bacteriology 177, 4121-4130 (1995).

Example 2

Platform for Post-Translational Control of Bacterial Systems

Summary Tunable control of protein degradation in bacteria can expand the genetic tool set available to develop synthetic gene circuits and probe natural cellular systems. Here the inventors use components of the *Mesoplasma florum* tmRNA system to create a synthetic degradation system that provides tunable control of targeted proteins in *Escherichia coli*. The inventors identify degradation tag variants with independent control of both the steady-state level and inducible degradation rate of attached proteins, and demonstrate their use in synthetic circuit development and exogenous control of core bacterial processes, including peptidoglycan biosynthesis, cell division and chemotactic motility. The inventors demonstrate the system's ability to induce target-specific hypersensitivity to antibiotics and thereby serve as the basis of a screening assay for target-specific inhibitors. Moreover, the system displays broad functionality in bacteria, showing strong targeted degradation in *Lactococcus lactis*, a Gram-positive bacterium. The synthetic degradation system is *facile* and modular, requiring only a small peptide tag and a single protease gene, does not require disruption of host systems, and can be transferred to diverse bacteria with minimal modification.

Exogenous control of protein biosynthesis through transcriptional and translational regulation is well established[1-7], but robust and tunable control of protein degradation in bacteria was elusive. Controlled protein degradation can provide biologists with the ability to probe gene function without disrupting the transcriptional and translational regulation that control its expression, and it can provide biological engineers with an additional regulatory tool to develop more complex synthetic gene circuits. Targeted protein degradation in bacteria occurs in part through the tmRNA system which uses the small peptide ssrA to direct proteins to the endogenous ClpXP and ClpAP proteases for rapid degradation[8]. Variants of the *E. coli* ssrA tag (ec-ssrA) are commonly used to modify the degradation rate of attached proteins in bacteria[9] and recently in eukaryotes[10], but these tags do not provide inducible control of degradation. Recent inducible eukaryotic systems rely on degradation machinery not present in bacteria[11-13], and bacterial systems such as the one developed by Davis et al.[14] often require disruption of the endogenous tmRNA system and are not easily transferred to other organisms.

Here the inventors present a synthetic degradation system, based on the Gram-positive *M. florum* tmRNA system, that does not rely on host degradation systems and can function in a wide range of bacteria. Gur and Sauer[15] showed that the *M. florum* ssrA tag (mf-ssrA) is degraded by its endogenous Lon protease (mf-Lon) but not by *E. coli* Lon or ClpXP, and mf-Lon does not recognize or degrade ec-ssrA, providing a protease and cognate degradation tag with orthogonal functionality in *E. coli*.

Figure 11A:
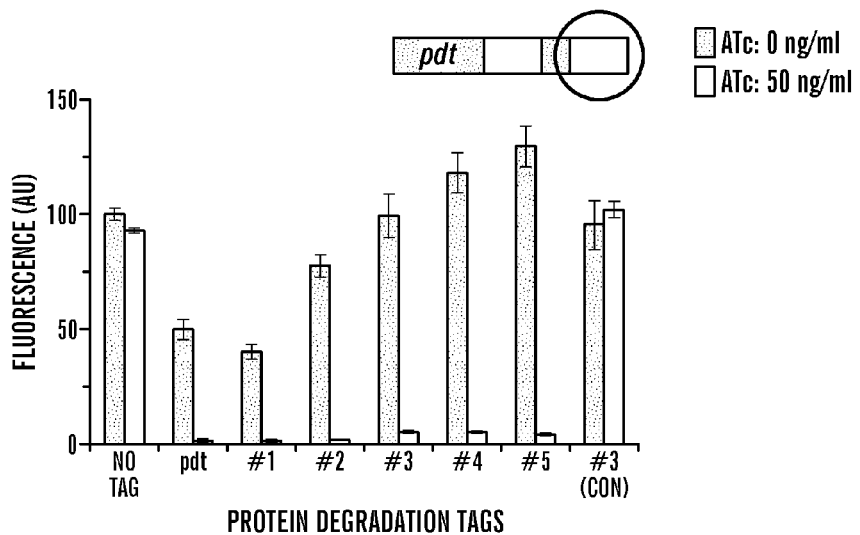
FIGS. 11A-11D show characterization of protein degradation tags.
Figure 14A:
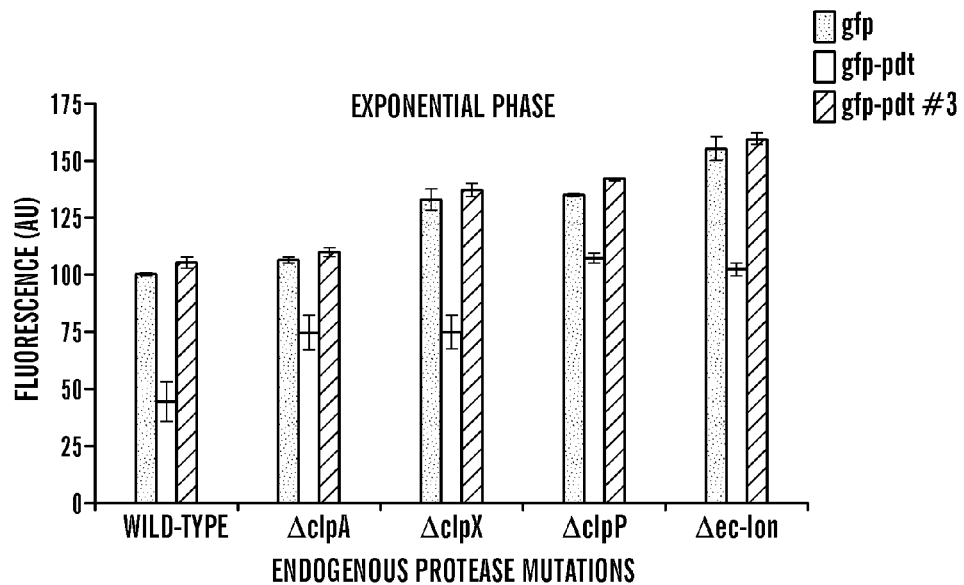
FIGS. 14A-14B show GFP-pdt degradation by endogenous E. coli proteases.
Figure 14B:
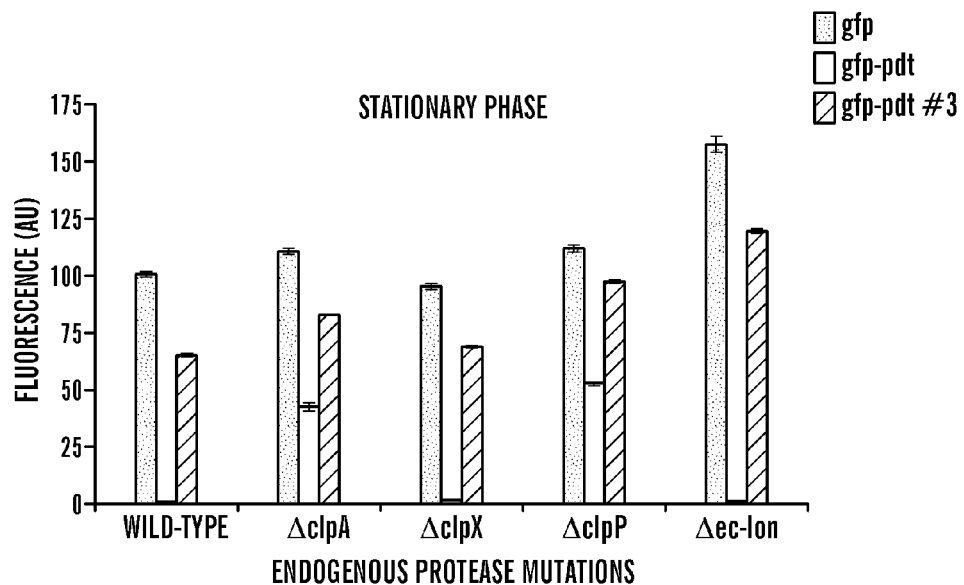

As noted above, the inventors renamed the mf-ssrA tag "pdt" (protein degradation tag) to minimize confusion with the *E. coli* ssrA tag, and incorporated it into a GFP-based test platform for inducible protein degradation in *E. coli* (FIG. 1a). To first engineer pdt variants that alter steady-state GFP levels in the absence of mf-Lon expression, the inventors chose to target pdt residues[24-27] for mutagenesis due to the region's partial homology with the ec-ssrA ClpA binding site[16] and altered GFP-pdt stability in clpA, clpX, and clpP deletion strains (FIGS. 1B, 14A, and 14B). As seen in FIG. 11A, the inventors identified several pdt variants, denoted with numbers, that alter GFP steady-state levels and maintained near wild-type GFP degradation rates following mf-Lon expression. Importantly, untagged GFP remained largely unaffected by mf-Lon expression while hewild-type GFP-pdt fusion was reduced to 3% of its initial levels, confirming the specificity of pdt-mediated mf-Lon degradation seen by Gur and Sauer for LacZ degradation[15]. Sequence analysis of the identified pdt number variants showed that a majority contained multiple arginine and glutamine residues in the mutagenized region and none contained negatively charged residues known to disrupt mf-Lon recognition[15] (Table 3).

Figure 11B:
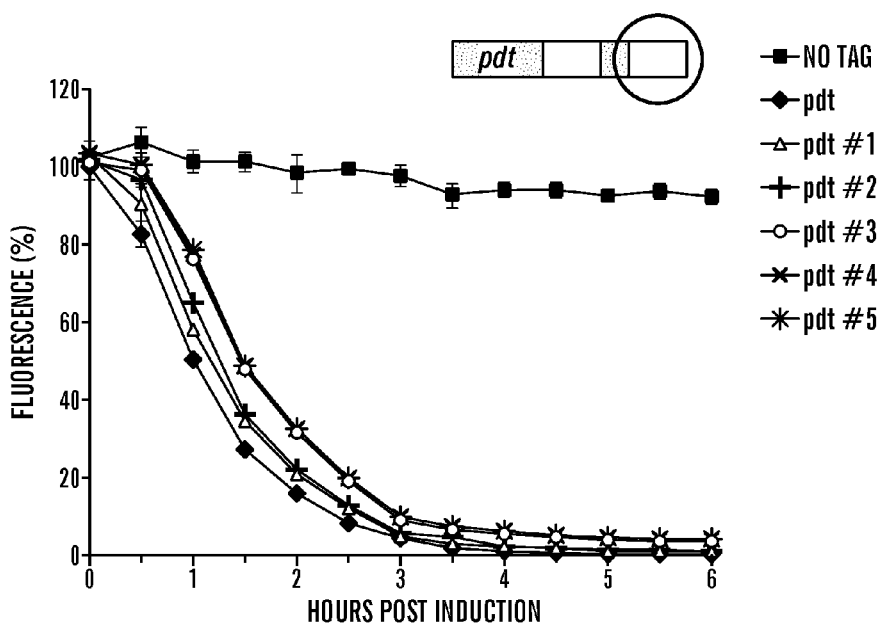
Figure 15:
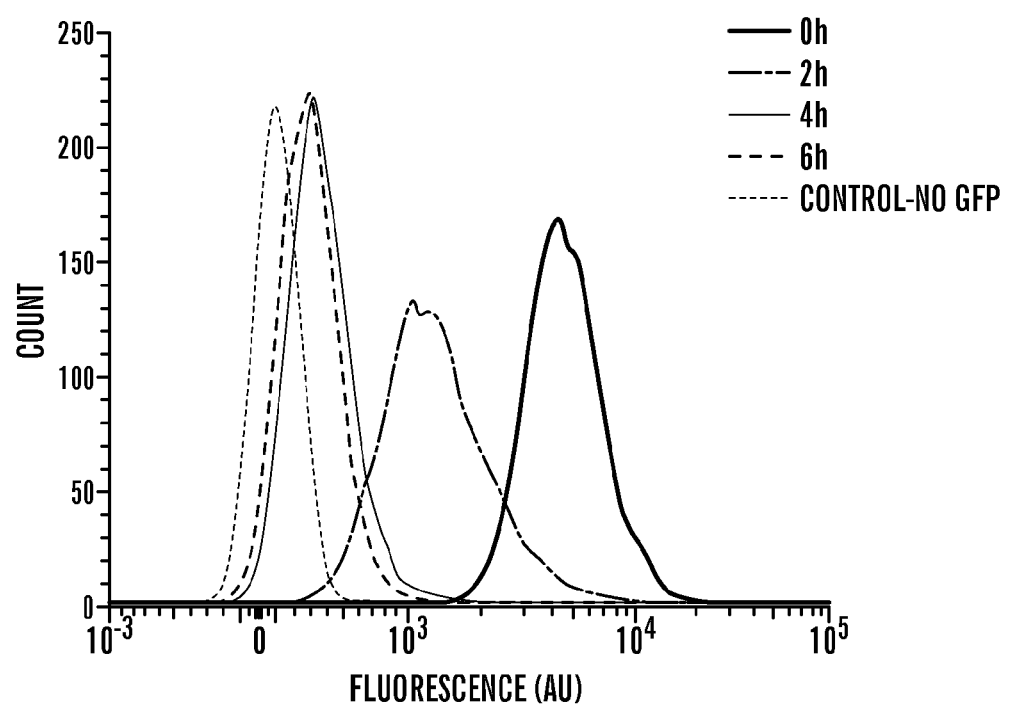
FIG. 15 shows population level degradation dynamics. Cells in exponential phase growth that constitutively express GFP-pdt#3 were induced to express mf-Lon (50 ng/ml ATc), and GFP fluorescence was measured by flow cytometry at the indicated time post induction. The histogram plot shows a monomodal shift in the cell population over time.

The inventors used flow cytometry to further characterize mf-Lon-mediated GFP-pdt degradation and found that the pdt number variants displayed temporal degradation dynamics similar to wild-type pdt, reducing GFP levels to 1-5% of initial levels within 4 hours (FIG. 11B). GFP degradation did not occur in the absence of either mf-Lon or the pdt tag, and the tight monomodal shift in the fluorescent population distribution showed that degradation occurred across all cells in the experimental population (FIG. 15).

Figure 11C:
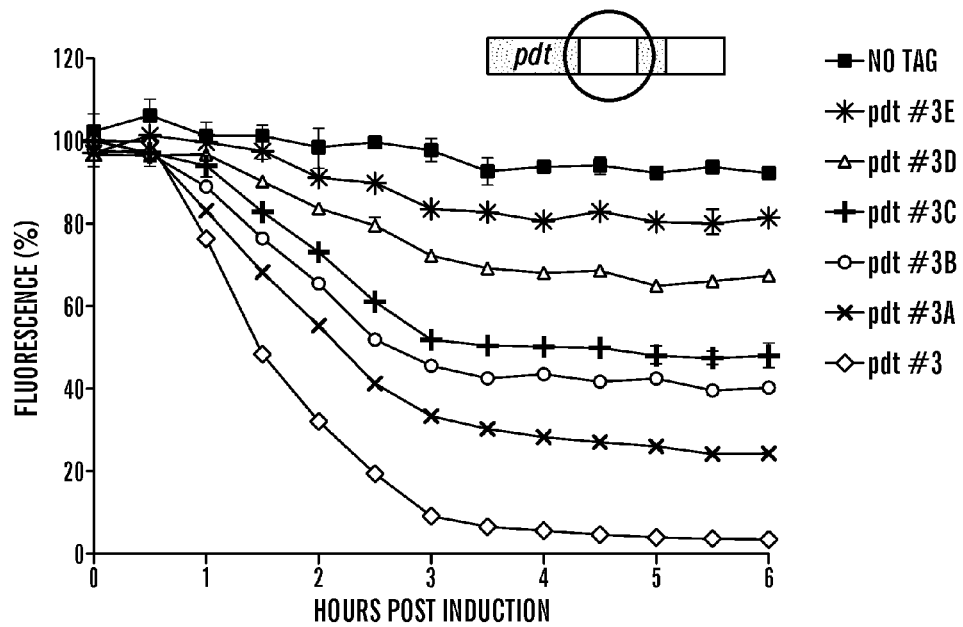

The inventors next sought to identify pdt variants (denoted with letters) that alter mf-Lon dependent degradation but not recognition by endogenous *E. coli* proteases. The inventors used GFP-pdt#3 as the parental tag and targeted pdt residues[13-15] for mutagenesis because the region is essential for Lon-mediated degradation in *Mycoplasma pneumoniae*[17] and has no homology to known ClpA, ClpX or SspB binding sites[16]. Pdt variants that maintained steady-state GFP levels and displayed a range of mf-Lon dependent degradation rates are shown in FIG. 11C.

Figure 11D:
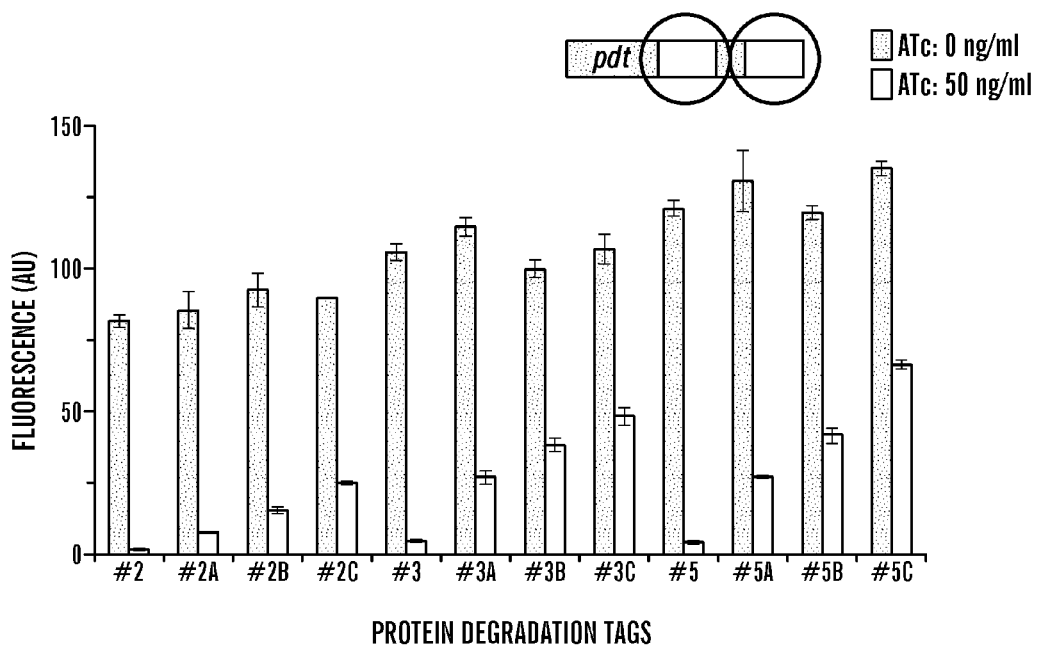

To determine if these letter variants could be combined with other number variants to produce hybrid tags with predictable control over both the steady-state protein level and induced degradation rate, the inventors created a panel of hybrid pdt variants and measured GFP fluorescence in the presence and absence of mf-Lon induction. When combined with the number variants pdt#2 and pdt#5, the letter variants displayed the same rank order of degradation rates that were initially identified using pdt#3 (FIG. 11D). In the absence of mf-Lon induction, the hybrid pdt variants also showed steady-state levels that largely conformed to the level dictated by the number variant used, although there was significant variation in some hybrid tag combinations indicating partial recognition of the letter variant region by *E. coli* proteases.

Figure 12A:
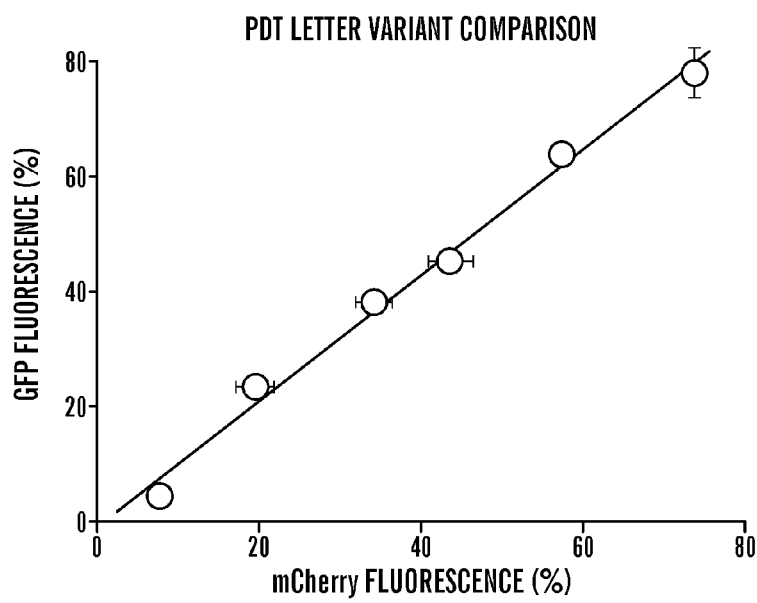
FIGS. 12A-12D show pdt system characterization.
Figure 16A:
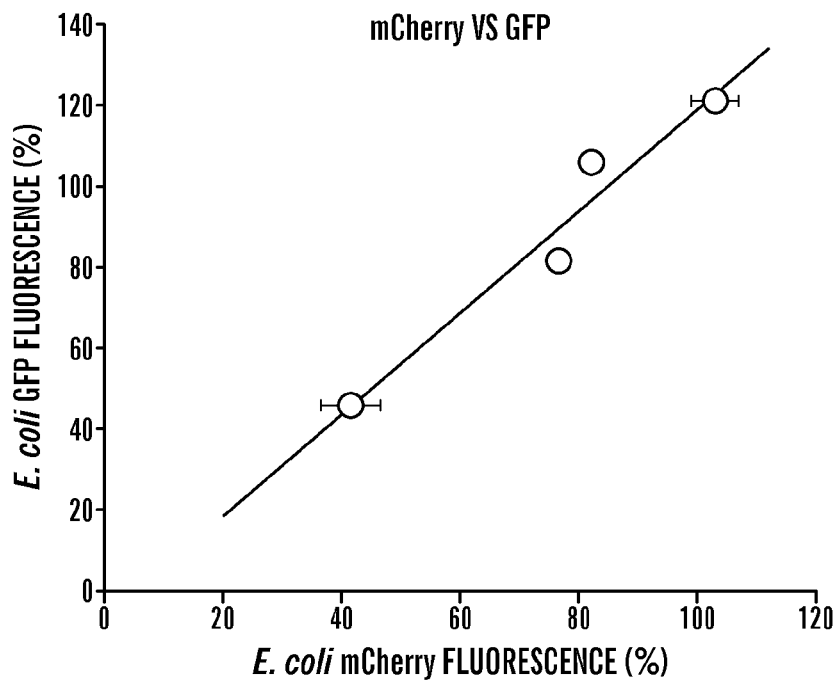
FIGS. 16A-16B show pdt number variant comparisons. Pdt number variants were fused to GFP and mCherry as indicated. Fluorescence was measured by flow cytometry without mf-Lon induction and is presented as a percent of the fluorescence of the untagged protein target.

To determine if this GFP-pdt characterization can be used to predict pdt mediated degradation of other protein targets in *E. coli*, the inventors placed the pdt variants on mCherry, a structurally unrelated fluorescent protein, and measured degradation following mf-Lon induction. As seen in FIG. 12A, the letter variants produced mCherry degradation dynamics that correlated strongly with GFP degradation, displaying a simple linear regression with an $R^2$ value of 0.99. The slope of the regression line (1.09) and its y-intercept (−0.01) indicate that mf-Lon-mediated degradation of GFP and mCherry occurred at similar rates for all pdt letter variants tested. Pdt number variants also showed strong correlation for mCherry and GFP, with a linear regression $R^2$ value of 0.95 (FIG. 16A).

Figure 12B:
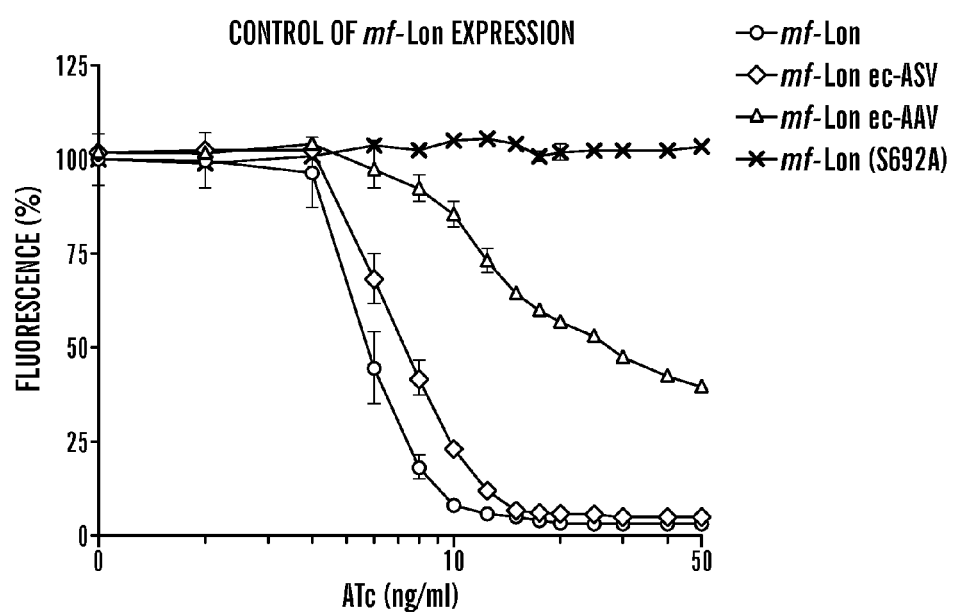
Figure 12C:
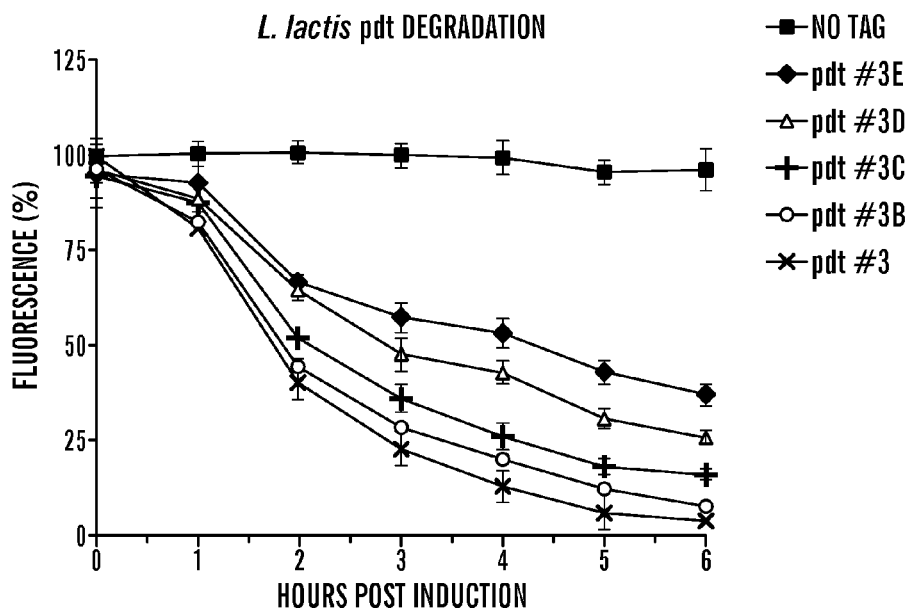
Figure 12D:
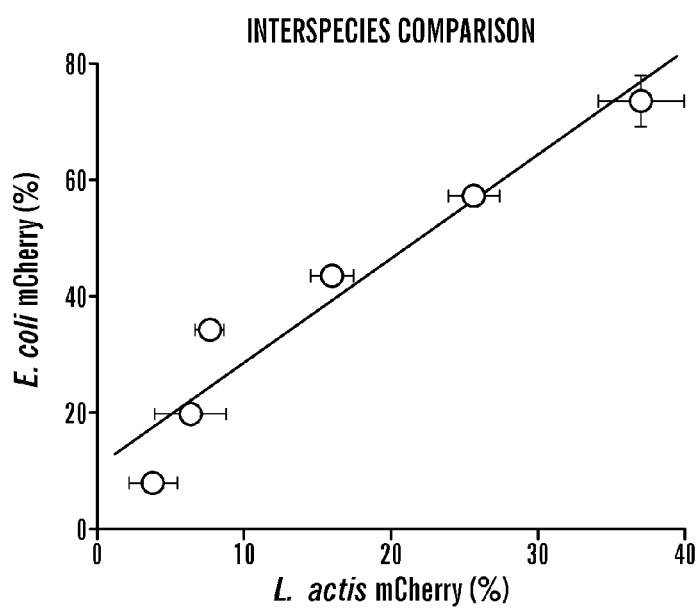
Figure 16B:
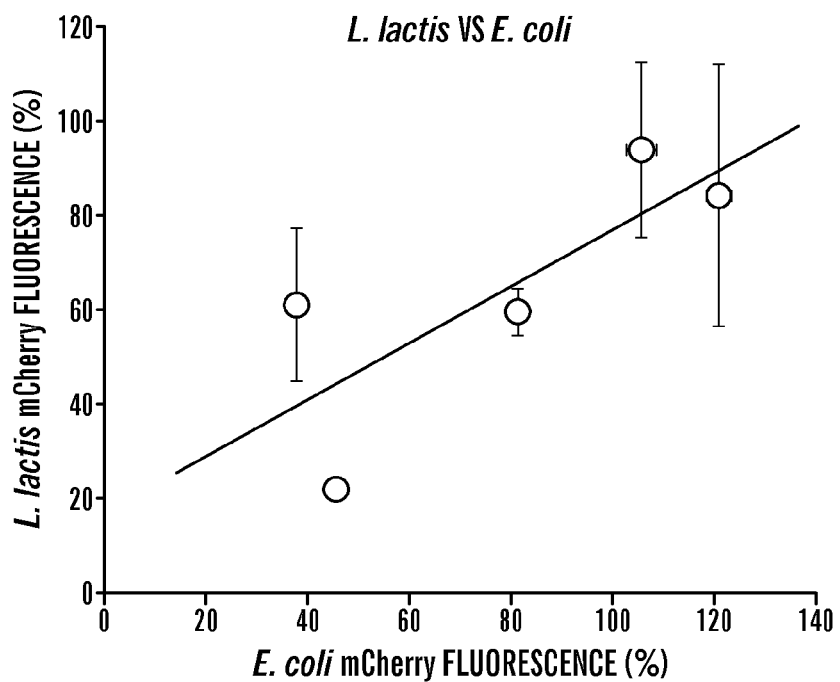

To determine if this targeted degradation system functions in other bacteria, the inventors transferred the inducible protease and pdt variants to *Lactococcus lactis*, an industrially important Gram-positive bacterium that is phylogenetically distant from *E. coli*, a Gram-negative bacterium. The inventors codon-optimized mf-lon for expression in *L. lactis* and placed the gene under control of the nisin inducible promoter PnisA[18]. As seen in FIG. 12C, inducible mf-Lon expression in *L. lactis* resulted in efficient pdt-mediated degradation of mCherry, and the relative degradation strength of the pdt letter variants in *L. lactis* correlated well with their corresponding strength in *E. coli* ($R^2$=0.92) (FIG. 12D). As expected for pdt number variants that were chosen for their altered recognition by *E. coli* specific proteases, their effect on mCherry steady state levels in *L. lactis* showed only weak correlation to *E. coli* (FIG. 16B).

Targeted protein degradation is dependent not only on the target protein and the pdt variant but also on mf-Lon expression levels, providing an additional mechanism to control target protein levels. As shown in FIG. 12B, transcriptional control of mf-Lon, based on anhydrotetracycline (ATc) induction of the PLtetO promoter, provided a well-defined range mf-Lon expression levels, as defined by targeted GFP-pdt#3 degradation. To enable post-translational control of mf-Lon, the inventors fused variants of the ec-ssrA tag to mf-Lon and measured their effect on GFP-pdt#3 degradation. The ec-AAV variant caused a significant shift in inducible mf-Lon protein levels, resulting in reduced GFP-pdt#3 degradation throughout the range of ATc levels tested, while the weaker ec-ASV variant had only a small effect on mf-Lon protein levels. An inactivating mutation in the conserved active site of the mf-Lon proteolytic domain (S692A)[19] fully blocked mf-Lon mediated GFP-pdt#3 degradation.

To demonstrate the use of this system to control engineered genetic circuits, the inventors used pdt fusions to provide post-translational control of a transcription-based toggle switch[20]. LacI and TetR form a bistable circuit based on reciprocal repression, and concomitant regulation of GFP and mCherry allows *facile* fluorescence-based identification of the toggle switch state. The inventors fused pdt#3 to the C-terminus of LacI in the toggle circuit and used the arabinose-inducible PBAD promoter[1] to drive mf-Lon expression from a second plasmid. Flow cytometry indicates that the circuit containing LacI-pdt#3 switched from the LacI+/GFP+ state to the TetR+/mCherry+ state within 8 hours of mf-Lon induction, while the untagged circuit remained unchanged. Moreover, substitution of LacI-pdt#3 with the hybrid tags pdt#3A and pdt#3B provided temporal control over the circuit switch rate, and pdt fusions to TetR enabled mf-Lon to switch the toggle in the opposite direction (FIG. 8 and data not shown). Importantly, the LacI-pdt circuits maintained transcription-based bistability in the absence of mf-Lon induction, demonstrating the ability of the system to leave existing regulatory networks intact (FIG. 7 and data not shown).

Figure 13A:
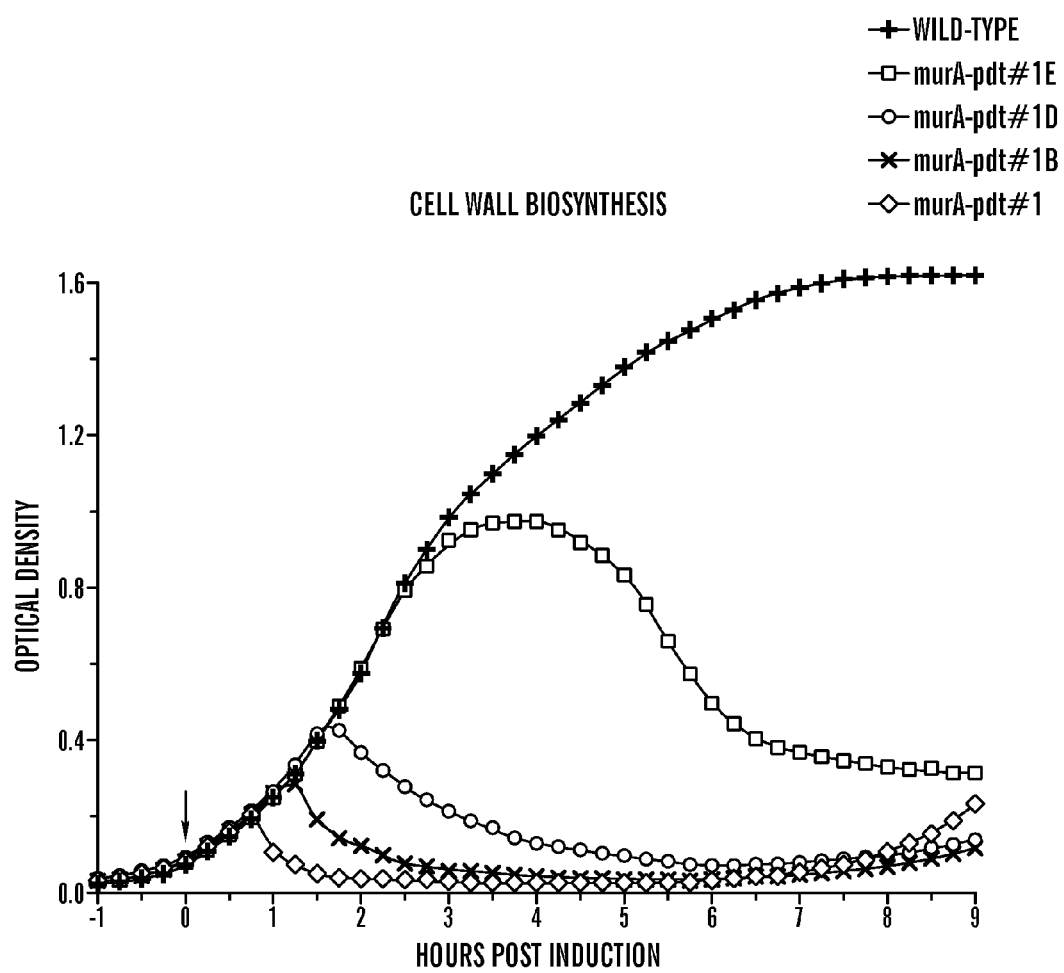
FIGS. 13A-13E show tunable control of endogenous bacterial systems.
Figure 17:
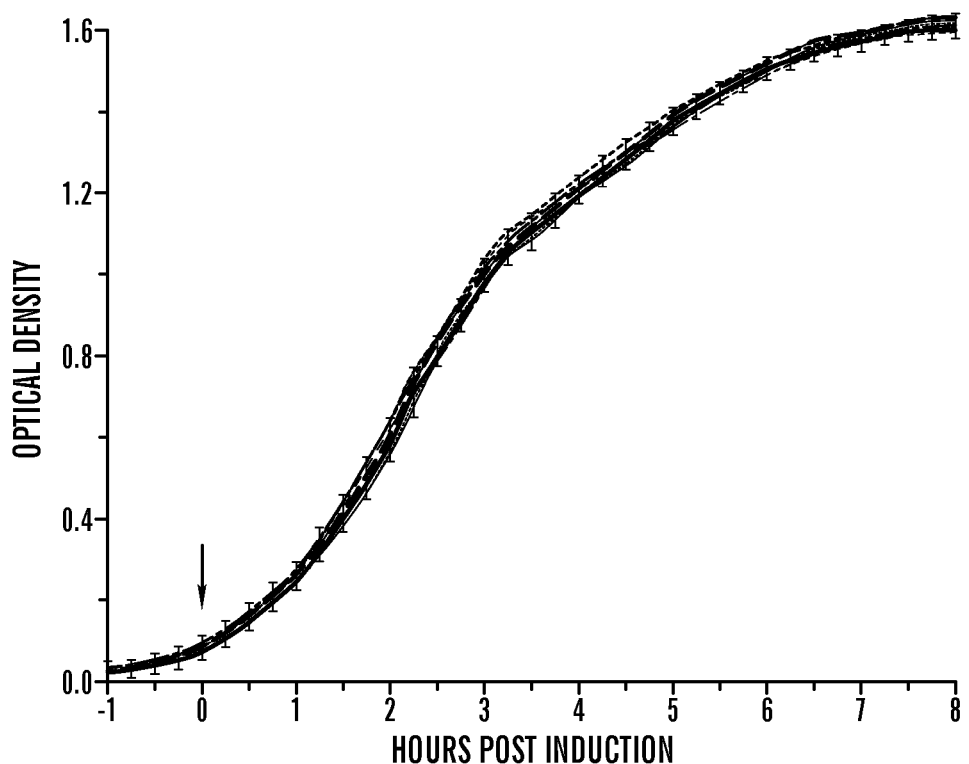
FIG. 17 shows the growth of murA-pdt cells in the absence of mf-Lon induction. The growth rate of cells containing the indicated pdt variants, with or without mf-Lon and with or without ATc induction as indicated, are indistinguishable from wild-type cells as measured by optical density (600 nm). The growth rate of *E. coli* containing ftsZ-pdt#5 was indistinguishable from wild-type cells in the absence of mf-Lon induction.

A major goal in microbial biotechnology is to develop tools to control and manipulate endogenous bacterial systems[21], so the inventors next sought to target native *E. coli* pathways for control by the system described herein. The inventors chose to target genes involved in cell wall biosynthesis, cell division and chemotactic motility because these processes are well characterized and produce readily observable phenotypes. As shown in FIG. 4A, the inventors developed a modified recombineering method to insert pdt tags into the E. coli genome[22,23], and began by targeting MurA, an essential enzyme involved in peptidoglycan biosynthesis[24] whose depletion causes cell lysis measurable by a drop in optical density. The murA-pdt#1 genomic fusion caused observable cell lysis 45 minutes after mf-Lon induction (FIG. 13A), and the delayed phenotypic response of the hybrid variants pdt#1A and pdt#1B closely mimicked the temporal delay seen for letter variants in the toggle switch and GFP degradation assays (see FIG. 12D). Importantly, cells containing murA-pdt fusions show identical growth rates to wild-type cells in the absence of mf-Lon induction, demonstrating that the pdt variants do not interfere with MurA function or regulation (FIG. 17A).

Figure 13B:
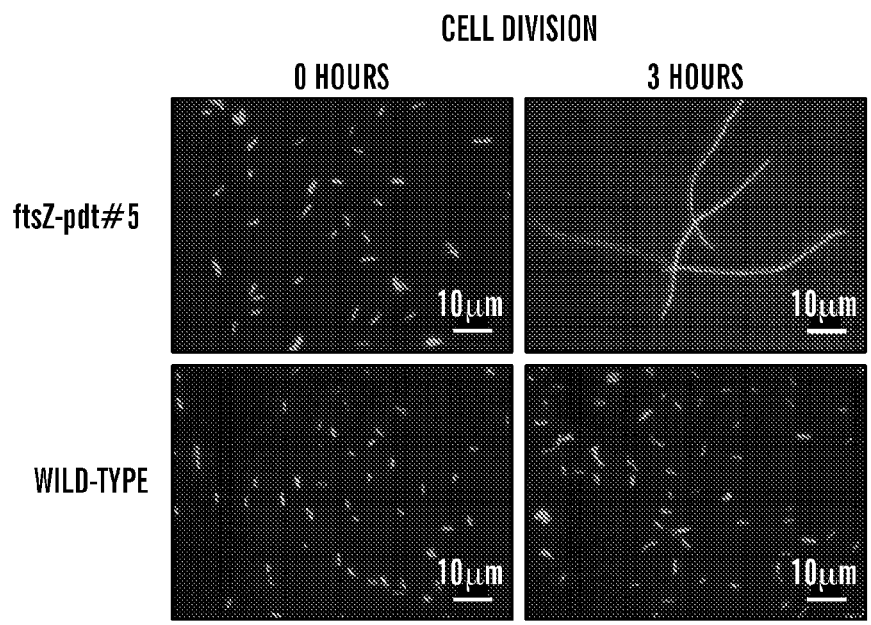
Figure 13C:
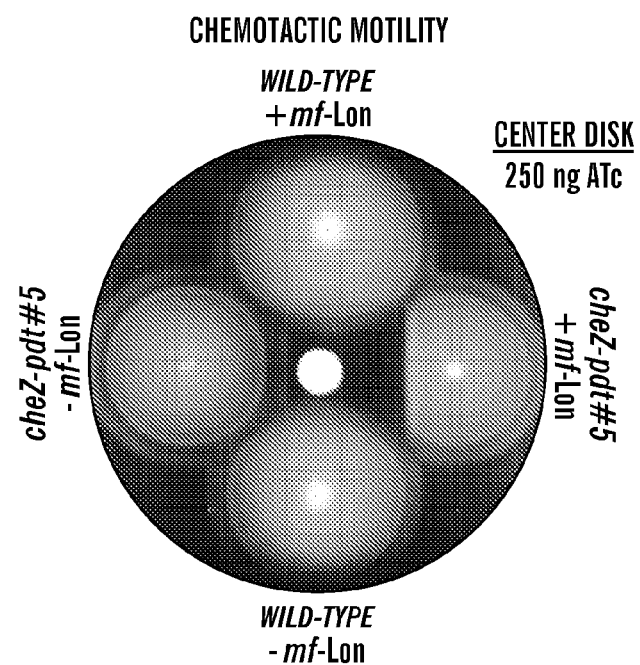

The inventors next targeted FtsZ, a tubulin homologue that forms the ring structure necessary for cell septation following genome replication[25]. As seen in FIG. 13B, mf-Lon induction caused distinct filamentation in ftsZ-pdt#5 cells but not wild-type cells within 3 hours of ATc induction. The pdt#5 fusion had no discernible effect on FtsZ function under non-inducing conditions (0 hour images), and its growth rate was identical to wild-type cells (FIG. 9B and data not shown). The inventors then targeted CheZ, a member of the chemotaxis signaling system whose disruption prevents directed flagellar motility[26]. In a disk diffusion assay on motility agar, mf-Lon induction by an ATc gradient from the center disk caused bacteria containing cheZ-pdt#5 to lose chemotactic motility (FIG. 13C). Bacteria that did not contain the cheZ-pdt#5 fusion or did not express mf-Lon maintained normal chemotactic motility, confirming the specificity of ATc induced mf-Lon degradation of CheZ-pdt#5.

Figure 13D:
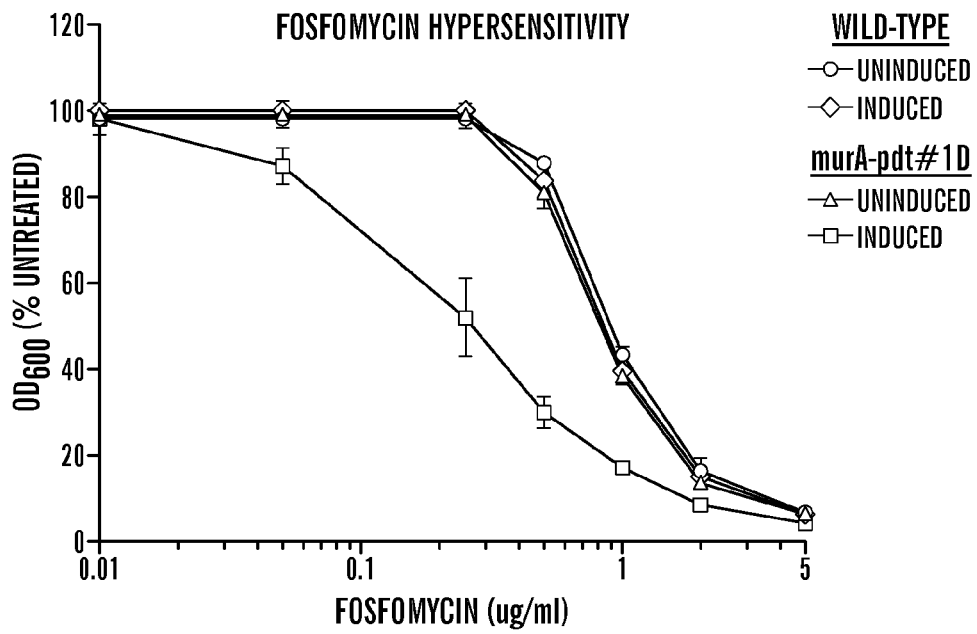
Figure 13E:
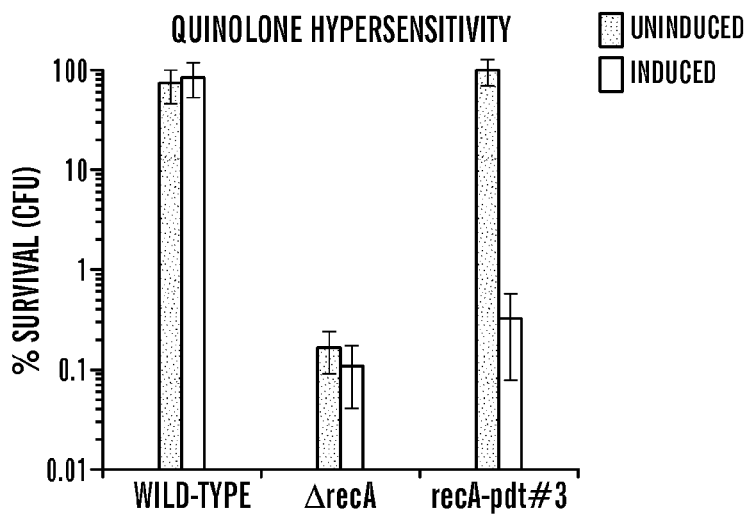
Figure 18:
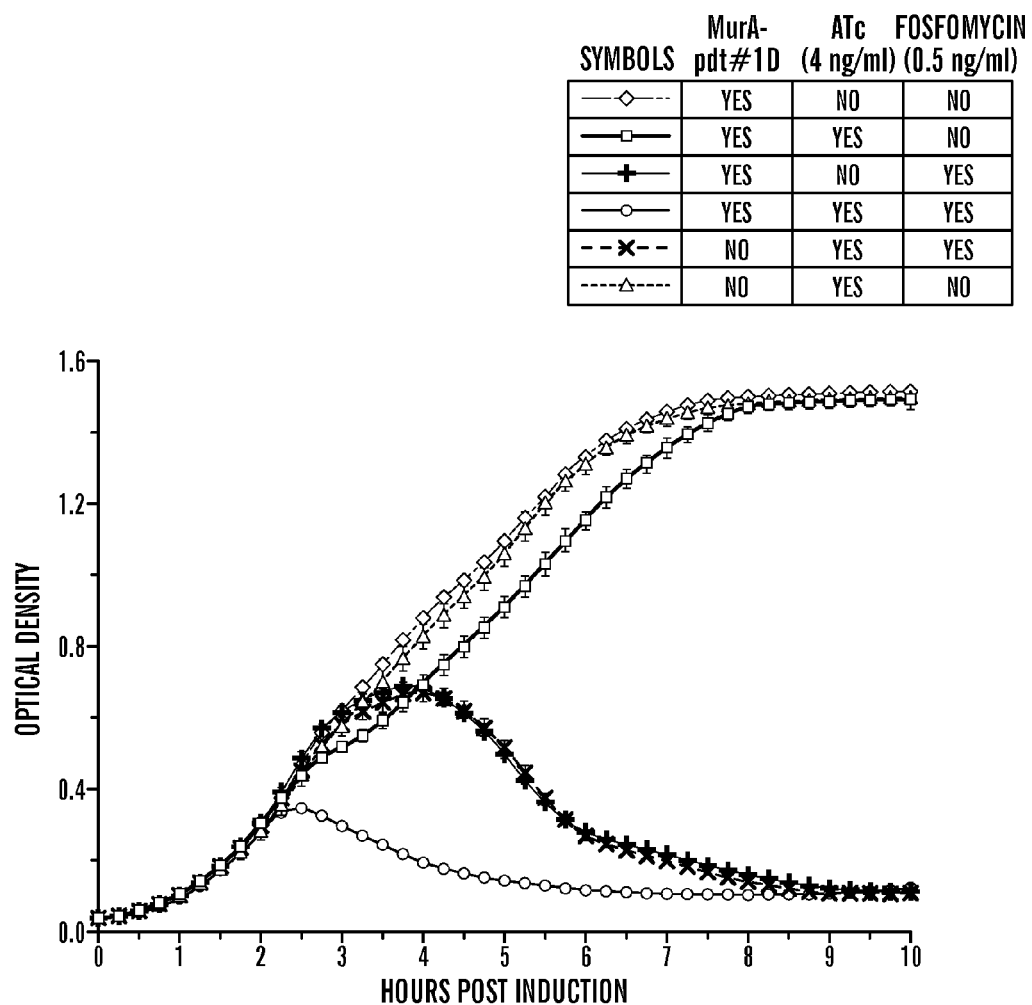
FIG. 18 shows a growth curve for MurA hypersensitivity assay. Cell growth following simultaneous addition of ATc and fosfomycin, as indicated. For cells that contain murA-pdt#1D, exposure to ATc and fosfomycin causes a larger growth defect than exposure to only ATc or only fosfomycin. Data for FIG. 13D was taken at 4 hours post ATc and fosfomycin induction.
Figure 19:
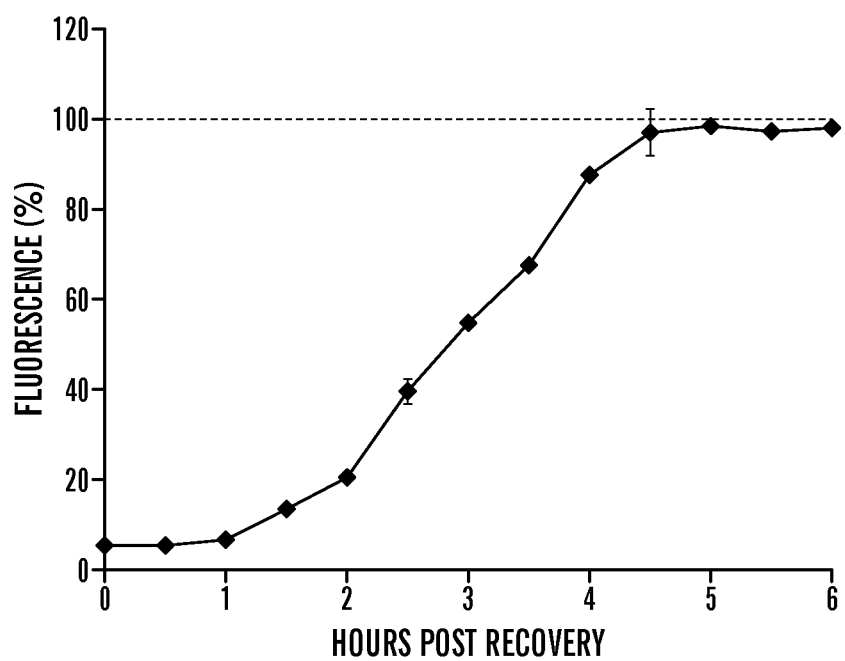
FIG. 19 shows GFP recovery. Cells containing the GFP-pdt#3 fusion were induced with ATc (50 ng/ml) for 6 hours to cause mf-Lon-mediated GFP degradation and were then moved into media without ATc and measured every 30 minutes for 6 hours. Fluorescence was measured by flow cytometry and is presented as a percent of the fluorescence of cells not exposed to ATc. Full recovery of GFP-pdt#3 levels occurs within 4.5 hours of ATc removal.

Finally, the inventors sought to develop a target-specific antibiotic screening platform in which controlled degradation of a protein of interest is used to induce hypersensitivity to compounds that exhibit target-specific inhibition. The inventors returned their focus to MurA, the known target of fosfomycin[27], and used the weak hybrid tag pdt#1 D and a range of ATc concentrations to identify mf-Lon induction conditions that produce a small murA-pdt#1D dependent growth defect (4 ng/ml ATc, see FIG. 18). Under these conditions, MurA levels are reduced to the minimum threshold necessary to sustain cell viability, making E. coli particularly vulnerable to compounds that inhibit MurA function[28]. As seen in FIG. 13D, cells that contained murA-pdt#1D displayed a 10-fold increase in sensitivity to fosfomycin. As an extension of this demonstration, the inventors also targeted the DNA damage repair protein RecA for inducible degradation, and upon mf-Lon induction, cells containing recA-pdt#3 became transiently hypersensitive to norfloxacin, a quinolone antibiotic known to cause DNA damage[29] (FIG. 13E). The synthetic degradation system presented here is facile and modular, comprising a single protease gene and a small peptide tag that provides control over both the steady-state level and inducible degradation rate of attached proteins. This degradation system represents an important advance in synthetic biology, where protein level control will provide an additional regulatory mechanism to aid in complex circuit design[30-34]. As demonstrated here for a transcription-based toggle switch, existing synthetic circuitry can be readily modified with this system to enable post-translational control while leaving the original regulatory framework intact, and use of the system to integrate multiple synthetic circuits can easily be envisioned[35,36].

Recent work by Huang et al.[37] also uses mf-Lon-mediated degradation to create a toggle switch, further demonstrating the utility of protease-driven control in synthetic systems. A promising application for this technology will be in the control of endogenous bacterial systems. Single-step genomic insertion provides a simple and efficient method to target pdt fusions to almost any E. coli gene, and the ability to control endogenous systems without disrupting the existing regulatory networks may prove particularly useful in metabolic engineering[38-40]. Further use may be found in studying essential genes whose cellular function and potential for targeted antibiotic development are major areas of research. Similar to a system developed in Mycobacterium smegmatis[41], the degradation system described herein can be used to identify essential genes that are most susceptible to degradation-induced cell death, an attractive phenotype for antibiotic development. Once a protein target is identified, the system can be used to develop target-specific hypersensitivity assays to screen for target-specific inhibitors. Finally, this system is readily transferable to other bacteria, as shown here for L. lactis. Additional pdt number variants may be needed to control degradation by endogenous proteases in these organisms, and are contemplated for use herein.

Methods

Strains and Reagents. The E. coli K-12 derivative strain MG1655Pro (F-, λ-, Spr, lacI, tetR) published previously[2,42] was used as the wild-type strain in all cases except for the synthetic toggle experiments where the inventors used MG1655ΔlacIΔaraBAD, prepared as described in the herein. Unless otherwise noted, E. coli were grown in Luria broth (LB) at 30° C. with shaking and mf-Lon expression was induced with 50 ng/ml ATc. L. lactis strain NZ900018 was used for all L. lactis experiments and grown in M17 broth containing 0.5% glucose. Antibiotics carbenicillin (100 ug/ml), kanamycin (30 ug/ml) and erythromycin (10 ug/ml) were added to the media when appropriate. All plasmids and strain mutations were verified by sequencing, and plasmid maps will be deposited in GenBank.

E. coli-Based Degradation Platform. The mf-lon gene was codon optimized for E. coli expression, placed under control of the PLtetO promoter, and integrated into the lacZ locus along with 5' and 3' transcriptional terminators to block unwanted mf-Lon expression from any proximal genomic promoters. The GFP variant GFPmut3b was used for all GFP expression, and GFP-pdt and mCherry-pdt variants were expressed from the constitutive PlacIq promoter on a high-copy plasmid containing the ColE1 origin and the kanamycin resistance cassette kanR.

L. Lactis-Based Degradation Platform. Plasmid pGPSARE5 was created to enable expression of mf-Lon and mCherry in L. lactis. Based on the plasmid pZE11-MCS2, it contains the ColElorigin of replication and ampR ampicillin resistance cassette to enable cloning in E. coli, as well as the AMβ1 origin of replication and ermR erythromycin cassette to enable replication and selection in L. lactis. Mf-lon is expressed from the inducible PnisA promoter with 3 ng/ml nisin, and mcherry is expressed from the constitutive L. lactis P32 promoter.

Flow Cytometry. Data for GFP and mCherry degradation dynamics were collected using an LSRFortessa cell analyzer equipped with a High Throughput Sampler (BD Biosciences), and data for the synthetic toggle switch were collected using a FACSArian flow cytometer (BD Biosciences).

For each measurement, cells were fixed in 1% paraformaldehyde (PFA), held at 4° C. for up to 5 days, and then diluted 1:10 in PBS for analysis. At least 5,000 cells were collected for each measurement and FloJo (Treestar) was used for data analysis.

Plate Fluorimetry and Optical Density. Fluorescence and optical density measurements were made with a SpectraMax M5 microplate reader (Molecular Devices) using excitation and emission wavelengths of 488 nm and 520 nm, respectively, with an emission filter cutoff at 515 nm Optical density was measured at 600 nm (OD600). All measurements were made in 200 µl in 96-well flat bottom plates.

PDT Mutagenesis Screens. Pdt mutant libraries were created by polymerase chain reaction (PCR) using primers containing randomized nucleotides at the indicated pdt codons. Strains containing the GFP-pdt mutants were individually picked into 96-well plates and measured by plate fluorimetry during exponential phase growth. Strains that exhibited the desired GFP degradation dynamics following induction with ATc were further characterized by flow cytometry.

Synthetic Toggle Switch. The plasmid pKDL071R8, based on pKDL07143, was altered to contain a weakened tetR ribosome binding site (RBS) to enhance toggle bistability in the minimal media conditions used. This plasmid served as the parental strain for all LacI-pdt toggle switch experiments. Pdt variants were fused to lad by overlapping PCR and cloned into pKDL071R8 using SacII and BsrGI. The arabinose inducible PBAD promoter was used to express mf-Lon from a second plasmid. Cells containing the toggle switch and mf-Lon expression plasmids were grown in 200 µl in 96-well round bottom plates at 37° C. in M9 minimal media containing 0.2% glycerol and 0.05% casamino acids, and care was taken to maintain exponential growth throughout the experiment. Cells were grown for 6 hours with either 30 ng/ml ATc or 500 µM Isopropyl β-D-1-thiogalactopyranoside (IPTG) to induce cells into the GFP+ or mCherry+ states, respectively. Cells were diluted 1:1000 into non-inducing media and allowed to grow for an additional 12 h. To induce mf-Lon, cells were grown at 37° C. shaking with 1 mM arabinose and passaged every 4 hours (~1:10 dilution) into media containing the same inducing conditions. At each time point, cells were fixed with 1% paraformaldehyde in PBS and stored at 4° for up to 5 days. Cells that did not contain the toggle switch plasmid were used to define the GFP-/mCherry-state.

Genomic Insertion of Pdt Variants. The pECT plasmids were created to serve as a template for PCR amplification of the pdt variant cassettes shown in FIG. 4a. The kanR cassette and surrounding FRT sites from pKD1344 were cloned into pWM9145 to generate pECT, which was further named according to the pdt tag variant cloned adjacent to the upstream FRT site (e.g., pECT-A contains pdt#3A). To generate PCR products for genomic integration, PDT variants were amplified from their pECT plasmid using primers that contained additional 42 base 5' extensions with homology to the C-terminus and immediate 3' untranslated region of the targeted gene, respectively. PCR products were transformed into E. coli containing pKD46 using published methods[22], and successful genomic pdt insertions were verified by PCR. Plasmid pECA102, containing Flp recombinase expressed from the PBAD promoter, was used to remove the kanR cassette, and pECA102 was subsequently cured by selection with 8% sucrose.

MurA-Induced Lysis Growth Conditions. Strains were grown in 200 µl LB in 96-well flat bottom plates with lids at 30° C. shaking in a SPECTRAMAX™ M5 plate reader. OD600 measurements were taken every 15 minutes and normalized using media-only wells. Wells on the perimeter of the plate were filled with water and not used for bacterial growth.

FtsZ Microscopy. Differential interference contrast (DIC) and fluorescence microscopy images were taken with a Nikon Eclipse Ti microscope using a 100× objective and a Coldsnap HQ2 CCD camera (Photometrics) operated with NIS-Elements Advanced Research 3.2 software. Cells in exponential growth in liquid cultures were induced with ATc, grown for 3 hours at 30° C., placed on a 300 µl pad containing PBS and 0.75% low-melt agarose (Boston Bioproducts) an immediately imaged.

Chemotactic Motility Plates. Cells in exponential growth were stabbed into soft agar plates containing 1% tryptone, 0.5% NaCl and 0.3% agar. ATc dissolved in 10 µl water was added to sterile 6 mm disks in the center of the plates immediately prior to bacterial inoculation. Plates were incubated for 18 hours at 30° C. before imaging with a Gel Logic 6000 Pro (Carestream).

Hypersensitivity Assay. Norfloxacin and ATc were simultaneously added at the indicated concentrations to cells in exponential growth in 96-well flat bottom plates, and OD600 was measured after 6 hours, with media only wells serving as absorbance controls. For targeted RecA degradation, cells in exponential growth were induced with 50 ng/ml ATc for 2 hours, if indicated, before treatment with 25 ng/ml norfloxacin for 2 hours. Cells were then serially diluted in PBS and spotted on LB plates without selection, and visible colonies forming units (CFU) were counted after incubation overnight at 30° C.

Regression Analysis. Simple linear regression models used the least-squares approach to determine the best-fit line and coefficient of determination ($R^2$).

REFERENCES

1. Guzman, L. M., Belin, D., Carson, M. J. & Beckwith, J. Tight regulation, modulation, and high-level expression by vectors containing the arabinose PBAD promoter. Journal of bacteriology 177, 4121-4130 (1995).

2. Lutz, R. & Buj ard, H. Independent and tight regulation of transcriptional units in Escherichia coli via the LacR/O, the TetR/O and AraC/I1-I2 regulatory elements. Nucleic Acids Res 25, 1203-1210 (1997).

3. Isaacs, F. J. et al. Engineered riboregulators enable post-transcriptional control of gene expression. Nat Biotechnol 22, 841-847 (2004).

4. Topp, S. et al. Synthetic riboswitches that induce gene expression in diverse bacterial species. Applied and environmental microbiology 76, 7881-7884 (2010).

5. Callura, J. M., Cantor, C. R. & Collins, J. J. Genetic switchboard for synthetic biology applications. Proc Natl Acad Sci USA 109, 5850-5855 (2012).

6. Lou, C., Stanton, B., Chen, Y. J., Munsky, B. & Voigt, C. A. Ribozyme-based insulator parts buffer synthetic circuits from genetic context. Nat Biotechnol 30, 1137-1142 (2012).

7. Qi, L., Haurwitz, R. E., Shao, W., Doudna, J. A. & Arkin, A. P. RNA processing enables predictable programming of gene expression. Nat Biotechnol 30, 1002-1006 (2012).

8. Moore, S. D. & Sauer, R. T. The tmRNA system for translational surveillance and ribosome rescue. Annu Rev Biochem 76, 101-124 (2007).

9. Andersen, J. B. et al. New unstable variants of green fluorescent protein for studies of transient gene expression in bacteria. Appl Environ Microbiol 64, 2240-2246 (1998).

10. Gritty, C., Stricker, J., Pang, W. L., Bennett, M. R. & Hasty, J. A synthetic gene network for tuning protein degradation in *Saccharomyces cerevisiae*. Mol Syst Biol 3, 127 (2007).

11. Neklesa, T. K. et al. Small-molecule hydrophobic tagging-induced degradation of HaloTag fusion proteins. Nat Chem Biol 7, 538-543 (2011).

12. Bonger, K. M., Chen, L. C., Liu, C. W. & Wandless, T. J. Small-molecule displacement of a cryptic degron causes conditional protein degradation. Nat Chem Biol 7, 531-537 (2011).

13. Banaszynski, L. A., Chen, L. C., Maynard-Smith, L. A., Ooi, A. G. & Wandless, T. J. A rapid, reversible, and tunable method to regulate protein function in living cells using synthetic small molecules. Cell 126, 995-1004 (2006).

14. Davis, J. H., Baker, T. A. & Sauer, R. T. Small-molecule control of protein degradation using split adaptors. ACS Chem Biol 6, 1205-1213 (2011).

15. Gur, E. & Sauer, R. T. Evolution of the ssrA degradation tag in *Mycoplasma*: specificity switch to a different protease. Proc Natl Acad Sci USA 105, 16113-16118 (2008).

16. Flynn, J. M. et al. Overlapping recognition determinants within the ssrA degradation tag allow modulation of proteolysis. Proc Natl Acad Sci USA 98, 10584-10589 (2001).

17. Ge, Z. & Karzai, A. W. Co-evolution of multipartite interactions between an extended tmRNA tag and a robust Lon protease in *Mycoplasma*. Mol Microbiol 74, 1083-1099 (2009).

18. Mierau, I. & Kleerebezem, M. 10 years of the nisin-controlled gene expression system (NICE) in *Lactococcus lactis*. Applied microbiology and biotechnology 68, 705-717 (2005).

19. Botos, I. et al. The catalytic domain of *Escherichia coli* Lon protease has a unique fold and a Ser-Lys dyad in the active site. The Journal of biological chemistry 279, 8140-8148 (2004).

20. Gardner, T. S., Cantor, C. R. & Collins, J. J. Construction of a genetic toggle switch in *Escherichia coli*. Nature 403, 339-342 (2000).

21. Moon, T. S. et al. Construction of a genetic multiplexer to toggle between chemosensory pathways in *Escherichia coli*. J Mol Biol 406, 215-227 (2011).

22. Datsenko, K. A. & Wanner, B. L. One-step inactivation of chromosomal genes in *Escherichia coli* K-12 using PCR products. Proc Natl Acad Sci USA 97, 6640-6645 (2000).

23. Sharan, S. K., Thomason, L. C., Kuznetsov, S. G. & Court, D. L. Recombineering: a homologous recombination-based method of genetic engineering. Nat Protoc 4, 206-223 (2009).

24. Brown, E. D., Vivas, E. I., Walsh, C. T. & Kolter, R. MurA (MurZ), the enzyme that catalyzes the first committed step in peptidoglycan biosynthesis, is essential in *Escherichia coli*. Journal of bacteriology 177, 4194-4197 (1995).

25. Adams, D. W. & Errington, J. Bacterial cell division: assembly, maintenance and disassembly of the Z ring. Nat Rev Microbiol 7, 642-653 (2009).

26. Silversmith, R. E. Auxiliary phosphatases in two-component signal transduction. Curr Opin Microbiol 13, 177-183 (2010).

27. Kim, D. H. et al. Characterization of a Cys115 to Asp substitution in the *Escherichia coli* cell wall biosynthetic enzyme UDP-GlcNAc enolpyruvyl transferase (MurA) that confers resistance to inactivation by the antibiotic fosfomycin. Biochemistry 35, 4923-4928 (1996).

28. DeVito, J. A. et al. An array of target-specific screening strains for antibacterial discovery. Nat Biotechnol 20, 478-483 (2002).

29. Khodursky, A. B. & Cozzarelli, N. R. The mechanism of inhibition of topoisomerase IV by quinolone antibacterials. J Biol Chem 273, 27668-27677 (1998).

30. Lu, T. K., Khalil, A. S. & Collins, J. J. Next-generation synthetic gene networks. Nat Biotechnol 27, 1139-1150 (2009).

31. Weber, W. & Fussenegger, M. Emerging biomedical applications of synthetic biology. Nat Rev Genet 13, 21-35 (2012).

32. Rodrigo, G., Landrain, T. E. & Jaramillo, A. De novo automated design of small RNA circuits for engineering synthetic riboregulation in living cells. Proceedings of the National Academy of Sciences (2012).

33. Tabor, J. J. et al. A synthetic genetic edge detection program. Cell 137, 1272-1281 (2009).

34. Pedraza, J. M. & van Oudenaarden, A. Noise propagation in gene networks. Science 307, 1965-1969 (2005).

35. Danino, T., Mondragon-Palomino, O., Tsimring, L. & Hasty, J. A synchronized quorum of genetic clocks. Nature 463, 326-330 (2010).

36. Slusarczyk, A. L., Lin, A. & Weiss, R. Foundations for the design and implementation of synthetic genetic circuits. Nat Rev Genet 13, 406-420 (2012).

37. Huang, D. C., Holtz, W. J. & Maharbiz, M. M. A genetic bistable switch utilizing nonlinear protein degradation. J Biol Eng 6, 9 (2012).

38. Lee, J. W. et al. Systems metabolic engineering of microorganisms for natural and non-natural chemicals. Nature chemical biology 8, 536-546 (2012).

39. Holtz, W. J. & Keasling, J. D. Engineering static and dynamic control of synthetic pathways. Cell 140, 19-23 (2010).

40. Huo, Y. X. et al. Conversion of proteins into biofuels by engineering nitrogen flux. Nat Biotechnol 29, 346-351 (2011).

41. Wei, J. R. et al. Depletion of antibiotic targets has widely varying effects on growth. Proc Natl Acad Sci USA 108, 4176-4181 (2011).

42. Callura, J. M., Dwyer, D. J., Isaacs, F. J., Cantor, C. R. & Collins, J. J. Tracking, tuning, and terminating microbial physiology using synthetic riboregulators. Proc Natl Acad Sci USA 107, 15898-15903 (2010).

43. Litcofsky, K. D., Afeyan, R. B., Krom, R. J., Khalil, A. S. & Collins, J. J. Iterative plug-and-play methodology for constructing and modifying synthetic gene networks. Nat Methods 9, 1077-1080 (2012).

44. Baba, T. et al. Construction of *Escherichia coli* K-12 in-frame, single-gene knockout mutants: the Keio collection. Molecular systems biology 2, 2006 0008 (2006).

45. Metcalf, W. W. et al. Conditionally replicative and conjugative plasmids carrying lacZ alpha for cloning, mutagenesis, and allele replacement in bacteria. Plasmid 35, 1-13 (1996).

Supplementary Methods and References

Strain Construction. The parental strains for all experiments are *E. coli* MG1655 (ATCC no.47076) and *L. lactis* NZ9000[1]. MG1655ΔlacIΔaraBAD was created through P1 phage transduction of lacI:kanR from the Keio collection into MG1655, and Red-recombinase-mediated homologous recombination was used to create the in-frame deletion of araBAD according to described methods[3]. Flp recombinase, expressed on pECA102 (10 mM arabinose for 4 hours) was used to remove the kanR cassette in each case. DH5αλpir[4] was used for cloning. Endogenous *E. coli* protease deletions were constructed by P1 phage transduction of the corresponding mutations from the Keio collection into MG1655pro[5] followed by kanR cassette removal as detailed above. To construct the mf-Lon expression cassette, the inventors codon optimized mf-lon for expression in *E. coli* and forward engineered a strong RBS to enable high expression[6]. The gene and RBS were cloned into pZE11 using EcoRI and HindIII. The inventors used overlapping PCR to add a transcriptional terminator 5' of the PLtetO promoter in this plasmid, then cloned this expression cassette, which includes the 5' terminator, PLtetO promoter, mf-lon gene, and 3'terminator, into pWM91-lacZ, a derivative of pWM917 that includes a 1 kb lacZ targeting region. The resulting plasmid, pECL275, was introduced into MG1655pro by conjugation from Sm10λpir, single integrants were selected on carbenicillin plates, grown in rich media for 8 hours, and then selected on plates containing 1% tryptone, 0.5% yeast extract, 8% sucrose and 1.5% agar to select for plasmid excision. The resulting colonies were screened by PCR for the mf-Lon expression cassette. Mf-Lon variants that contain ec-AAV and ec-ASV fusions and the S692A point mutation were constructed in the same manner. Plasmid pECL275 will be deposited in GenBank.

Plasmid Construction. Pdt variants were fused to GFPmut3b[8] and mCherry by PCR and were cloned into pZE21-MCS[9] using KpnI and HindIII restriction sites. The constitutive PlacIq promoter[10] was inserted using XhoI and KpnI. For the synthetic toggle switch experiments, KpnI and HindIII sites were used to clone mf-lon into pZA11-MCS and the PBAD promoter was subsequently cloned in using the XhoI and KpnI sites. To clone the pECT plasmids used to generate genomic pdt insertions, the kanR cassette and surrounding FRT sites was PCR amplified from pKD132 and cloned into pWM917 using MluI and XhoI. Pdt tag variants were cloned into pECT using XhoI and SacII, and were named according to the inserted pdt tag (e.g., pECT5A contains pdt#5A). To generate, pECA102, Flp recombinase was cloned into pBAD24[11] using KpnI, and the constitutively expressed sacB cassette was subsequently amplified from pWM91[7] and cloned into the plasmid using partial MluI and SalI digestion and ligation. For the toggle switch experiments, lacI-pdt fusions were generated by overlapping PCR and cloned into pKDL071R8 using BsrGI and SacII. TetR-pdt fusions were cloned into pKDL071R9 using NheI and SacI. Plasmids were verified by sequencing and will be deposited in GenBank.

*Lactococcus lactis* Plasmids and Cloning. Plasmid pGPSARE5 was created to enable expression of mf-Lon and mCherry in *L. lactis*. Based on the plasmid pZE11-MCS[9], it contains the ColE1 origin of replication and ampR ampicillin resistance cassette to enable cloning in *E. coli*, and it contains the AMβ1 origin of replication and ermR erythromycin resistance cassette from pVE5523[12] to enable replication and selection in *L. lactis*. In pGPSARE5, mCherry is expressed from the constitutive P32 promoter[13] and $^{mf}$-Lon is expressed from the inducible promoter $P_{nisA}$[1] with 3 ng/ml nisin. pGPSARE5 and the versions containing mCherry-pdt variants were transformed into *L. lactis* according to established protocols [14].

*Genomic insertion of Pdt variants.* Pdt variants were amplified from their pECT plasmid using primers P1 and P2 that contained additional 42 base 5' extensions with homology to the C-terminus and immediate 3' UTR of the targeted gene, respectively. Note that the endogenous gene's stop codon should not be included in the P1 5' extension. The base P1 and P2 primer sequences and the full length primers used to target murA, ftsZ, cheZ and recA are listed below.

P1:
(SEQ ID NO: 104)
GCGGCGAACAAAAACGAA

P2:
(SEQ ID NO: 105)
GGGGATCCGTCGACCTGC.

P1-murA:
(SEQ ID NO: 106)
CTGCGCGCTTTAGGTGCAAATATTGAGCGTGTGAAAGGCGAAGCGGCGAA

CAAAAACGAA

P2-murA:
(SEQ ID NO: 107)
CTGGCGGTAGCCCCGCGAACGGGGCTGCCAGCTCTCAGACGAGGGGATCC

GTCGACCTGC

P1-ftsZ:
(SEQ ID NO: 108)
GATTATCTGGATATCCCAGCATTCCTGCGTAAGCAAGCTGATGCGGCGAA

CAAAAACGAA

P2-ftsZ:
(SEQ ID NO: 109)
GTTTAGCACAAAGAGCCTCGAAACCCAAATTCCAGTCAATTCGGGGATCC

GTCGACCTGC

P1-cheZ:
(SEQ ID NO: 110)
AGTCAGGATCAGGTGGACGATTTGTTGGATAGTCTTGGATTTGCGGCGAA

CAAAAACGAA

P2-cheZ:
(SEQ ID NO: 111)
CCGCCTGATATGACGTGGTCACGCCACATCAGGCAATACAAAGGGGATCC

GTCGACCTGC

P1-recA:
(SEQ ID NO: 112)
GTAGATGATAGCGAAGGCGTAGCAGAAACTAACGAAGATTTTGCGGCGAA

CAAAAACGAA

P2-recA:
(SEQ ID NO: 113)
AAAAGGGCCGCAGATGCGACCCTTGTGTATCAAACAAGACGAGGGGATCC

GTCGACCTGC

1. Mierau, I. & Kleerebezem, M. 10 years of the nisin-controlled gene expression system (NICE) in *Lactococcus lactis*. Applied microbiology and biotechnology 68, 705-717 (2005).

2. Baba, T. et al. Construction of *Escherichia coli* K-12 in-frame, single-gene knockout mutants: the Keio collection. Molecular systems biology 2, 2006 0008 (2006).

3. Datsenko, K. A. & Wanner, B. L. One-step inactivation of chromosomal genes in *Escherichia coli* K-12 using PCR products. Proc Natl Acad Sci USA 97, 6640-6645 (2000).

4. Metcalf, W. W., Jiang, W. & Wanner, B. L. Use of the rep technique for allele replacement to construct new *Escherichia coli* hosts for maintenance of R6K gamma origin plasmids at different copy numbers. Gene 138, 1-7 (1994).

5. Callura, J. M., Dwyer, D. J., Isaacs, F. J., Cantor, C. R. & Collins, J. J. Tracking, tuning, and terminating microbial physiology using synthetic riboregulators. Proc Natl Acad Sci USA 107, 15898-15903 (2010).

6. Salis, H. M., Mirsky, E. A. & Voigt, C. A. Automated design of synthetic ribosome binding sites to control protein expression. Nat Biotechnol 27, 946-950 (2009).

7. Metcalf, W. W. et al. Conditionally replicative and conjugative plasmids carrying lacZ alpha for cloning, mutagenesis, and allele replacement in bacteria. Plasmid 35, 1-13 (1996).

8. Cormack, B. P., Valdivia, R. H. & Falkow, S. FACS-optimized mutants of the green fluorescent protein (GFP). Gene 173, 33-38 (1996).

9. Lutz, R. & Buj ard, H. Independent and tight regulation of transcriptional units in *Escherichia coli* via the LacR/O, the TetR/O and AraC/I1-I2 regulatory elements. Nucleic Acids Res 25, 1203-1210 (1997).

10. Muller-Hill, B., Crapo, L. & Gilbert, W. Mutants that make more lac repressor. Proc Natl Acad Sci USA 59, 1259-1264 (1968).

11. Guzman, L. M., Belin, D., Carson, M. J. & Beckwith, J. Tight regulation, modulation, and high-level expression by vectors containing the arabinose PBAD promoter. Journal of bacteriology 177, 4121-4130 (1995).

12. Dieye, Y., Usai, S., Clier, F., Gruss, A. & Piard, J. C. Design of a protein-targeting system for lactic acid bacteria. J Bacteriol 183, 4157-4166 (2001).

13. van de Guchte, M., Kok, J. & Venema, G. Gene expression in *Lactococcus lactis*. FEMS microbiology reviews 8, 73-92 (1992).

14. Holo, H. & Nes, I.F. Transformation of Lactococcus by electroporation. Methods in molecular biology 47, 195-199 (1995).

It should be noted that the pdt sequences in Example 1 are numbered using a different numbering convention than the pdt sequences in Example 2. The following Table indicates the corresponding pdt sequences from Example 1 correlated to the pdt sequences described in Example 2.

TABLE 9

Naming Reconciliation Table for sequences described in Examples 1 and 2.

| Name from Example 2 | Corresponding pdt name from Example 1 | aa13-15 | aa24-27 |
|---|---|---|---|
| No tag | No tag | | |
| pdt | pdt | PTF | YAFA |
| pdt#1 | pdt#1 | PTF | RLQL |
| pdt#2 | pdt#3 | PTF | YLSQ |
| pdt#3 | pdt#5 | PTF | RRRV |
| pdt#4 | pdt#8 | PTF | HAQP |
| pdt#5 | pdt#10 | PTF | RARQ |
| pdt#6 | pdt#2 | PTF | ICRL |
| pdt#3A | N/A | FKL | RRRV |
| pdt#3B | pdt#5 | ARAI | RRRV |
| pdt#3C | pdt#5H | AQP | RRRV |
| pdt#3D | pdt#5B | APN | RRRV |
| pdt#3E | N/A | PDG | RRRV |

TABLE 8

Pdt identification and characterization for GFP degradation.

| Name | aa13-15* | aa24-27* | 0 ng/ml ATc | 50 ng/ml ATc | SD** (0) | SD (50) | SEQ ID NO: |
|---|---|---|---|---|---|---|---|
| No tag | | | 100% | 93% | 3% | 1% | |
| pdt | PTF | YAFA | 50% | 1% | 5% | 1% | 1 |
| pdt#1 | PTF | RLQL | 40% | 1% | 3% | 1% | 2 |
| pdt#2 | PTF | YLSQ | 77% | 2% | 5% | 0% | 4 |
| pdt#3 | PTF | RRRV | 99% | 5% | 10% | 1% | 6 |
| pdt#4 | PTF | HAQP | 118% | 5% | 9% | 0% | 9 |
| pdt#5 | PTF | RARQ | 129% | 4% | 9% | 1% | 11 |
| pdt#6 | PTF | ICRL | 77% | 2% | 8% | 0% | 3 |
| pdt#3A | FKL | RRRV | 115% | 27% | 3% | 3% | 114 |
| pdt#3B | RAI | RRRV | 100% | 38% | 3% | 2% | 18 |
| pdt#3C | AQP | RRRV | 107% | 48% | 6% | 3% | 22 |
| pdt#3D | APN | RRRV | 104% | 66% | 3% | 1% | 19 |
| pdt#3E | PDG | RRRV | 112% | 87% | 2% | 2% | 115 |

*aa indicates amino acid. The complete pdt tag amino acid sequence is here (targeted regions are underlined): AANKNEENTNEVPTFMLNAGQANYAFA (SEQ ID NO: 26)
**Standard Deviation (SD) of three biological replicates for 0 ng/ml ATc induction (0) and 50 ng/ml ATc induction (50)

The invention claimed is:

1. A composition comprising:
a modified *Mesoplasma florum* ssrA protein degradation tag or a polynucleotide construct encoding the same;

wherein the modified degradation tag is degraded by *Mesoplasma florum* Lon protease at a higher rate compared to the unmodified *Mesoplasma florum* ssrA degradation tag, wherein the modified protein degradation tag is not degraded by ClpXP, an *E. coli* Lon protease, or an *Lactococcus lactis* protease, and wherein the modified protein degradation tag comprises one or more substitutions of amino acid residues corresponding to amino acids 24-27 of SEQ ID NO: 1.

2. The composition of claim 1, wherein the substitutions comprise one or more arginine and/or glutamine residues.

3. The composition of claim 1, wherein the modified degradation tag has an amino acid sequence in place of residues 24 to 27 of SEQ ID NO: 1 selected from: RLQL (SEQ ID NO: 30), ICRL (SEQ ID NO: 35), YLSQ (SEQ ID NO: 31), YQYR (SEQ ID NO: 116), RRRV (SEQ ID NO: 117), HISP (SEQ ID NO: 118), RICR (SEQ ID NO: 119), HAQP (SEQ ID NO: 120), RARQ (SEQ ID NO: 121), VVRR (SEQ ID NO: 122), RAQQ (SEQ ID NO: 123), RRQL (SEQ ID NO: 124), and QRQRQ (SEQ ID NO: 125).

4. The composition of claim 1, wherein the modified degradation tag is fused to a target protein.

5. The composition of claim 4, wherein the modified degradation tag is expressed in a bacterial cell.

6. The composition of claim 5, wherein the bacterial cell is *E. coli*.

7. The composition of claim 5, wherein the bacterial cell is *Lactococcus lactis*.

8. The composition of claim 1, wherein the composition is a DNA vector comprising a multiple cloning site positioned for creation of a fusion protein with the modified degradation tag.

9. The composition of claim 8, wherein the DNA vector comprises one or more regulatory elements for expression of the fusion protein in bacterial cells.

* * * * *